United States Patent
Zhao et al.

(10) Patent No.: US 12,398,118 B2
(45) Date of Patent: Aug. 26, 2025

(54) RHO-ASSOCIATED PROTEIN KINASE INHIBITOR, PHARMACEUTICAL COMPOSITION COMPRISING SAME, AND USE THEREOF

(71) Applicant: BEIJING TIDE PHARMACEUTICAL CO., LTD., Beijing (CN)

(72) Inventors: Yanping Zhao, Beijing (CN); Hongjun Wang, Beijing (CN); Gong Li, Beijing (CN); Yuanyuan Jiang, Beijing (CN); Xiang Li, Beijing (CN); Bin Liu, Beijing (CN); Kai Liu, Beijing (CN); Weiting Zhong, Beijing (CN); Fajie Li, Beijing (CN); Jing Zhao, Beijing (CN); Jianmei Pang, Beijing (CN); Liying Zhou, Beijing (CN)

(73) Assignee: BEIJING TIDE PHARMACEUTICAL CO., LTD., Beijing (CN)

( * ) Notice: Subject to any disclaimer, the term of this patent is extended or adjusted under 35 U.S.C. 154(b) by 1046 days.

(21) Appl. No.: 17/292,036

(22) PCT Filed: Nov. 8, 2019

(86) PCT No.: PCT/CN2019/116453
§ 371 (c)(1),
(2) Date: May 7, 2021

(87) PCT Pub. No.: WO2020/094111
PCT Pub. Date: May 14, 2020

(65) Prior Publication Data
US 2022/0002266 A1 Jan. 6, 2022

(30) Foreign Application Priority Data
Nov. 9, 2018 (WO) ................ PCT/CN2018/114801

(51) Int. Cl.
*C07D 401/14* (2006.01)
*C07D 403/14* (2006.01)
*C07D 405/14* (2006.01)
*C07D 495/04* (2006.01)

(52) U.S. Cl.
CPC ......... *C07D 401/14* (2013.01); *C07D 403/14* (2013.01); *C07D 405/14* (2013.01); *C07D 495/04* (2013.01)

(58) Field of Classification Search
CPC .. C07D 401/14; C07D 403/14; C07D 405/14; C07D 495/04; C07D 409/14; A61K 31/506; A61P 25/28; A61P 27/00; A61P 35/00
See application file for complete search history.

(56) References Cited

U.S. PATENT DOCUMENTS

| | | | | |
|---|---|---|---|---|
| 10,323,023 | B2 * | 6/2019 | Zhao | A61K 31/53 |
| 10,329,282 | B2 * | 6/2019 | Zhao | A61K 31/4155 |
| 11,390,609 | B2 * | 7/2022 | Zhao | C07D 471/10 |
| 2008/0045566 | A1 | 2/2008 | Ray et al. | |
| 2010/0056568 | A1 | 3/2010 | Plettenburg et al. | |
| 2010/0144707 | A1 * | 6/2010 | Bartolozzi | C07D 403/12 514/622 |
| 2014/0057942 | A1 | 2/2014 | Leysen et al. | |
| 2016/0237095 | A1 * | 8/2016 | Kim | A61P 3/10 |
| 2017/0112832 | A1 | 4/2017 | Zanin-Zhorov et al. | |

FOREIGN PATENT DOCUMENTS

| | | |
|---|---|---|
| CN | 101208094 | 6/2008 |
| CN | 101522633 | 9/2009 |
| CN | 101573338 | 11/2009 |
| CN | 103534249 | 1/2014 |
| CN | 104903312 | 9/2015 |
| WO | 2010011620 | 1/2010 |
| WO | 2015054317 | 4/2015 |
| WO | 2015157556 | 10/2015 |

OTHER PUBLICATIONS

Stella et al., Prodrugs: Challenges and Rewards, Part 1, 2007 (Year: 2007).*
Scott Obach, Pharmacol Rev 65:578-640, Apr. 2013 (Year: 2013).*
Green et al., Design, Synthesis, and Structure-Activity Relationships of Pyridine-Based Rho Kinase (ROCK) Inhibitors J. Med. Chem. 2015, 58, 5028-5037 (Year: 2015).*

* cited by examiner

*Primary Examiner* — Clinton A Brooks
*Assistant Examiner* — Izabela Schmidt
(74) *Attorney, Agent, or Firm* — Robin L. Teskin; Baker, Donelson, Bearman, Caldwell & Berkowitz PC

(57) ABSTRACT

A Rho-associated protein kinase (ROCK) inhibitor represented by formula (I), a pharmaceutical composition comprising same, and a use thereof for preventing or treating ROCK-mediated diseases.

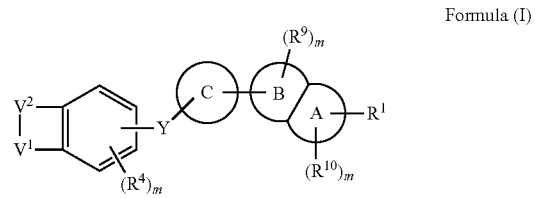

Formula (I)

13 Claims, No Drawings

RHO-ASSOCIATED PROTEIN KINASE INHIBITOR, PHARMACEUTICAL COMPOSITION COMPRISING SAME, AND USE THEREOF

CROSS-REFERENCE TO RELATED APPLICATIONS

This application is a U.S. National Phase application of Int'l Appl. No. PCT/CN2019/116453, filed Nov. 8, 2019, which claims priority to Int'l Appl. No. PCT/CN2018/114801, filed Nov. 9, 2018, each of which are incorporated herein by reference in their entireties.

FIELD OF THE INVENTION

The present invention relates to a Rho-associated protein kinase inhibitor, a pharmaceutical composition comprising the same, and use thereof for the prophylaxis or treatment of a disease mediated by the Rho-associated protein kinase (ROCK).

BACKGROUND OF THE INVENTION

Rho-associated protein kinase (ROCK) is a serine/threonine kinase from the AGC kinase family, and comprises two isoforms, ROCK1 and ROCK2. ROCK1 and ROCK2 are expressed and regulated differently in specific tissues. For example, ROCK1 is ubiquitously expressed at a relatively high level, while ROCK2 is preferentially expressed in heart, brain and skeletal muscle. ROCK is the first downstream effector of the Rho protein discovered, and its biological function is achieved by phosphorylating the downstream effector proteins (MLC, Lin-11, Is1-1, LIMK, ERM, MARCKS, CRMP-2 etc.). Studies have shown that various diseases (e.g., pulmonary fibrosis, cardiac-cerebral vascular disease, neurological disease and cancer etc.) are related to the pathways mediated by ROCK. As such, ROCK is considered as an important target in the development of novel drugs.

However, at present, only Fasudil is approved as a ROCK inhibitor for the treatment of cerebral vasospasm and ischemia in Japan. Although various small molecule ROCK inhibitors have been reported by now, most of them are for topical ophthalmic application, and no small molecule ROCK inhibitor suitable for systemic administration is available.

SUMMARY OF THE INVENTION

The present invention provides a compound for use as a ROCK (preferably ROCK2) inhibitor, it has superior properties, such as excellent inhibitory activity on ROCK (preferably ROCk2), good selectivity (higher selectivity towards ROCK2 as compared with ROCK1), better physicochemical properties (e.g., solubility, physical and/or chemical stability), improved pharmacokinetic properties (e.g., improved bioavailability, proper half-life and duration of action), improved safety (low toxicity and/or less side effects, wide therapeutic window), and the like.

According to an aspect of the present invention, a compound or a pharmaceutically acceptable salt, ester, stereoisomer, polymorph, solvate, N-oxide, isotopically labeled compound, metabolite or prodrug thereof is provided, wherein the compound has the structure of Formula (I):

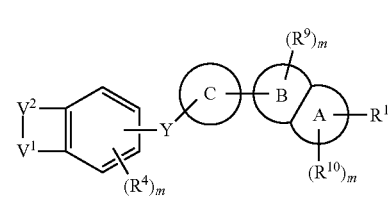

Formula (I)

wherein:
$V^1$ is selected from the group consisting of —$CR^2$=N—, —N=$CR^2$—, —$NR^3C$(=O)— and —C(=O)$NR^3$—;
$V^2$ is selected from the group consisting of —$CR^2$=N—, —N=$CR^2$—, —$(CR^2R^{2'})_n$— and —$(CR^2$=$CR^{2'})_n$—;
Y is selected from the group consisting of a direct bond, C(=O), O, S(=O)$_i$ and NR;
R is selected from the group consisting of H, $C_{1-6}$ alkyl, $C_{2-6}$ alkenyl, $C_{2-6}$ alkynyl, saturated or partially unsaturated $C_{3-10}$ cyclic hydrocarbyl, saturated or partially unsaturated 3-10-membered heterocyclyl, $C_{6-10}$ aryl, 5-14-membered heteroaryl and $C_{6-12}$ aralkyl, and at most 2 ring members in the cyclic hydrocarbyl and heterocyclyl are C(=O);
ring A and ring B are each independently selected from the group consisting of saturated or partially unsaturated $C_{3-10}$ hydrocarbon ring, saturated or partially unsaturated 3-10-membered heterocycle, $C_{6-10}$ aromatic ring and 5-14-membered heteroaromatic ring, and at most 2 ring members in the hydrocarbon ring and heterocycle are C(=O);
ring C is

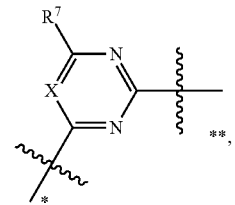

which is attached to Y at either of the two positions labeled * or **, and is attached to ring B at the other position;
X is selected from the group consisting of $CR^8$ and N;
$R^1$ is selected from the group consisting of —C(=O)$R^{1a}$, —C(=O)$OR^{1a}$ and —C(=O)$NR^{1a}R^{1b}$;
$R^{1a}$ and $R^{1b}$ are each independently selected from the group consisting of H, halogen, amino, cyano, nitro, $C_{1-6}$ alkyl, $C_{2-6}$ alkenyl, $C_{2-6}$ alkynyl, $C_{3-10}$ cyclic hydrocarbyl, 3-10-membered heterocyclyl, $C_{6-10}$ aryl, 5-14-membered heteroaryl, $C_{6-12}$ aralkyl, —C(=O)$R^5$, —OC(=O)$R^5$, —C(=O)$OR^5$, —S(=O)$R^5$, —S(=O)$_2 R^5$, —S(=O)$_2NR^5R^6$, —$NR^5R^6$, —C(=O)$NR^5R^6$, —$NR^5$—C(=O)$R^6$, —$NR^5$—C(=O)$OR^6$, —$NR^5$—(=O)$_2$—$R^6$, —$NR^5$—C(=O)—$NR^5R^6$, —$C_{1-6}$ alkylene-$NR^5R^6$, —$C_{1-6}$ alkylene-$OR^5$ and —O—$C_{1-6}$ alkylene-$NR^5R^6$; alternatively, $R^{1a}$ and $R^{1b}$ together with the atom to which they are attached form a 3-12-membered heterocycle or heteroaromatic ring;
$R^2$, $R^{2'}$, $R^3$, $R^4$, $R^7$, $R^8$, $R^9$ and $R^{10}$, at each occurrence, are each independently selected from the group consisting of H, halogen, amino, cyano, nitro, $C_{1-6}$ alkyl, $C_{2-6}$ alkenyl, $C_{2-6}$ alkynyl, $C_{3-10}$ cyclic hydrocarbyl, 3-10-membered heterocyclyl, $C_{6-10}$ aryl, 5-14-membered heteroaryl, $C_{6-12}$ aralkyl, —C(=O)$R^5$, —OC(=O)$R^5$, —C(=O)O$R^5$, —S(=O)$R^5$, —S(=O)$_2R^5$, —S(=O)$_2$N$R^5R^6$, —N$R^5R^6$, —C(=O)N$R^5R^6$, —N$R^5$—C(=O)$R^6$, —N$R^5$—C(=O)O$R^6$, —N$R^5$—S(=O)$_2$—$R^6$, —N$R^5$—C(=O)—N$R^5R^6$, —$C_{1-6}$ alkylene-N$R^5R^6$, —$C_{1-6}$ alkylene-O(P=O)(OH)$_2$ and —O—$C_{1-6}$ alkylene-N$R^5R^6$; alternatively, $R^7$ and $R^8$ together with the group to which they are attached form a $C_{6-10}$ aromatic ring or 5-14-membered heteroaromatic ring;

the alkyl, alkylene, alkenyl, alkenylene, alkynyl, cyclic hydrocarbyl, hydrocarbon ring, heterocyclyl, heterocycle, aryl, aromatic ring, heteroaryl, heteroaromatic ring and aralkyl, at each occurrence, are each optionally substituted with one or more substituents independently selected from the group consisting of: halogen, hydroxyl, oxo, amino, cyano, nitro, $C_{1-6}$ alkyl, $C_{2-6}$ alkenyl, $C_{2-6}$ alkynyl, $C_{3-6}$ cyclic hydrocarbyl, 3-10-membered heterocyclyl, $C_{6-10}$ aryl, 5-14-membered heteroaryl, $C_{6-12}$ aralkyl, =N—O$R^5$, —C(=NH)NH$_2$, —C(=O)$R^5$, —OC(=O)$R^5$, —C(=O)O$^5$, —S(=O)$R^5$, —S(=O)$_2R^5$, —S(=O)$_2$N$R^5R^6$, —N$R^5R^6$, —C(=O)N$R^5R^6$, —N$R^5$—C(=O)$R^6$, —N$R^5$—C(=O)O$R^6$, —N$R^5$—S(=O)$_2$—$R^6$, —N$R^5$—C(=O)—N$R^5R^6$, —$C_{1-6}$ alkylene- N$R^5R^6$ and —O—$C_{1-6}$ alkylene-N$R^5R^6$, and the alkyl, alkylene, alkenyl, alkynyl, cyclic hydrocarbyl, heterocyclyl, aryl, heteroaryl and aralkyl are further optionally substituted with one or more substituents independently selected from the group consisting of: halogen, hydroxyl, oxo, amino, cyano, nitro, $C_{1-6}$ alkyl, $C_{3-6}$ cyclic hydrocarbyl, 3-10-membered heterocyclyl, $C_{6-10}$ aryl, 5-14-membered heteroaryl and $C_{6-12}$ aralkyl;

$R^5$ and $R^6$, at each occurrence, are each independently selected from the group consisting of H, $C_{1-6}$ alkyl, $C_{3-10}$ cyclic hydrocarbyl, 3-10-membered heterocyclyl, $C_{6-10}$ aryl, 5-14-membered heteroaryl and $C_{6-12}$ aralkyl; alternatively, when $R^5$ and $R^6$ are attached to a same nitrogen atom, $R^5$ and $R^6$ together with the atom to which they are attached optionally form a 3-12-membered heterocycle or heteroaromatic ring;

m, at each occurrence, is each independently an integer of 0, 1, 2 or 3;

n is an integer of 0, 1, 2, 3 or 4; and i is an integer of 0, 1 or 2.

According to another aspect of the invention, a pharmaceutical composition comprising a prophylactically or therapeutically effective amount of the compound of the present invention or a pharmaceutically acceptable salt, ester, stereoisomer, polymorph, solvate, N-oxide, isotopically labeled compound, metabolite or prodrug thereof and one or more pharmaceutically acceptable carriers is provided, and the pharmaceutical composition is preferably in the form of a solid, semi-solid, liquid, or gas preparation.

According to another aspect of the invention, use of the compound of the present invention or a pharmaceutically acceptable salt, ester, stereoisomer, polymorph, solvate, N-oxide, isotopically labeled compound, metabolite or prodrug thereof or the pharmaceutical composition of the present invention in the preparation of a medicament for use as a Rho-associated protein kinase (ROCK) inhibitor, preferably a selective ROCK2 inhibitor, is provided.

According to another aspect of the invention, the compound of the present invention or a pharmaceutically acceptable salt, ester, stereoisomer, polymorph, solvate, N-oxide, isotopically labeled compound, metabolite or prodrug thereof or the pharmaceutical composition of the present invention for use as a Rho-associated protein kinase (ROCK) inhibitor, preferably a selective ROCK2 inhibitor, is provided.

According to another aspect of the invention, a method for the prophylaxis or treatment of a disease mediated by the Rho-associated protein kinase (ROCK) is provided, wherein the method comprises administering to a subject in need thereof an effective amount of the compound of the present invention or a pharmaceutically acceptable salt, ester, stereoisomer, polymorph, solvate, N-oxide, isotopically labeled compound, metabolite or prodrug thereof or the pharmaceutical composition of the present invention.

DETAILED DESCRIPTION OF THE INVENTION

Definition

Unless otherwise defined in the context, all technical and scientific terms used herein are intended to have the same meaning as commonly understood by a person skilled in the art. References to techniques employed herein are intended to refer to the techniques as commonly understood in the art, including variations on those techniques or substitutions of equivalent techniques which would be apparent to a person skilled in the art. While it is believed that the following terms will be readily understood by a person skilled in the art, the following definitions are nevertheless put forth to better illustrate the present invention.

The terms "contain", "include", "comprise", "have", or "relate to", as well as other variations used herein are inclusive or open-ended, and do not exclude additional, unrecited elements or method steps.

As used herein, the term "alkylene" refers to a saturated divalent hydrocarbyl, preferably refers to a saturated divalent hydrocarbyl having 1, 2, 3, 4, 5 or 6 carbon atoms, e.g., methylene, ethylene, propylene or butylene.

As used herein, the term "alkyl" is defined as a linear or branched saturated aliphatic hydrocarbon. In some embodiments, alkyl has 1-12, e.g., 1-6, carbon atoms. For example, as used herein, the term "$C_{1-6}$ alkyl" refers to a linear or branched group having 1-6 carbon atoms (such as methyl, ethyl, n-propyl, isopropyl, n-butyl, isobutyl, sec-butyl, tert-butyl, n-pentyl, isopentyl, neopentyl, or n-hexyl), which is optionally substituted with one or more (e.g., 1 to 3) suitable substituents such as halogen (in which case the group may be referred to as "haloalkyl") (e.g., CH$_2$F, CHF$_2$, CF$_3$, CCl$_3$, C$_2$F$_5$, C$_2$Cl$_5$, CH$_2$CF$_3$, CH$_2$Cl or —CH$_2$CH$_2$CF$_3$ etc.). The term "$C_{1-4}$ alkyl" refers to a linear or branched aliphatic hydrocarbon chain having 1-4 carbon atoms (i.e., methyl, ethyl, n-propyl, isopropyl, n-butyl, isobutyl, sec-butyl or tert-butyl).

As used herein, the term "alkenyl" refers to a linear or branched monovalent hydrocarbyl having a double bond and 2-6 carbon atoms ("$C_{2-6}$ alkenyl"). The alkenyl is e.g., vinyl, 1-propenyl, 2-propenyl, 2-butenyl, 3-butenyl, 2-pentenyl, 3-pentenyl, 4-pentenyl, 2-hexenyl, 3-hexenyl, 4-hexenyl, 5-hexenyl, 2-methyl-2-propenyl and 4-methyl-3-pentenyl. When the compound of the present invention contains an alkenylene group, the compound may exist as the pure E (entgegen) form, the pure Z (zusammen) form, or any mixture thereof.

As used herein, the term "alkynyl" refers to a monovalent hydrocarbyl containing one or more triple bond, and preferably having 2, 3, 4, 5 or 6 carbon atoms, e.g., ethynyl or propynyl.

As used herein, the term "cycloalkyl" refers to a saturated monocyclic or polycyclic (e.g., bicyclic) hydrocarbon ring (e.g., monocyclic, such as cyclopropyl, cyclobutyl, cyclopentyl, cyclohexyl, cycloheptyl, cyclooctyl, or cyclononyl, or bicyclic, including spiro, fused or bridged cyclic system (such as bicyclo[1.1.1]pentyl, bicyclo[2.2.1]heptyl, bicyclo[3.21]octyl or bicyclo[5.2.0]nonyl, or decahydronaphthalene etc.)), which is optionally substituted with one or more (e.g., 1 to 3) suitable substituents. The cycloalkyl has 3 to 15 carbon atoms. For example, the term "$C_{3-6}$ cycloalkyl" refers to a saturated monocyclic or polycyclic (e.g., bicyclic) hydrocarbon ring having 3 to 6 ring forming carbon atoms (e.g., cyclopropyl, cyclobutyl, cyclopentyl, or cyclohexyl), which is optionally substituted with one or more (e.g., 1 to 3) suitable substituents, e.g., methyl substituted cyclopropyl.

As used herein, the terms "cyclic hydrocarbylene", "cyclic hydrocarbyl" and "hydrocarbon ring" refer to a saturated (i.e., "cycloalkylene" and "cycloalkyl") or unsaturated (i.e., having one or more double and/or triple bonds in the ring) monocyclic or polycyclic hydrocarbon ring having e.g., 3-10 (suitably having 3-8, and more suitably having 3-6) ring carbon atoms, including but not limited to cyclopropyl(ene) (ring), cyclobutyl(ene) (ring), cyclopentyl(ene) (ring), cyclohexyl(ene) (ring), cycloheptyl(ene) (ring), cyclooctyl(ene) (ring), cyclononyl(ene) (ring), cyclohexenyl(ene) (ring), and the like.

As used herein, the terms "heterocyclyl", "heterocyclylene" and "heterocycle" refer to a saturated (i.e., heterocycloalkyl) or partially unsaturated (i.e., having one or more double and/or triple bonds in the ring) cyclic group having e.g., 3-10 (suitably having 3-8, and more suitably having 3-6) ring atoms, wherein at least one ring atom is a heteroatom selected from the group consisting of N, O and S, and the remaining ring atoms are C. For example, "3- to 10-membered heterocyclyl(ene)" of "3- to 10-membered heterocycle" refers to saturated or partially unsaturated heterocyclyl(ene) or heterocycle having 2-9 (e.g., 2, 3, 4, 5, 6, 7, 8 or 9) ring carbon atoms and one or more (e.g., 1, 2, 3, or 4) heteroatoms independently selected from the group consisting of N, O and S. Examples of heterocyclylene, heterocyclyl and heterocycle include, but are not limited to oxiranyl(ene), aziridinyl(ene), azetidinyl(ene), oxetanyl(ene), tetrahydrofuranyl(ene), dioxolinyl(ene), pyrrolidinyl(ene), pyrrolidonyl(ene), imidazolidinyl(ene), pyrazolidinyl(ene), pyrrolinyl(ene), tetrahydropyranyl(ene), piperidinyl(ene), morpholinyl(ene), dithianyl(ene), thiomorpholinyl(ene), piperazinyl(ene) or trithianyl(ene). Said group also encompasses a bicyclic system, including a spiro, fused, or bridged system (e.g., 8-azaspiro[4.5]decane, 3,9-diazaspiro[5.5]undecane, 2-azabicyclo[2.2.2]octane, etc.). Heterocyclylene, heterocyclyl and heterocycle may optionally be substituted with one or more (e.g., 1, 2, 3 or 4) suitable substituents.

As used herein, the terms "aryl(ene)" and "aromatic ring" refer to an all-carbon monocyclic or fused-ring polycyclic aromatic group having a conjugated π electron system. For example, as used herein, the terms "$C_{6-10}$ aryl(ene)" and "$C_{6-10}$ aromatic ring" refer to an aromatic group containing 6 to 10 carbon atoms, such as phenyl(ene) (benzene ring) or naphthyl(ene) (naphthalene ring). Aryl(ene) or aromatic ring is optionally substituted with one or more (such as 1 to 3) suitable substituents (e.g., halogen, —OH, —CN, —NO$_2$, and $C_{1-6}$ alkyl, etc.).

As used herein, the terms "heteroaryl(ene)" and "heteroaromatic ring" refer to a monocyclic, bicyclic or tricyclic aromatic ring system having 5, 6, 8, 9, 10, 11, 12, 13 or 14 ring atoms, particularly 1 or 2 or 3 or 4 or 5 or 6 or 9 or 10 carbon atoms, and containing at least one heteroatom (such as O, N, or S), which can be same to different. Moreover, in each case, it can be benzo-fused. In particular, "heteroaryl(ene)" or "heteroaromatic ring" is selected from the group consisting of thienyl(ene), furyl(ene), pyrrolyl(ene), oxazolyl(ene), thiazolyl(ene), imidazolyl(ene), pyrazolyl(ene), isoxazolyl(ene), isothiazolyl(ene), oxadiazolyl(ene), triazolyl(ene), thiadiazolyl(ene) etc., and benzo derivatives thereof; or pyridinyl(ene), pyridazinyl(ene), pyrimidinyl(ene), pyrazinyl(ene), triazinyl(ene), etc., and benzo derivatives thereof.

As used herein, the term "aralkyl" preferably means aryl or heteroaryl substituted alkyl, wherein aryl, heteroaryl and alkyl are as defined herein. Normally, the aryl group may have 6-14 carbon atoms, the heteroaryl group may have 5-14 ring atoms, and the alkyl group may have 1-6 carbon atoms. Exemplary aralkyl group includes, but is not limited to, benzyl, phenylethyl, phenylpropyl, phenylbutyl.

As used herein, the term "halo" or "halogen" are defined to include F, Cl, Br, or I.

As used herein, the term "nitrogen containing heterocycle" refers to a saturated or unsaturated monocyclic or bicyclic group having 2, 3, 4, 5, 6, 7, 8, 9, 10, 11, 12 or 13 carbon atoms and at least one nitrogen atom in the ring, which may further optionally comprise one or more (e.g., one, two, three or four) ring members selected from the group consisting of N, O, C=O, S, S=O and S(=O)$_2$. The nitrogen containing heterocycle is attached to the rest of the molecule through the nitrogen atom and any other ring atom in said nitrogen containing heterocycle. The nitrogen containing heterocycle is optionally benzo-fused, and is preferably attached to the rest of the molecule through the nitrogen atom in said nitrogen containing heterocycle and any carbon atom in the fused benzene ring.

The term "substituted" means that one or more (e.g., one, two, three, or four) hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds.

If a substituent is described as being "optionally substituted," the substituent may be either (1) not substituted, or (2) substituted. If a carbon of a substituent is described as being optionally substituted with one or more of a list of substituents, one or more of the hydrogens on the carbon (to the extent there are any) may separately and/or together be replaced with an independently selected optional substituent. If a nitrogen of a substituent is described as being optionally substituted with one or more of a list of substituents, one or more of the hydrogens on the nitrogen (to the extent there are any) may each be replaced with an independently selected optional substituent.

If substituents are described as being "independently selected" from a group, each substituent is selected independent of the other(s). Each substituent therefore may be identical to or different from the other substituent(s).

As used herein, the term "one or more" means one or more than one (e.g., 2, 3, 4, 5 or 10) as reasonable.

As used herein, unless specified, the point of attachment of a substituent can be from any suitable position of the substituent.

When a bond to a substituent is shown to cross a bond connecting two atoms in a ring, then such substituent may be bonded to any of the ring-forming atoms in that ring that are substitutable.

The present invention also includes all pharmaceutically acceptable isotopically labeled compounds, which are identical to those of the present invention except that one or more atoms are replaced by an atom having the same atomic number, but an atomic mass or mass number different from the atomic mass or mass number which predominates in nature. Examples of isotopes suitable for inclusion in the compound of the present invention include, but are not limited to, isotopes of hydrogen, such as $^2$H, $^3$H; carbon, such as $^{11}$C, $^{13}$C, and $^{14}$C; chlorine, such as $^{36}$Cl; fluorine, such as $^{18}$F; iodine, such as $^{123}$I and $^{125}$I; nitrogen, such as $^{13}$N and $^{15}$N; oxygen, such as $^{15}$O, $^{17}$O, and $^{18}$O; phosphorus, such as $^{32}$P; and sulfur, such as $^{35}$S. Certain isotopically labeled compounds of the present invention, for example those incorporating a radioactive isotope, are useful in drug and/or substrate tissue distribution studies (e.g., assays). The radioactive isotopes tritium, i.e., $^3$H, and carbon-14, i.e., $^{14}$C, are particularly useful for this purpose in view of their ease of incorporation and ready means of detection. Substitution with positron-emitting isotopes, such as $^{11}$C, $^{18}$F, $^{15}$O and $^{13}$N, can be useful in positron emission tomography (PET) studies for examining substrate receptor occupancy. Isotopically labeled compounds of the present invention can generally be prepared by processes analogous to those described in the accompanying Schemes and/or in the Examples and Preparations, by using an appropriate isotopically labeled reagent in place of the non-labeled reagent previously employed. Pharmaceutically acceptable solvates in accordance with the invention include those wherein the solvent of crystallization may be isotopically substituted, e.g., $D_2O$, acetone-$d_6$, or DMSO-$d_6$.

The term "stereoisomer" refers to isomers with at least one asymmetric center. A compound having one or more (e.g., one, two, three or four) asymmetric centers can give rise to a racemic mixture, single enantiomer, diastereomer mixture and individual diastereomer. Certain individual molecules may exist as geometric isomers (cis/trans). Similarly, the compound of the present invention may exist as a mixture of two or more structurally different forms in rapid equilibrium (generally referred to as tautomer). Typical examples of a tautomer include a keto-enol tautomer, phenol-keto tautomer, nitroso-oxime tautomer, imine-enamine tautomer and the like. It is to be understood that all such isomers and mixtures thereof in any proportion (such as 60%, 65%, 70%, 75%, 80%, 85%, 90%, 95%, 96%, 97%, 98%, and 99%) are encompassed within the scope of the present invention.

The chemical bonds of the compound of the present invention may be depicted herein using a solid line (———) a solid wedge (⬛—), or a dotted wedge (⫶⫶⫶⫶) The use of a solid line to depict bonds to asymmetric carbon atoms is meant to indicate that all possible stereoisomers (e.g., specific enantiomers, racemic mixtures, etc.) at that carbon atom are included. The use of either a solid or dotted wedge to depict bonds to asymmetric carbon atoms is meant to indicate that the stereoisomer shown is present. When present in racemic compounds, solid and dotted wedges are used to define relative stereochemistry, rather than absolute stereochemistry. Unless stated otherwise, it is intended that the compound of the present invention can exist as stereoisomers, which include cis and trans isomers, optical isomers such as R and S enantiomers, diastereomers, geometric isomers, rotational isomers, conformational isomers, atropisomers, and mixtures thereof. The compound of the present invention may exhibit more than one type of isomerism, and consist of mixtures thereof (such as racemates and diastereomeric pairs).

The present invention includes all possible crystalline forms or polymorphs of the compound of the present invention, either as a single polymorph, or as a mixture of more than one polymorphs, in any ratio.

It also should be understood that, certain compounds of the present invention can be used for the treatment in a free form, or where appropriate, in a form of a pharmaceutically acceptable derivative. In the present invention, the pharmaceutically acceptable derivative includes, but is not limited to a pharmaceutically acceptable salt, ester, solvate, N-oxide, metabolite or prodrug, which can directly or indirectly provide the compound of the present invention or a metabolite or residue thereof after being administered to a patient in need thereof. Therefore, "the compound of the present invention" mentioned herein also means to encompass various derivative forms of the compound as mentioned above.

A pharmaceutically acceptable salt of the compound of the present invention includes an acid addition salt and a base addition salt thereof.

A suitable acid addition salt is formed from an acid which forms a pharmaceutically acceptable salt. Specific examples include acetate, adipate, aspartate, benzoate, besylate, bicarbonate/carbonate, bisulfate/sulfate, borate, camphorsulfonate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulfate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts.

A suitable base addition salt is formed from a base which forms a pharmaceutically acceptable salt. Specific examples include aluminum, arginine, benzathine, calcium, choline, diethylamine, diolamine, glycine, lysine, magnesium, meglumine, olamine, potassium, sodium, tromethamine and zinc salts.

For a review on suitable salts, see "Handbook of Pharmaceutical Salts: Properties, Selection, and Use" by Stahl and Wermuth (Wiley-VCH, 2002). The method for preparing a pharmaceutically acceptable salt of the compound of the present invention is known to a person skilled in the art.

As used herein, the term "ester" refers to those derived from the compounds of the various formulae in the present application, which include physiologically-hydrolyzable esters (which may be hydrolyzed under physiological conditions to release the compounds of the present invention in the form of free acids or alcohols). The compound of the present invention itself may be an ester as well.

The compound of the present invention can exist as a solvate (preferably a hydrate), wherein the compound of the present invention contains a polar solvent, in particular water, methanol or ethanol for example, as a structural element of the crystal lattice of the compound. The amount of the polar solvent, in particular water, may exist in a stoichiometric or non-stoichiometric ratio.

As can be appreciated by a person skilled in the art, not all nitrogen containing heterocycles can form N-oxides since the nitrogen requires an available lone-pair electron for oxidation to the oxide; a person skilled in the art will recognize those nitrogen containing heterocycles which can form N-oxides. A person skilled in the art will also recognize that tertiary amines can form N-oxides. Synthetic methods for the preparation of N-oxides of heterocycles and tertiary amines are well known to a person skilled in the art, and they include the oxidation of heterocycles and tertiary amines with peroxy acids such as peracetic acid and m-chloroperbenzoic acid (MCPBA), hydrogen peroxide, alkyl hydroperoxides such as tert-butyl hydroperoxide, sodium perborate, and dioxiranes such as dimethyldioxirane. These methods for the preparation of N-oxides have been extensively described and reviewed in literatures, see e.g., T. L. Gilchrist, *Comprehensive Organic Synthesis*, vol. 7, pp 748-750; A. R. Katritzky and A. J. Boulton, Eds., Academic Press; and G. W. H. Cheeseman and E. S. G. Werstiuk, *Advances in Heterocyclic Chemistry*, vol. 22, pp 390-392, A. R. Katritzky and A. J. Boulton, Eds., Academic Press.

The metabolite of the compound of the present invention, namely a substance formed in vivo upon administration of the compound of the present invention, is also included within the scope of the present invention. Such a product may result e.g., from the oxidation, reduction, hydrolysis, amidation, de-amidation, esterification, enzymolysis, and the like, of the administered compound. Accordingly, the present invention encompasses the metabolite of the compound of the present invention, including a compound produced by a method comprising contacting the compound of the present invention with a mammal for a period of time sufficient to result in a metabolic product thereof.

Also within the scope of the present invention is a prodrug of the compound of the invention, which is certain derivative of the compound of the invention that may have little or no pharmacological activity itself, but can, when administered into or onto the body, be converted into the compound of the invention having the desired activity, for example, by hydrolytic cleavage. In general, such prodrug will be a functional derivative of the compound which is readily converted in vivo into the compound with desired therapeutic activity. Further information on the use of the prodrug may be found in "Pro-drugs as Novel Delivery Systems, Vol. 14, ACS Symposium Series (T. Higuchi and V. Stella). The prodrug in accordance with the invention can, for example, be produced by replacing appropriate functionalities present in the compound of the present invention with certain moieties known to those skilled in the art as "pro-moieties" as described, for example, in "Design of Prodrugs" by H. Bundgaard (Elsevier, 1985).

The present invention further encompasses the compound of the present invention having a protecting group. During any of the processes for preparation of the compound of the present invention, it may be necessary and/or desirable to protect sensitive or reactive groups on any of the molecules concerned, thereby resulting in the chemically protected form of the compound of the present invention. This may be achieved by means of conventional protecting groups, e.g., those described in T.W. Greene & P.G.M. Wuts, Protective Groups in Organic Synthesis, John Wiley & Sons, 1991, which is incorporated herein by reference. The protecting groups may be removed at a convenient subsequent stage using methods known from the art.

The term "about" refers to a range within ±10%, preferably within ±5%, and more preferably within ±2% of the specified value.

Compound

In some embodiments, the present invention provides a compound or a pharmaceutically acceptable salt, ester, stereoisomer, polymorph, solvate, N-oxide, isotopically labeled compound, metabolite or prodrug thereof, wherein the compound has the structure of Formula (I):

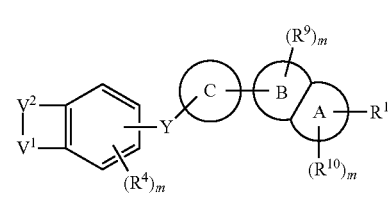

Formula (I)

wherein:
$V^1$ is selected from the group consisting of $-CR^2=N-$, $-N=CR^2-$, $-NR^3C(=O)-$ and $-C(=O)NR^3-$;
$V^2$ is selected from the group consisting of $-CR^2=N-$, $-N=CR^2-$, $-(CR^2R^{2'})_n-$ and $-(CR^2=CR^{2'})_n-$;
Y is selected from the group consisting of a direct bond, $C(=O)$, O, $S(=O)_i$ and NR;
R is selected from the group consisting of H, $C_{1-6}$ alkyl, $C_{2-6}$ alkenyl, $C_{2-6}$ alkynyl, saturated or partially unsaturated $C_{3-10}$ cyclic hydrocarbyl, saturated or partially unsaturated 3-10-membered heterocyclyl, $C_{6-10}$ aryl, 5-14-membered heteroaryl and $C_{6-12}$ aralkyl, and at most 2 ring members in the cyclic hydrocarbyl and heterocyclyl are $C(=O)$;
ring A and ring B are each independently selected from the group consisting of saturated or partially unsaturated $C_{3-10}$ hydrocarbon ring, saturated or partially unsaturated 3-10-membered heterocycle, $C_{6-10}$ aromatic ring and 5-14-membered heteroaromatic ring, and at most 2 ring members in the hydrocarbon ring and heterocycle are $C(=O)$;
ring C is

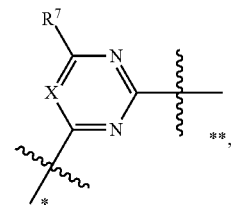

which is attached to Y at either of the two positions labeled * or **, and is attached to ring B at the other position;
X is selected from the group consisting of $CR^8$ and N;
$R^1$ is selected from the group consisting of $-C(=O)R^{1a}$, $-C(=O)OR^{1a}$ and $-C(=O)NR^{1a}R^{1b}$;
$R^{1a}$ and $R^{1b}$ are each independently selected from the group consisting of H, halogen, amino, cyano, nitro, $C_{1-6}$ alkyl, $C_{2-6}$ alkenyl, $C_{2-6}$ alkynyl, $C_{3-10}$ cyclic hydrocarbyl, 3-10-membered heterocyclyl, $C_{6-10}$ aryl, 5-14-membered heteroaryl, $C_{6-12}$ aralkyl, $-C(=O)R^5$, $-OC(=O)R^5$, $-C(=O)OR^5$, $-SR^5$, $-S(=O)R^5$, $-S(=O)_2R^5$, $-S(=O)_2NR^5R^6$, $-NR^5R^6$, $-C(=O)NR^5R^6$, $-NR^5-C(=O)R^6$, $-NR^5-C(=O)OR^6$, $-NR^5-S(=O)_2-R^6$, $-NR^5-C(=O)-NR^5R^6$, $-C_{1-6}$ alkylene-$NR^5R^6$, $-C_{1-6}$ alkylene-$OR^5$ and $-O-C_{1-6}$ alkylene-$NR^5R^6$; alternatively, $R^{1a}$ and $R^{1b}$ together with the atom to which they are attached form a 3-12-membered heterocycle or heteroaromatic ring;
$R^2$, $R^{2'}$, $R^3$, $R^4$, $R^7$, $R^8$, $R^9$ and $R^{10}$, at each occurrence, are each independently selected from the group consisting of H, halogen, amino, cyano, nitro, $C_{1-6}$ alkyl, $C_{2-6}$ alkenyl, $C_{2-6}$ alkynyl, $C_{3-10}$ cyclic hydrocarbyl, 3-10-membered heterocyclyl, $C_{6-10}$ aryl, 5-14-membered heteroaryl, $C_{6-12}$ aralkyl, $-C(=O)R^5$, $-OC(=O)R^5$, $-C(=O)OR^5$, $-SR^5$, $-S(=O)R^5$, $-S(=O)_2R^5$, $-S(=O)_2NR^5R^6$, $-NR^5R^6$, $-C(=O)NR^5R^6$, $-NR^5-C(=O)R^6$, $-NR^5-C(=O)OR^6$, $-NR^5-S(=O)_2-R^6$, $-NR^5-C(=O)-NR^5R^6$, $-C_{1-6}$ alkylene-$NR^5R^6$, $-C_{1-6}$ alkylene-$O(P=O)(OH)_2$ and $-O-C_{1-6}$ alkylene-$NR^5R^6$; alternatively, $R^7$ and $R^8$ together with the group to which they are attached form a $C_{6-10}$ aromatic ring or 5-14-membered heteroaromatic ring;

the alkyl, alkylene, alkenyl, alkenylene, alkynyl, cyclic hydrocarbyl, hydrocarbon ring, heterocyclyl, heterocycle, aryl, aromatic ring, heteroaryl, heteroaromatic ring and aralkyl, at each occurrence, are each optionally substituted with one or more substituents independently selected from the group consisting of: halogen, hydroxyl, oxo, amino, cyano, nitro, $C_{1-6}$ alkyl, $C_{2-6}$ alkenyl, $C_{2-6}$ alkynyl, $C_{3-6}$ cyclic hydrocarbyl, 3-10-membered heterocyclyl, $C_{6-10}$ aryl, 5-14-membered heteroaryl, $C_{6-12}$ aralkyl, $=N-OR^5$, $-C(=NH)NH_2$, $-C(=O)R^5$, $-OC(=O)R^5$, $-C(=O)OR^5$, $-SR^5$, $-S(=O)R^5$, $-S(=O)_2R^5$, $-S(=O)_2NR^5R^6$, $-NR^5R^6$, $-C(=O)NR^5R^6$, $-NR^5-C(=O)R^6$, $-NR^5-C(=O)OR^6$, $-NR^5-S(=O)_2-R^6$, $-NR^5-C(=O)-NR^5R^6$, $-C_{1-6}$ alkylene-$NR^5R^6$ and $-O-C_{1-6}$ alkylene-$NR^5R^6$, and the alkyl, alkylene, alkenyl, alkynyl, cyclic hydrocarbyl, heterocyclyl, aryl, heteroaryl and aralkyl are further optionally substituted with one or more substituents independently selected from the group consisting of: halogen, hydroxyl, oxo, amino, cyano, nitro, $C_{1-6}$ alkyl, $C_{3-6}$ cyclic hydrocarbyl, 3-10-membered heterocyclyl, $C_{6-10}$ aryl, 5-14-membered heteroaryl and $C_{6-12}$ aralkyl;

$R^5$ and $R^6$, at each occurrence, are each independently selected from the group consisting of H, $C_{1-6}$ alkyl, $C_{3-10}$ cyclic hydrocarbyl, 3-10-membered heterocyclyl, $C_{6-10}$ aryl, 5-14-membered heteroaryl and $C_{6-12}$ aralkyl; alternatively, when $R^5$ and $R^6$ are attached to a same nitrogen atom, $R^5$ and $R^6$ together with the atom to which they are attached optionally form a 3-12-membered heterocycle or heteroaromatic ring;

m, at each occurrence, is each independently an integer of 0, 1, 2 or 3;

n is an integer of 0, 1, 2, 3 or 4; and i is an integer of 0, 1 or 2.

In some embodiments, the present invention provides the compound or a pharmaceutically acceptable salt, ester, stereoisomer, polymorph, solvate, N-oxide, isotopically labeled compound, metabolite or prodrug thereof, wherein Y is selected from the group consisting of a direct bond, $C(=O)$, O, S, $S(=O)$, $S(=O)_2$, NH and $NCH_3$.

In some embodiments, the present invention provides the compound or a pharmaceutically acceptable salt, ester, stereoisomer, polymorph, solvate, N-oxide, isotopically labeled compound, metabolite or prodrug thereof, wherein

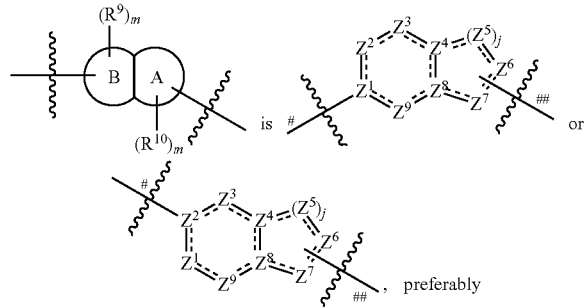

is

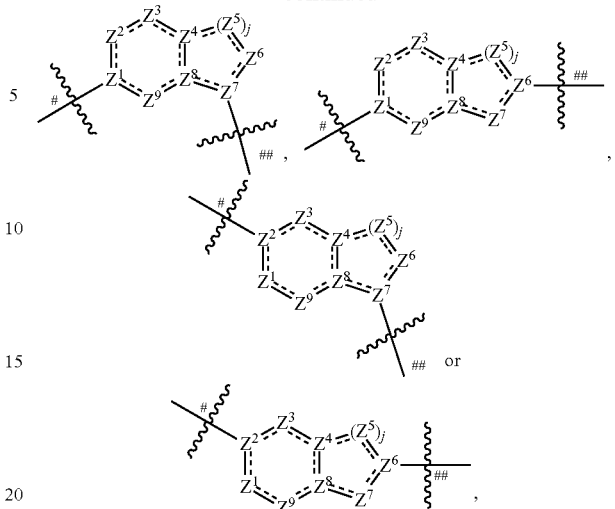

, preferably the above group is attached to ring C at either of the two positions labeled # or ##, and is attached to $R^1$ at the other position, wherein $=$ represents either a single or a double bond, and the adjacent bonds are not double bonds simultaneously;

$Z^1$, $Z^2$, $Z^3$, $Z^4$, $Z^5$, $Z^6$, $Z^7$, $Z^8$ and $Z^9$, at each occurrence, are each independently selected from the group consisting of C, $CR^9$, $C(R^9)_2$, $(C(R^{10})_2)$, $C(=O)$, N, $NR^9$, $NR^{10}$, O and S; preferably, $Z^1$, $Z^2$, $Z^3$, $Z^4$, $Z^5$, $Z^6$, $Z^7$, $Z^8$ and $Z^9$, at each occurrence, are each independently selected from the group consisting of C, CH, CF, CCl, $CCH_3$, $CH_2$, $C(CH_3)_2$, $C-OCH_3$, $C(=O)$, N, NH, $NCH_3$, $NCH_2CH_3$, $NCH(CH_3)_2$, $NCH=CH_2$, $NCH_2F$, $NCHF_2$, $NCH_2CHF_2$, $NC(=O)CH_3$, $NCH_2OH$, $NCH_2OMe$, $NCH_2CH_2OMe$, $NCH_2-O(P=O)(OH)_2$,

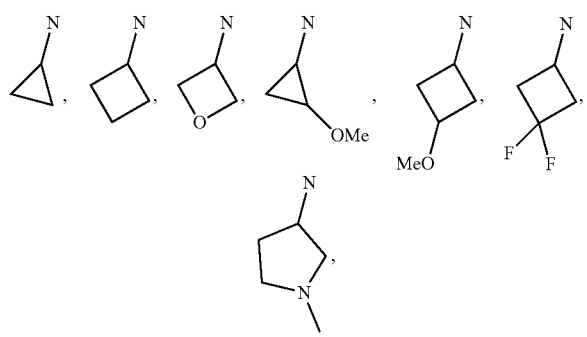

$NCH_2CH_2-N(CH_3)_2$, O and S;

j is 0, 1, 2, 3 or 4;

provided that at most two groups among $Z^1$-$Z^9$ are simultaneously $C(=O)$;

$R^9$ and $R^{10}$, at each occurrence, are each independently selected from the group consisting of halogen, methyl, ethyl, propyl, vinyl, cyclopropyl, cyclobutyl, cyclopentyl, oxetanyl, monofluoromethyl, difluoromethyl, trifluoromethyl, $-CH_2CHF_2$, acetyl, $-OCH_3$, $-CH_2OH$, $-CH_2OCH_3$, $-CH_2CH_2OCH_3$, $-CH_2-O(P=O)(OH)_2$,

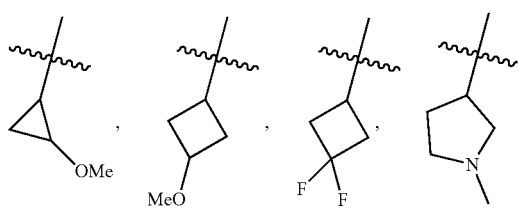

and —CH$_2$CH$_2$—N(CH$_3$)$_2$;
most preferably,

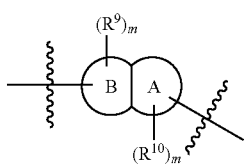

is selected from the group consisting of

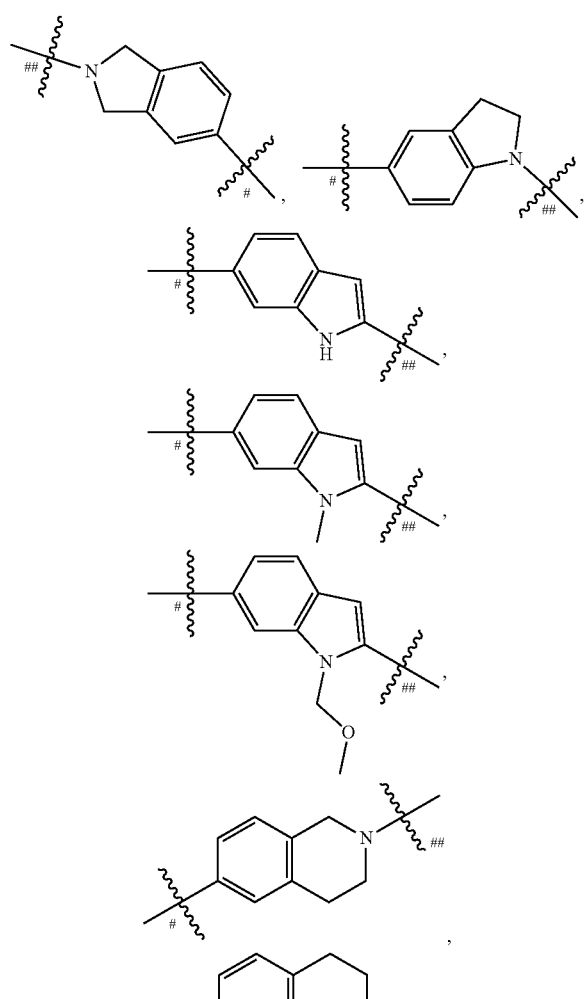

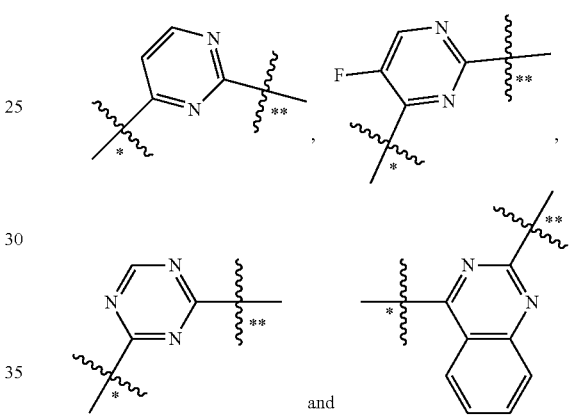

the above group is attached to ring C at either of the two positions labeled # or ##, and is attached to R$^1$ at the other position.

In some embodiments, the present invention provides the compound or a pharmaceutically acceptable salt, ester, stereoisomer, polymorph, solvate, N-oxide, isotopically labeled compound, metabolite or prodrug thereof, wherein ring C is selected from the group consisting of the above group is attached to Y at either of the two positions labeled * or **, and is attached to ring B at the other position.

In some embodiments, the present invention provides the compound or a pharmaceutically acceptable salt, ester, stereoisomer, polymorph, solvate, N-oxide, isotopically labeled compound, metabolite or prodrug thereof, wherein V' is selected from the group consisting of —CH=N—, —N=CH—, —C(NH$_2$)=N—, —N=C(NH$_2$)—, —NHC(=O)— and —C(=O)NH—.

In some embodiments, the present invention provides the compound or a pharmaceutically acceptable salt, ester, stereoisomer, polymorph, solvate, N-oxide, isotopically labeled compound, metabolite or prodrug thereof, wherein V$^2$ is selected from the group consisting of —CH=N—, —N=CH—, —CH$_2$—, —(CH$_2$)$_2$—, —(CH=CCl)—, —(CCl=CH)— and —(CH=CH)—.

In some embodiments, the present invention provides the compound or a pharmaceutically acceptable salt, ester, stereoisomer, polymorph, solvate, N-oxide, isotopically labeled compound, metabolite or prodrug thereof, wherein

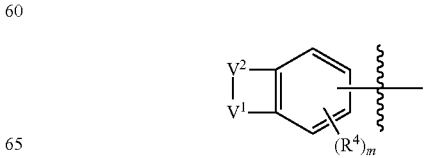

is selected from the group consisting of
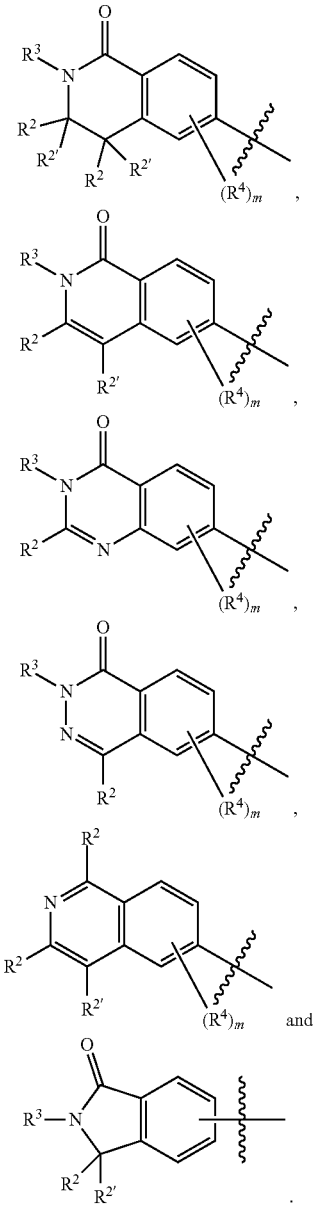
In preferred embodiments,
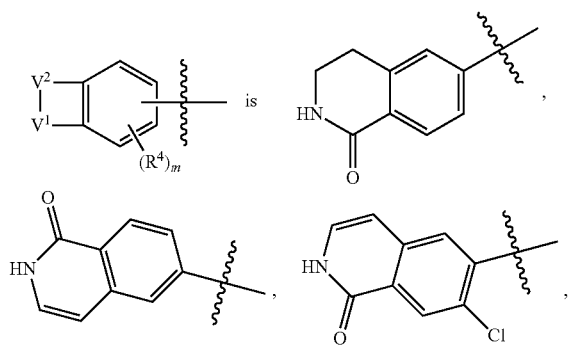
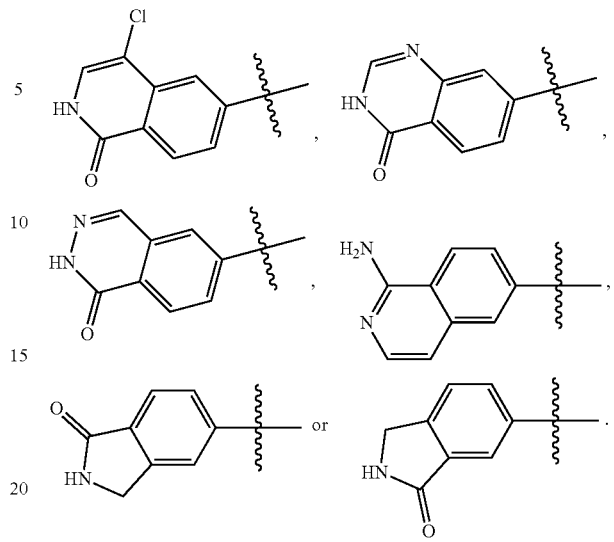
In some embodiments, the present invention provides the compound or a pharmaceutically acceptable salt, ester, stereoisomer, polymorph, solvate, N-oxide, isotopically labeled compound, metabolite or prodrug thereof, wherein $R^1$ is selected from the group consisting of
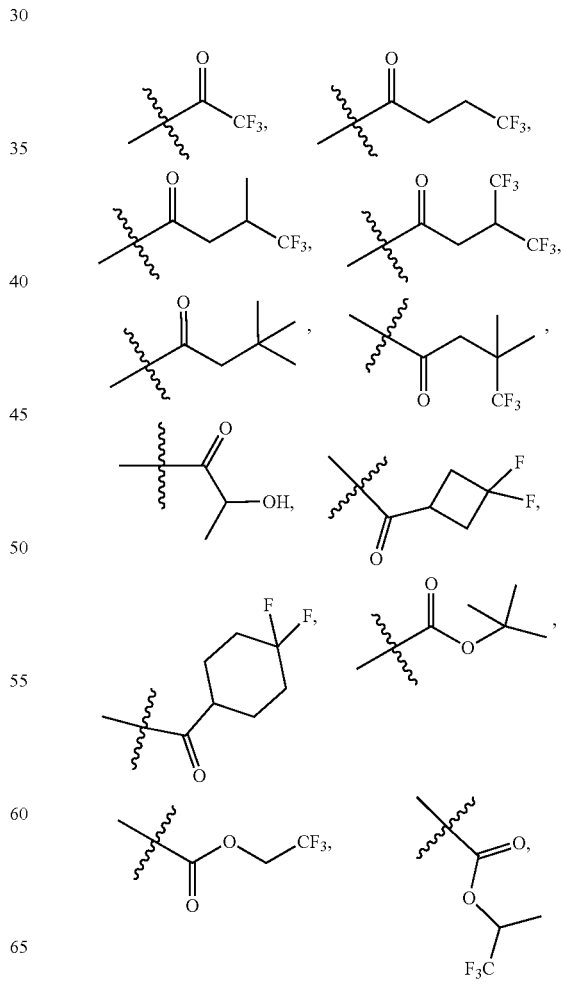

-continued

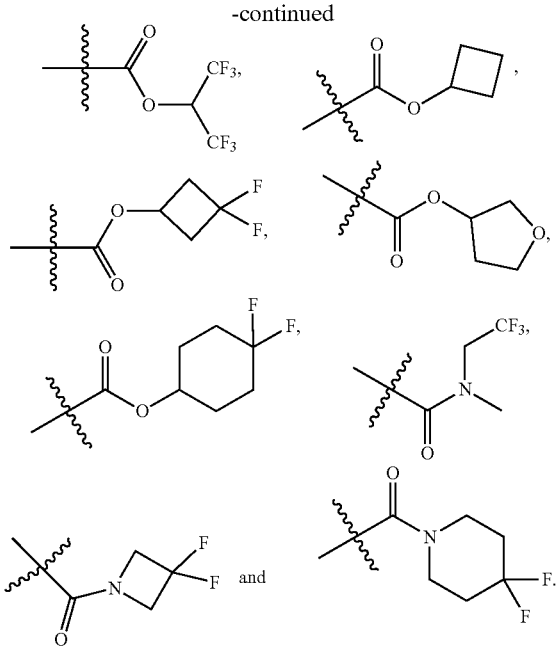

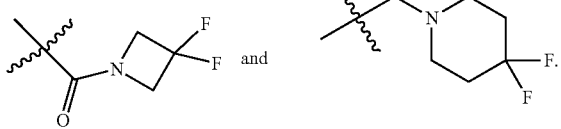

In some embodiments, the present invention provides the compound or a pharmaceutically acceptable salt, ester, stereoisomer, polymorph, solvate, N-oxide, isotopically labeled compound, metabolite or prodrug thereof, wherein the compound has the structure of any of the following formulae:

(II)

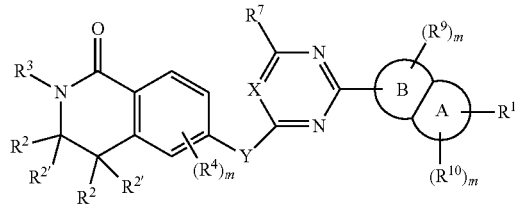

(III)

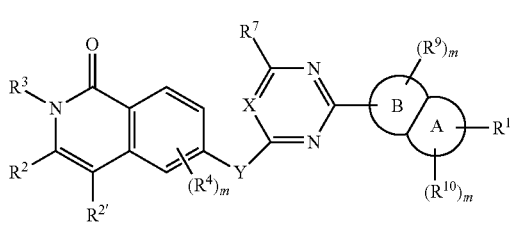

(IV)

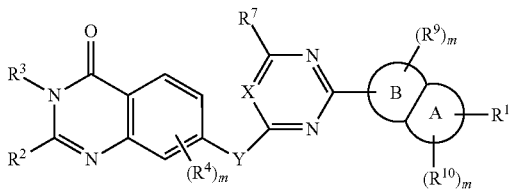

(V)

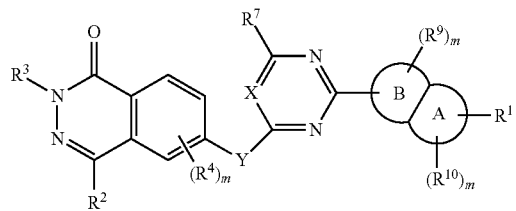

(VI)

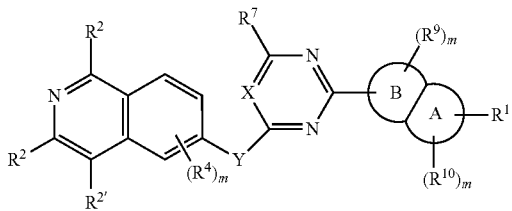

(VII)

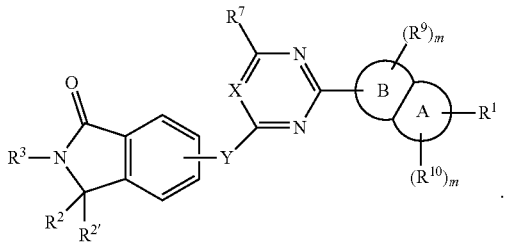

The compound obtained by any combination of the various embodiments is encompassed by the invention.

In some embodiments, the present invention provides a compound or a pharmaceutically acceptable salt, ester, stereoisomer, polymorph, solvate, N-oxide, isotopically labeled compound, metabolite or prodrug thereof, wherein the compound has the following structure:

| No. | Structure |
|---|---|
| C1. | 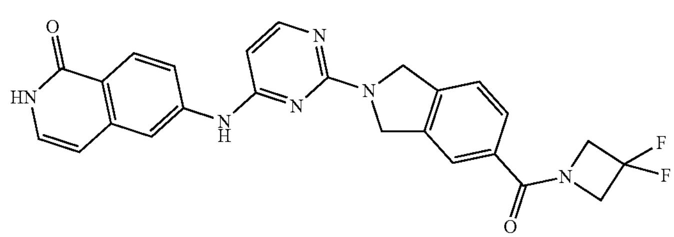 [SMILES: O=C(c1ccc2c(c1)CN(c1nccc(Nc3ccc4c(=O)[nH]ccc4c3)n1)C2)N1CC(F)(F)C1] |

-continued
| No. | Structure |
|---|---|
| C2. | 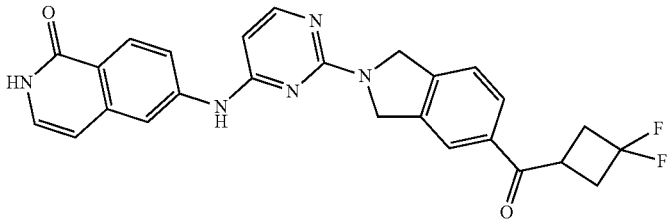 [SMILES: O=C(c1ccc2c(c1)CN(c1nccc(Nc3ccc4c(=O)[nH]ccc4c3)n1)C2)C1CC(F)(F)C1] |
| C3. | 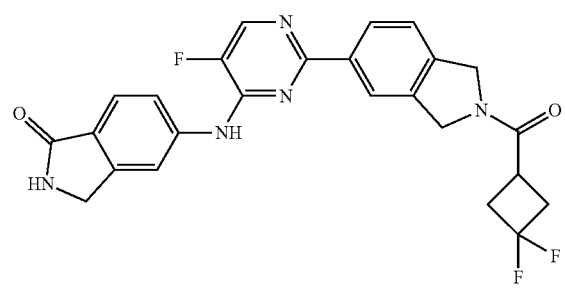 [SMILES: O=C1NCc2cc(Nc3nc(-c4ccc5c(c4)CN(C(=O)C4CC(F)(F)C4)C5)ncc3F)ccc21] |
| C4. | 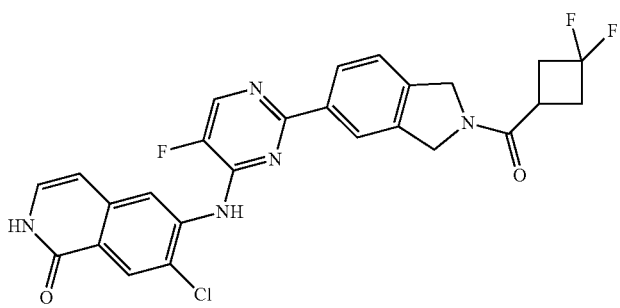 [SMILES: O=C(C1CC(F)(F)C1)N1Cc2ccc(-c3ncc(F)c(Nc4cc5cc[nH]c(=O)c5cc4Cl)n3)cc2C1] |
| C5. | 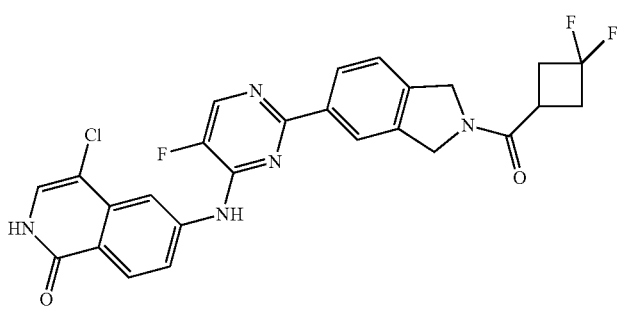 [SMILES: O=C(C1CC(F)(F)C1)N1Cc2ccc(-c3ncc(F)c(Nc4ccc5c(=O)[nH]cc(Cl)c5c4)n3)cc2C1] |
| C6. | 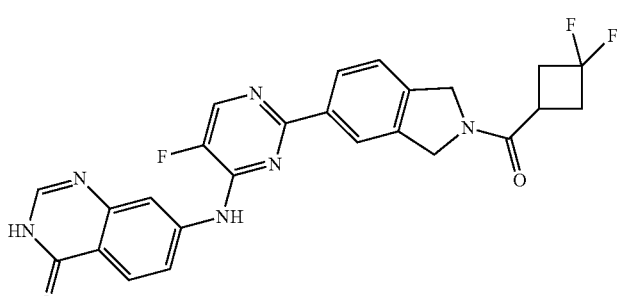 |

-continued
| No. | Structure |
|---|---|
| C7. | 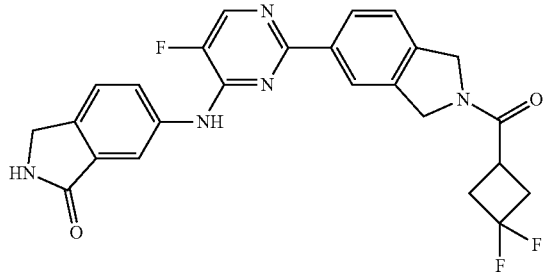 [SMILES: O=C1NCc2ccc(Nc3nc(-c4ccc5c(c4)CN(C(=O)C4CC(F)(F)C4)C5)ncc3F)cc21] |
| C8. | 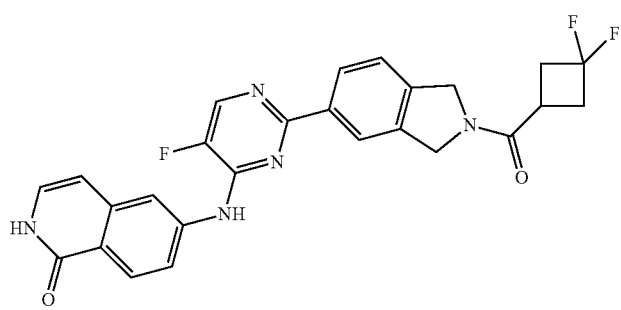 [SMILES: O=C(C1CC(F)(F)C1)N1Cc2ccc(-c3ncc(F)c(Nc4ccc5c(=O)[nH]ccc5c4)n3)cc2C1] |
| C9. | 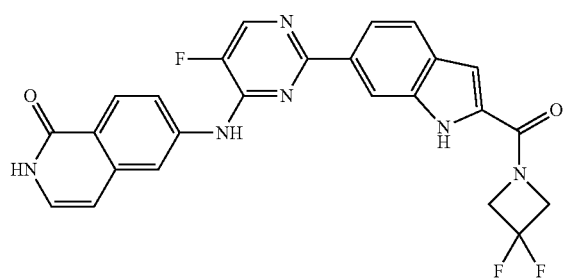 [SMILES: O=C(c1cc2ccc(-c3ncc(F)c(Nc4ccc5c(=O)[nH]ccc5c4)n3)cc2[nH]1)N1CC(F)(F)C1] |
| C10. | 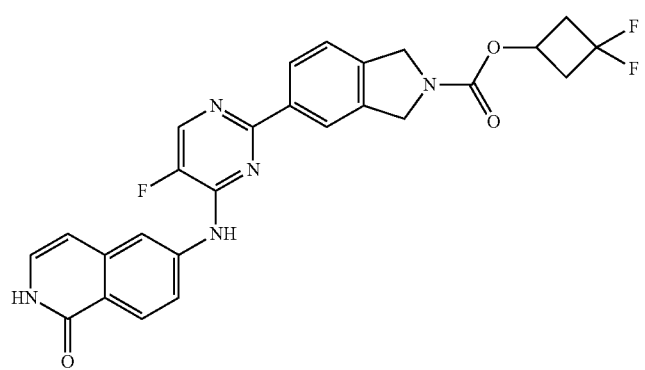 [SMILES: O=C(OC1CC(F)(F)C1)N1Cc2ccc(-c3ncc(F)c(Nc4ccc5c(=O)[nH]ccc5c4)n3)cc2C1] |
| C11. | 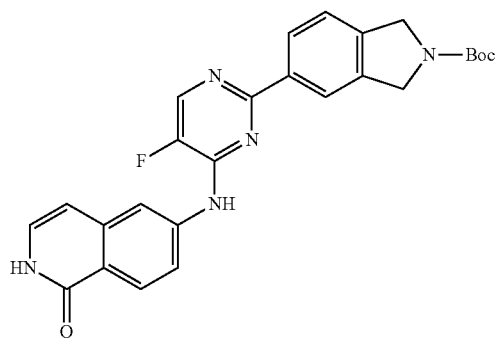 [SMILES: CC(C)(C)OC(=O)N1Cc2ccc(-c3ncc(F)c(Nc4ccc5c(=O)[nH]ccc5c4)n3)cc2C1] |

-continued

| No. | Structure |
|---|---|
| C12. | 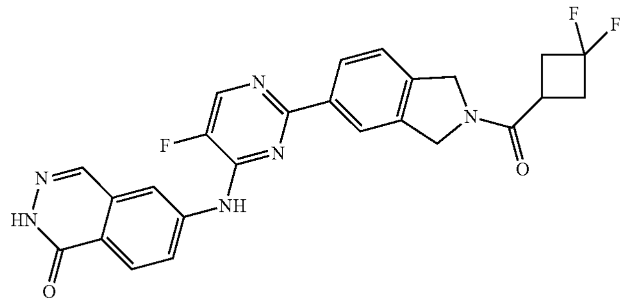 [SMILES: O=C(C1CC(F)(F)C1)N1Cc2ccc(-c3ncc(F)c(Nc4ccc5c(=O)[nH]ncc5c4)n3)cc2C1] |
| C13. | 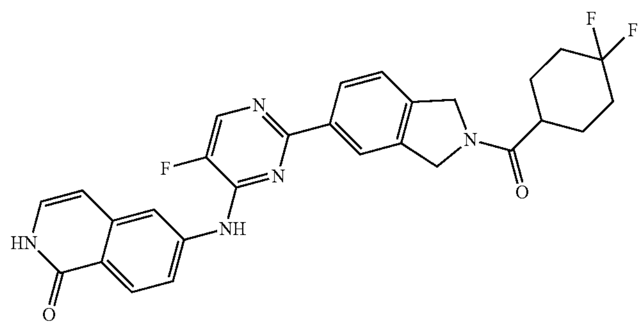 [SMILES: O=C(C1CCC(F)(F)CC1)N1Cc2ccc(-c3ncc(F)c(Nc4ccc5c(=O)[nH]ccc5c4)n3)cc2C1] |
| C14. | 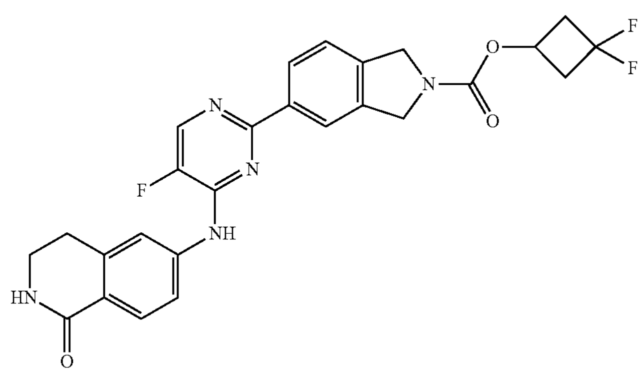 [SMILES: O=C1NCCc2cc(Nc3nc(-c4ccc5c(c4)CN(C(=O)OC4CC(F)(F)C4)C5)ncc3F)ccc21] |
| C15. | 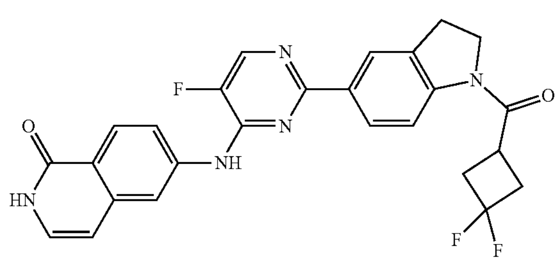 [SMILES: O=C(C1CC(F)(F)C1)N1CCc2cc(-c3ncc(F)c(Nc4ccc5c(=O)[nH]ccc5c4)n3)ccc21] |
| C16. | 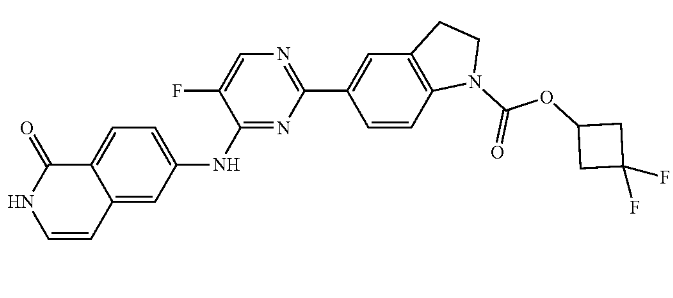 [SMILES: O=C(OC1CC(F)(F)C1)N1CCc2cc(-c3ncc(F)c(Nc4ccc5c(=O)[nH]ccc5c4)n3)ccc21] |

-continued

| No. | Structure |
|---|---|
| C17. | 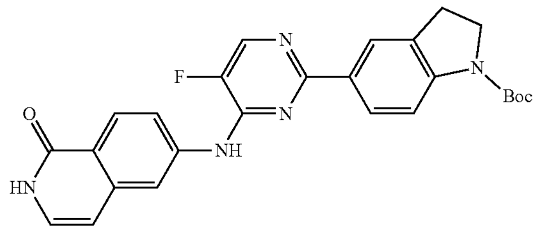 [SMILES: CC(C)(C)OC(=O)N1CCc2cc(-c3ncc(F)c(Nc4ccc5c(=O)[nH]ccc5c4)n3)ccc21] |
| C18. | 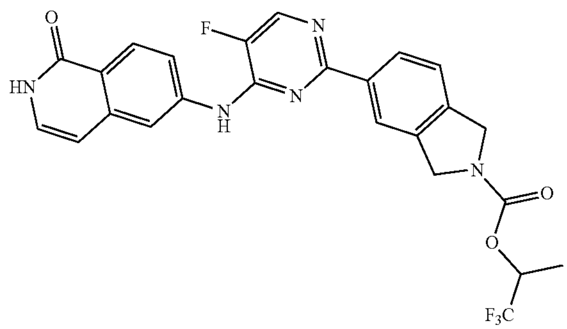 [SMILES: CC(OC(=O)N1Cc2ccc(-c3ncc(F)c(Nc4ccc5c(=O)[nH]ccc5c4)n3)cc2C1)C(F)(F)F] |
| C19. | 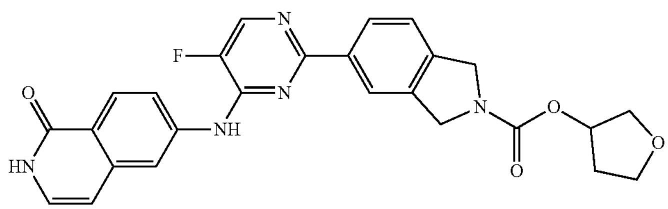 [SMILES: O=C(OC1CCOC1)N1Cc2ccc(-c3ncc(F)c(Nc4ccc5c(=O)[nH]ccc5c4)n3)cc2C1] |
| C20. | 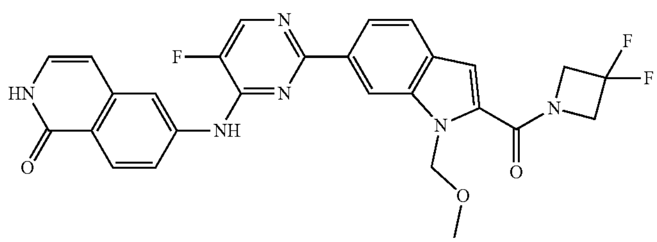 [SMILES: COCn1c(C(=O)N2CC(F)(F)C2)cc2ccc(-c3ncc(F)c(Nc4ccc5c(=O)[nH]ccc5c4)n3)cc21] |
| C21. | 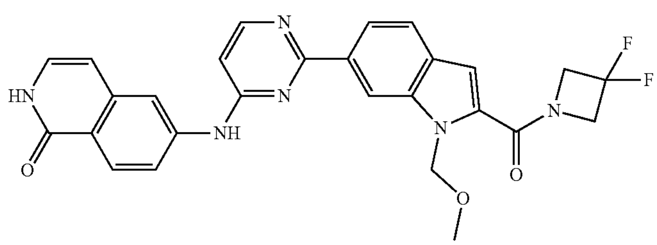 [SMILES: COCn1c(C(=O)N2CC(F)(F)C2)cc2ccc(-c3nccc(Nc4ccc5c(=O)[nH]ccc5c4)n3)cc21] |
| C22. | 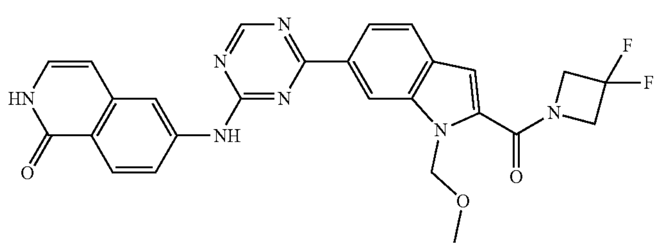 [SMILES: COCn1c(C(=O)N2CC(F)(F)C2)cc2ccc(-c3ncnc(Nc4ccc5c(=O)[nH]ccc5c4)n3)cc21] |

| No. | Structure |
|---|---|
| C23. | 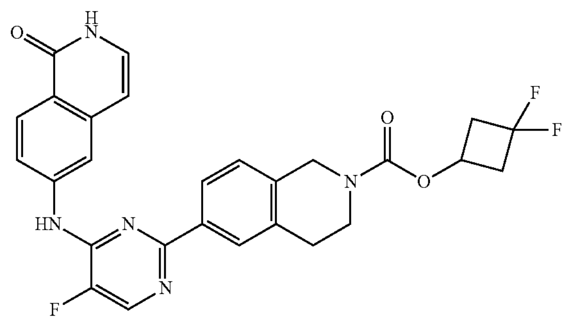 [SMILES: O=C(OC1CC(F)(F)C1)N1CCc2cc(-c3ncc(F)c(Nc4ccc5c(=O)[nH]ccc5c4)n3)ccc2C1] |
| C24. | 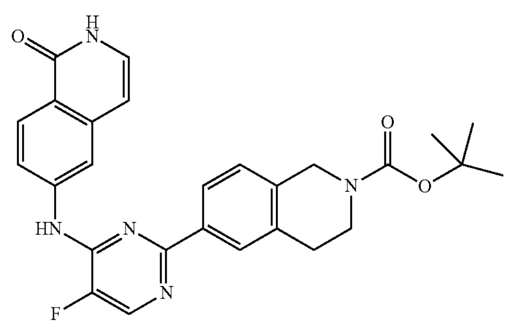 [SMILES: CC(C)(C)OC(=O)N1CCc2cc(-c3ncc(F)c(Nc4ccc5c(=O)[nH]ccc5c4)n3)ccc2C1] |
| C25. | 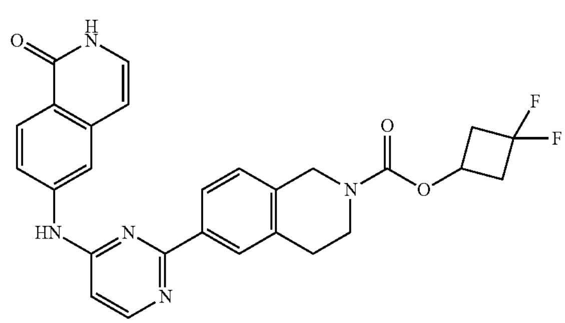 [SMILES: O=C(OC1CC(F)(F)C1)N1CCc2cc(-c3nccc(Nc4ccc5c(=O)[nH]ccc5c4)n3)ccc2C1] |
| C26. | 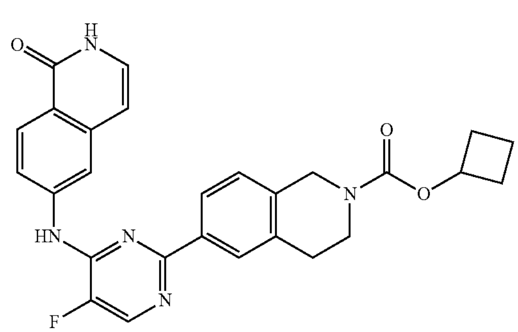 [SMILES: O=C(OC1CCC1)N1CCc2cc(-c3ncc(F)c(Nc4ccc5c(=O)[nH]ccc5c4)n3)ccc2C1] |

| No. | Structure |
|---|---|
| C27. | 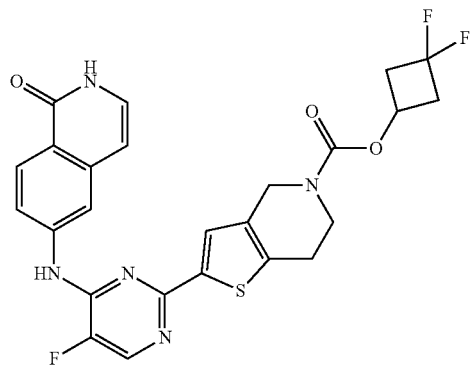 [SMILES: O=C(OC1CC(F)(F)C1)N1CCc2sc(-c3ncc(F)c(Nc4ccc5c(=O)[nH]ccc5c4)n3)cc2C1] |
| C28. | 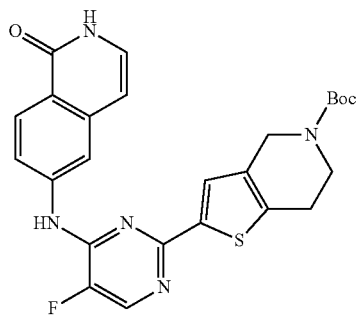 [SMILES: CC(C)(C)OC(=O)N1CCc2sc(-c3ncc(F)c(Nc4ccc5c(=O)[nH]ccc5c4)n3)cc2C1] |
| C29. | 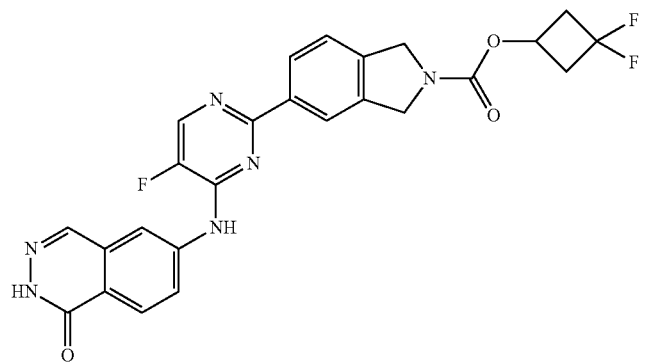 [SMILES: O=C(OC1CC(F)(F)C1)N1Cc2ccc(-c3ncc(F)c(Nc4ccc5c(=O)[nH]ncc5c4)n3)cc2C1] |
| C30. | 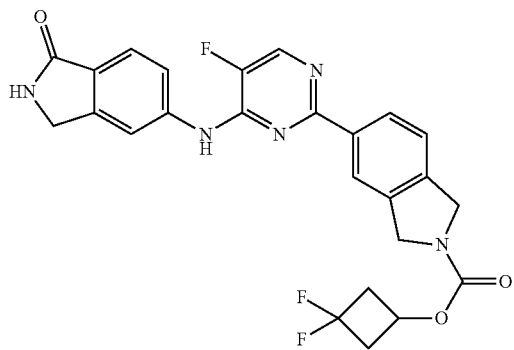 [SMILES: O=C1NCc2cc(Nc3nc(-c4ccc5c(c4)CN(C(=O)OC4CC(F)(F)C4)C5)ncc3F)ccc21] |

-continued
| No. | Structure |
|---|---|
| C31. | 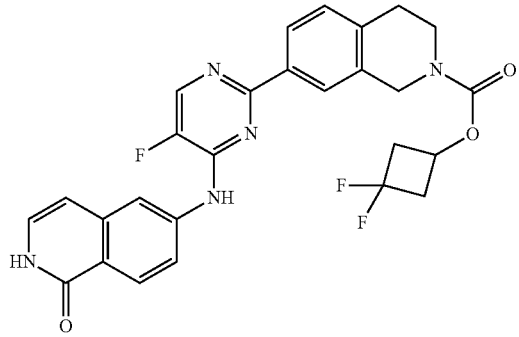 [SMILES: O=C(OC1CC(F)(F)C1)N1CCc2ccc(-c3ncc(F)c(Nc4ccc5c(=O)[nH]ccc5c4)n3)cc2C1] |
| C32. | 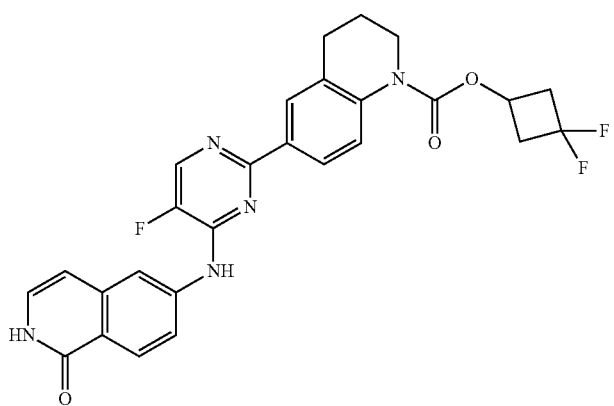 [SMILES: O=C(OC1CC(F)(F)C1)N1CCCc2cc(-c3ncc(F)c(Nc4ccc5c(=O)[nH]ccc5c4)n3)ccc21] |
| C33. | 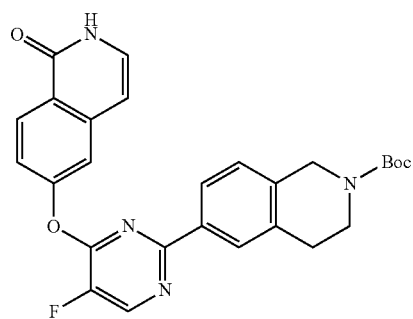 [SMILES: CC(C)(C)OC(=O)N1CCc2cc(-c3ncc(F)c(Oc4ccc5c(=O)[nH]ccc5c4)n3)ccc2C1] |
| C34. | 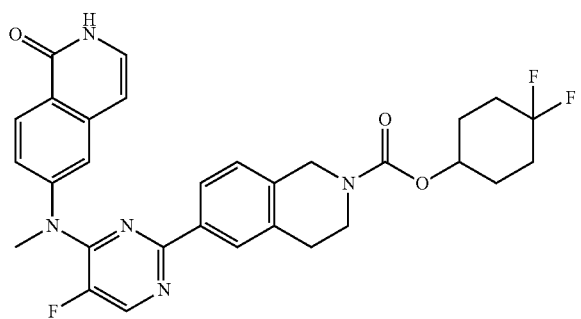 [SMILES: CN(c1ccc2c(=O)[nH]ccc2c1)c1nc(-c2ccc3c(c2)CCN(C(=O)OC2CCC(F)(F)CC2)C3)ncc1F] |

-continued
| No. | Structure |
|---|---|
| C35. | 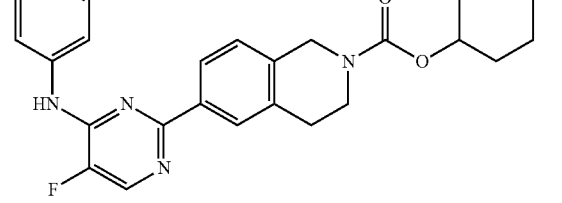 |
| C36. | 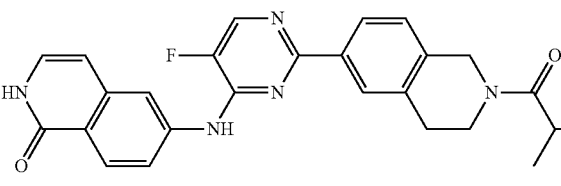 |
| C37. | 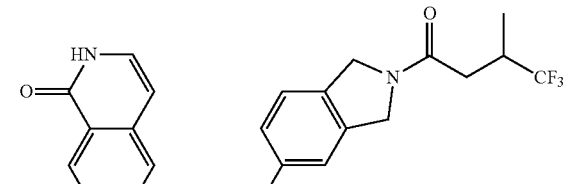 |
| C38. | 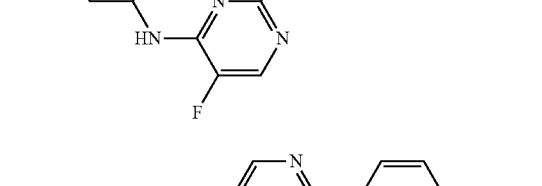 |
| C39. | 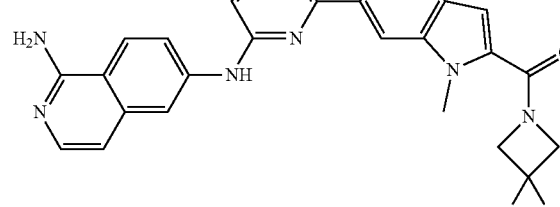 |
| C40. | 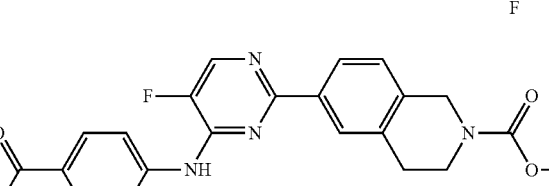 |

-continued
| No. | Structure |
|---|---|
| C41. | 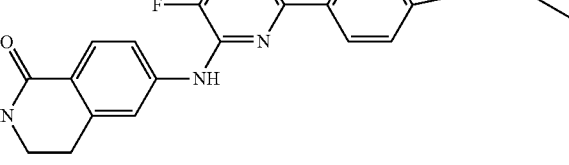 |
| C42. | 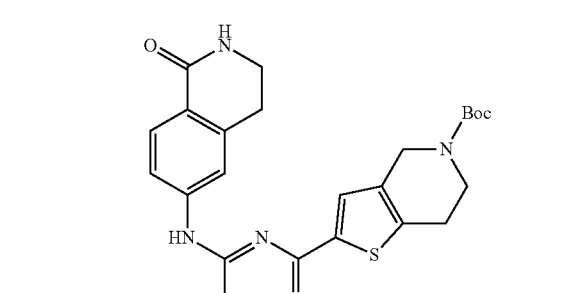 |
| C43. | 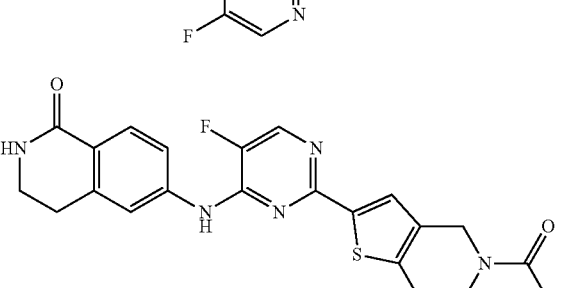 |
| C44. | 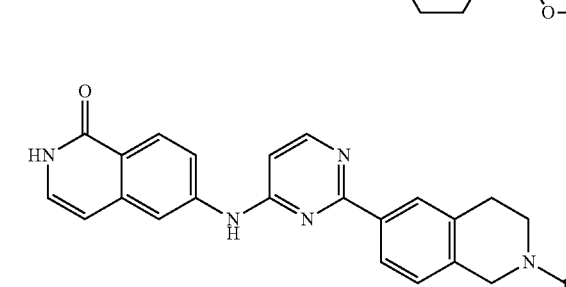 |
| C45. | 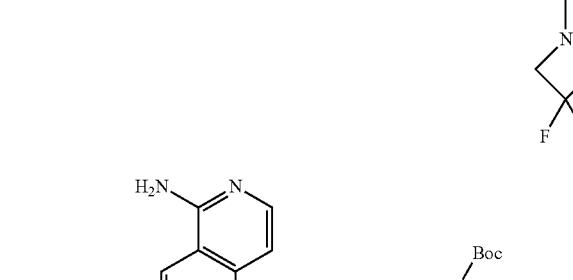 |

| No. | Structure |
|---|---|
| C46. | 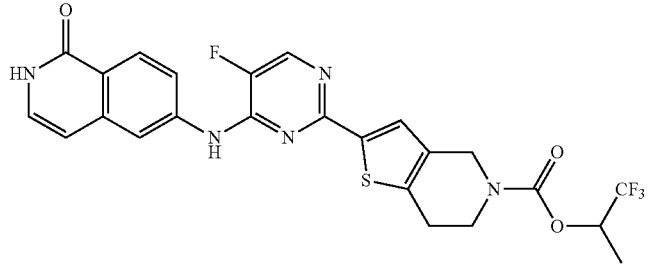 [SMILES: CC(OC(=O)N1CCc2sc(-c3ncc(F)c(Nc4ccc5c(=O)[nH]ccc5c4)n3)cc2C1)C(F)(F)F] |
| C47. | 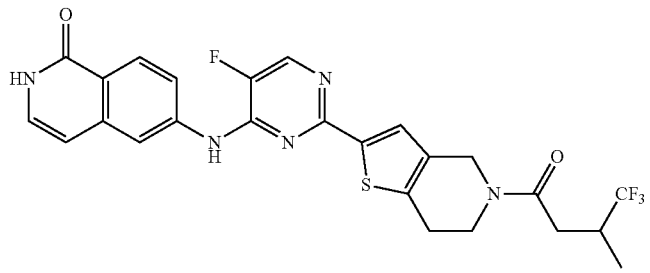 [SMILES: CC(CC(=O)N1CCc2sc(-c3ncc(F)c(Nc4ccc5c(=O)[nH]ccc5c4)n3)cc2C1)C(F)(F)F] |
| C48. | 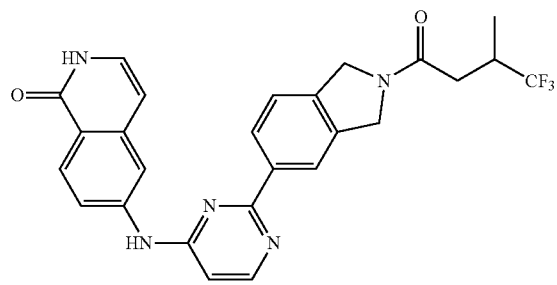 [SMILES: CC(CC(=O)N1Cc2ccc(-c3nccc(Nc4ccc5c(=O)[nH]ccc5c4)n3)cc2C1)C(F)(F)F] |
| C49. | 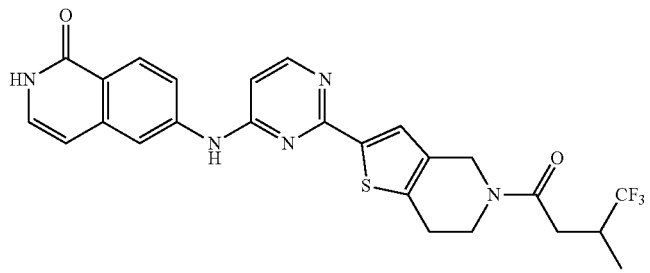 [SMILES: CC(CC(=O)N1CCc2sc(-c3nccc(Nc4ccc5c(=O)[nH]ccc5c4)n3)cc2C1)C(F)(F)F] |
| C50. | 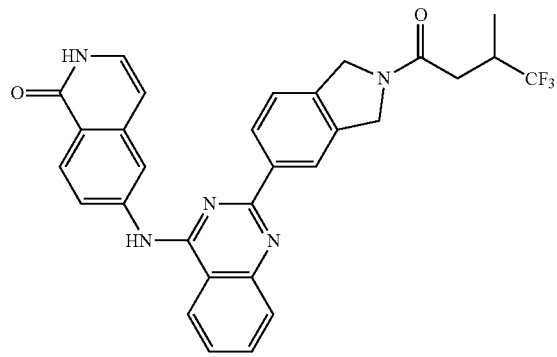 [SMILES: CC(CC(=O)N1Cc2ccc(-c3nc(Nc4ccc5c(=O)[nH]ccc5c4)c4ccccc4n3)cc2C1)C(F)(F)F] |

-continued
| No. | Structure |
|---|---|
| C51. | 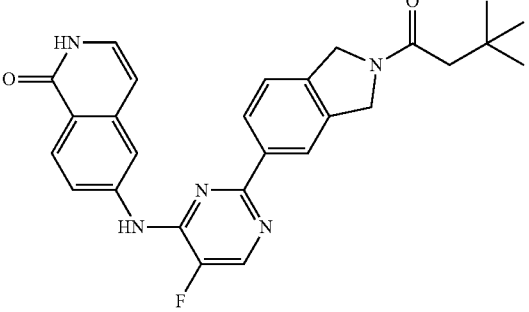 |
| C52. | 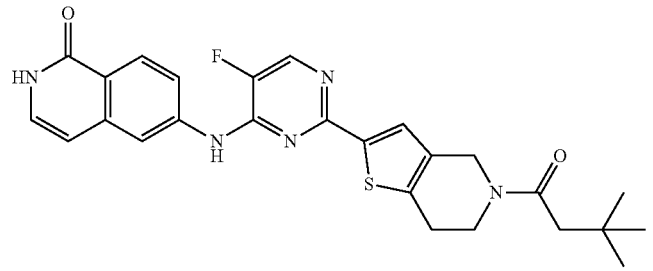 [SMILES: CC(C)(C)CC(=O)N1CCc2sc(-c3ncc(F)c(Nc4ccc5c(=O)[nH]ccc5c4)n3)cc2C1] |
| C53. | 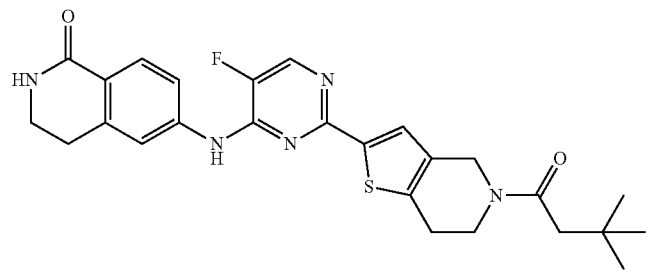 [SMILES: CC(C)(C)CC(=O)N1CCc2sc(-c3ncc(F)c(Nc4ccc5c(c4)CCNC5=O)n3)cc2C1] |
| C54. | 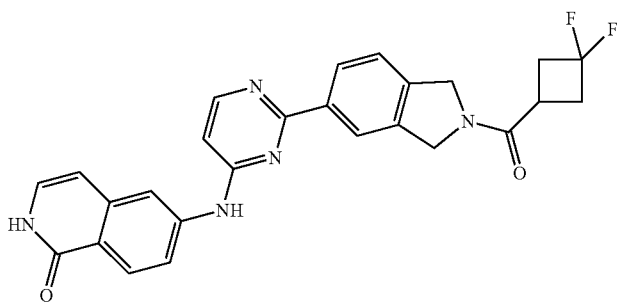 [SMILES: O=C(C1CC(F)(F)C1)N1Cc2ccc(-c3nccc(Nc4ccc5c(=O)[nH]ccc5c4)n3)cc2C1] |
| C55. | 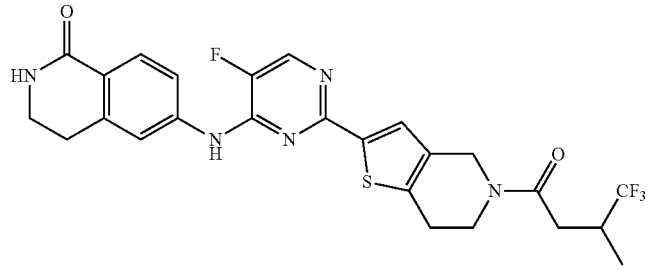 [SMILES: CC(CC(=O)N1CCc2sc(-c3ncc(F)c(Nc4ccc5c(c4)CCNC5=O)n3)cc2C1)C(F)(F)F] |

| No. | Structure |
|---|---|
| C56. | 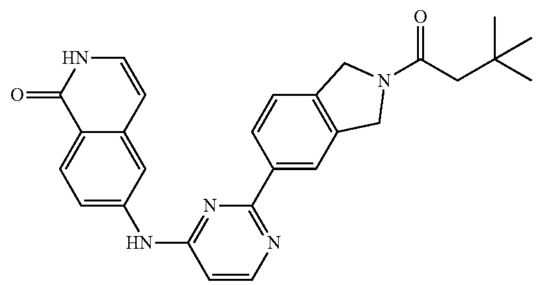 [SMILES: CC(C)(C)CC(=O)N1Cc2ccc(-c3nccc(Nc4ccc5c(=O)[nH]ccc5c4)n3)cc2C1] |
| C57. | 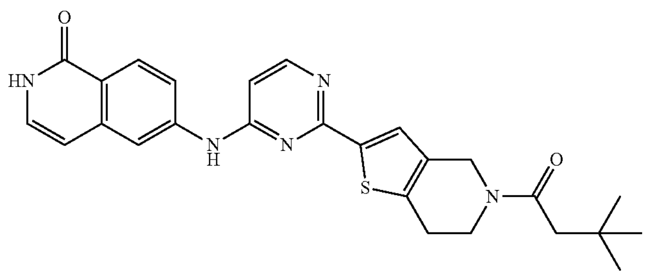 [SMILES: CC(C)(C)CC(=O)N1CCc2sc(-c3nccc(Nc4ccc5c(=O)[nH]ccc5c4)n3)cc2C1] |
| C58. | 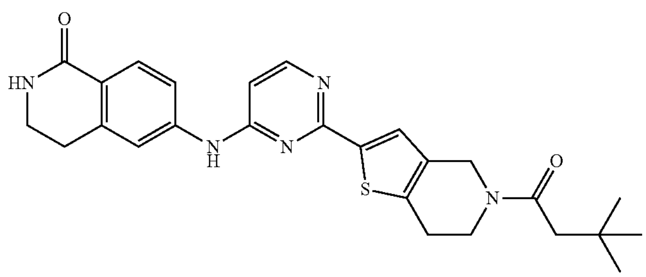 [SMILES: CC(C)(C)CC(=O)N1CCc2sc(-c3nccc(Nc4ccc5c(c4)CCNC5=O)n3)cc2C1] |
| C59. | 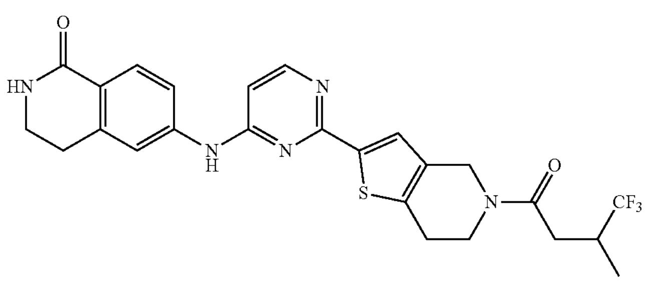 [SMILES: CC(CC(=O)N1CCc2sc(-c3nccc(Nc4ccc5c(c4)CCNC5=O)n3)cc2C1)C(F)(F)F] |
| C60. | 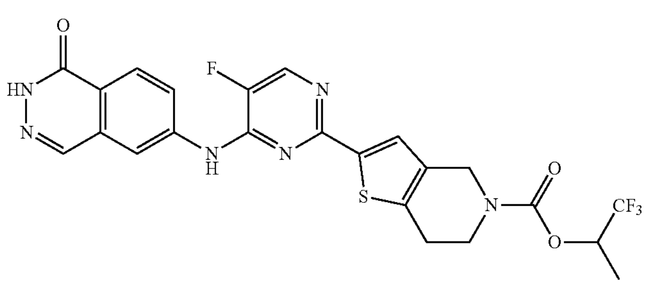 [SMILES: CC(OC(=O)N1CCc2sc(-c3ncc(F)c(Nc4ccc5c(=O)[nH]ncc5c4)n3)cc2C1)C(F)(F)F] |

-continued
| No. | Structure |
|---|---|
| C61. | 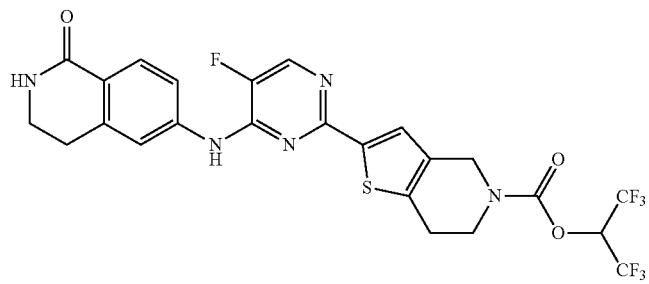 [SMILES: O=C1NCCc2cc(Nc3nc(-c4cc5c(s4)CCN(C(=O)OC(C(F)(F)F)C(F)(F)F)C5)ncc3F)ccc21] |
| C62. | 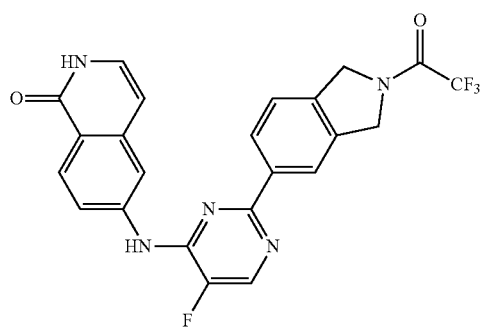 [SMILES: O=C(N1Cc2ccc(-c3ncc(F)c(Nc4ccc5c(=O)[nH]ccc5c4)n3)cc2C1)C(F)(F)F] |
| C63. | 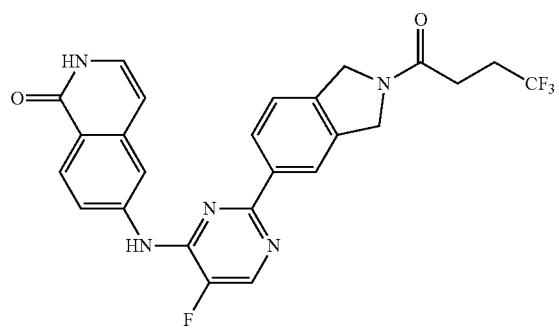 [SMILES: O=C(CCC(F)(F)F)N1Cc2ccc(-c3ncc(F)c(Nc4ccc5c(=O)[nH]ccc5c4)n3)cc2C1] |
| C64. | 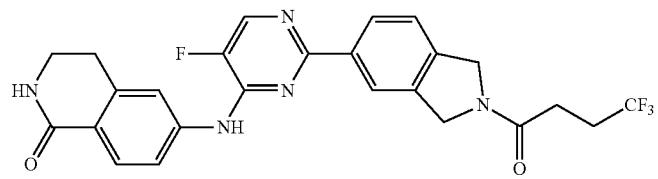 [SMILES: O=C1NCCc2cc(Nc3nc(-c4ccc5c(c4)CN(C(=O)CCC(F)(F)F)C5)ncc3F)ccc21] |
| C65. | 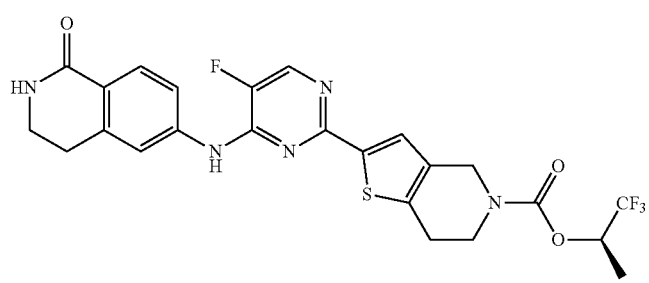 [SMILES: C[C@@H](OC(=O)N1CCc2sc(-c3ncc(F)c(Nc4ccc5c(c4)CCNC5=O)n3)cc2C1)C(F)(F)F] |

-continued
| No. | Structure |
|---|---|
| C66. | 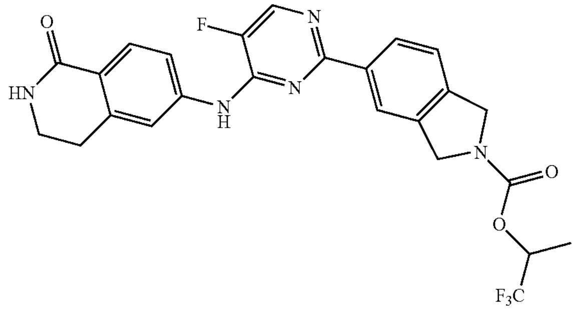 [SMILES: CC(OC(=O)N1Cc2ccc(-c3ncc(F)c(Nc4ccc5c(c4)CCNC5=O)n3)cc2C1)C(F)(F)F] |
| C67. | 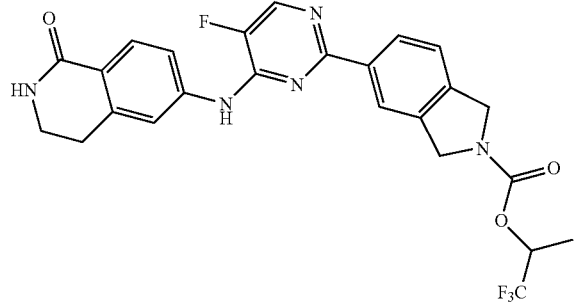 [SMILES: CC(OC(=O)N1Cc2ccc(-c3ncc(F)c(Nc4ccc5c(c4)CCNC5=O)n3)cc2C1)C(F)(F)F] |
| C68. | 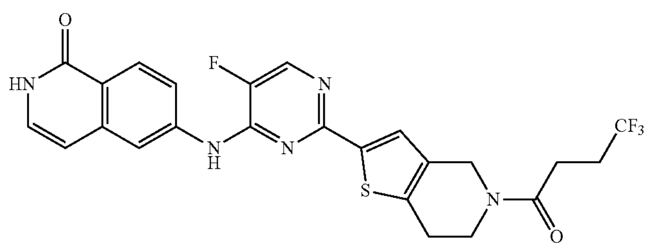 [SMILES: O=C(CCC(F)(F)F)N1CCc2sc(-c3ncc(F)c(Nc4ccc5c(=O)[nH]ccc5c4)n3)cc2C1] |
| C69. | 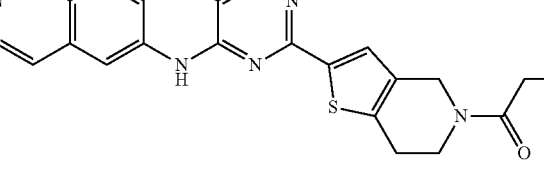 |
| C70. | 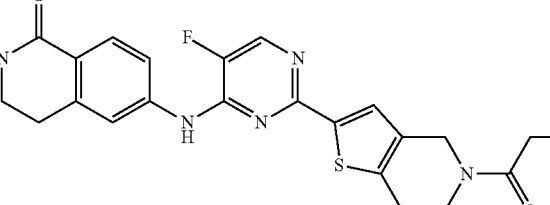 |
| C71. | 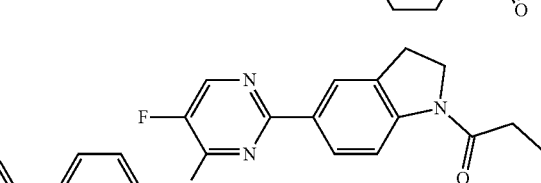 |

-continued
| No. | Structure |
|---|---|
| C72. | 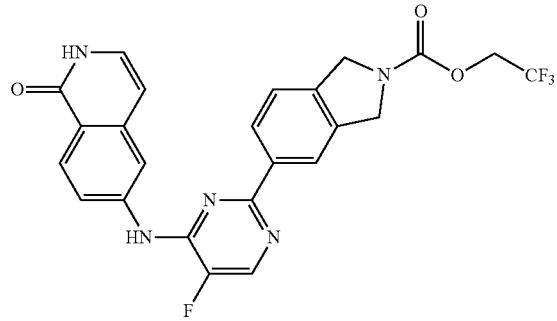 [SMILES: O=C(OCC(F)(F)F)N1Cc2ccc(-c3ncc(F)c(Nc4ccc5c(=O)[nH]ccc5c4)n3)cc2C1] |
| C73. | 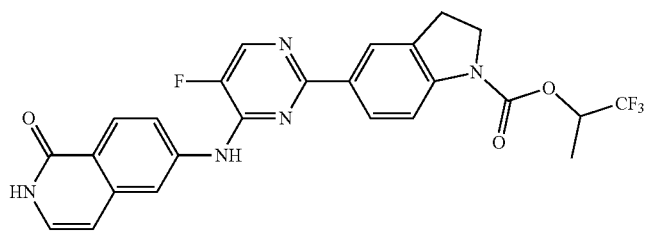 [SMILES: CC(OC(=O)N1CCc2cc(-c3ncc(F)c(Nc4ccc5c(=O)[nH]ccc5c4)n3)ccc21)C(F)(F)F] |
| C74. | 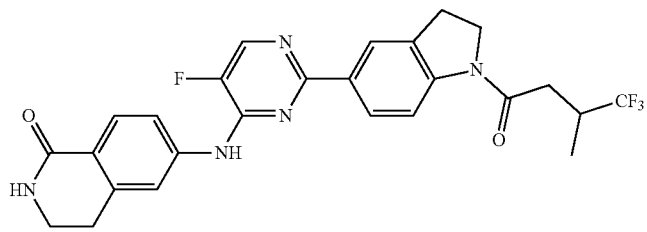 [SMILES: CC(CC(=O)N1CCc2cc(-c3ncc(F)c(Nc4ccc5c(c4)CCNC5=O)n3)ccc21)C(F)(F)F] |
| C75. | 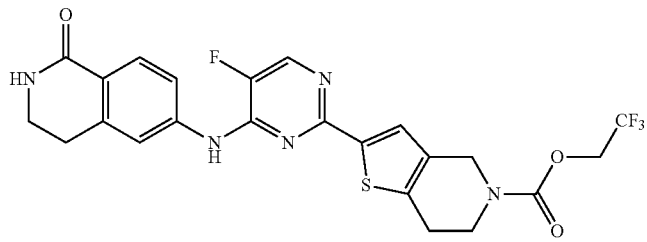 [SMILES: O=C1NCCc2cc(Nc3nc(-c4cc5c(s4)CCN(C(=O)OCC(F)(F)F)C5)ncc3F)ccc21] |
| C76. | 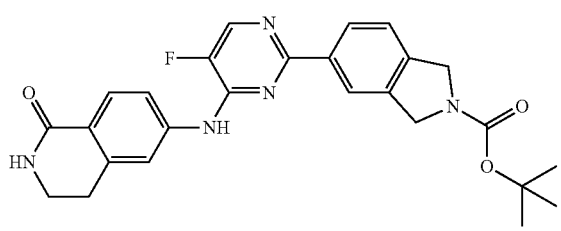 [SMILES: CC(C)(C)OC(=O)N1Cc2ccc(-c3ncc(F)c(Nc4ccc5c(c4)CCNC5=O)n3)cc2C1] |

| No. | Structure |
|-----|-----------|
| C77. | 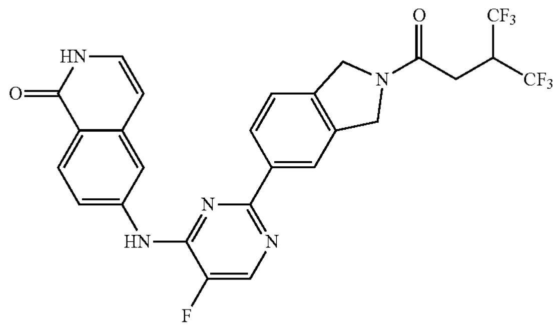 [SMILES: O=C(CC(C(F)(F)F)C(F)(F)F)N1Cc2ccc(-c3ncc(F)c(Nc4ccc5c(=O)[nH]ccc5c4)n3)cc2C1] |
| C78. | 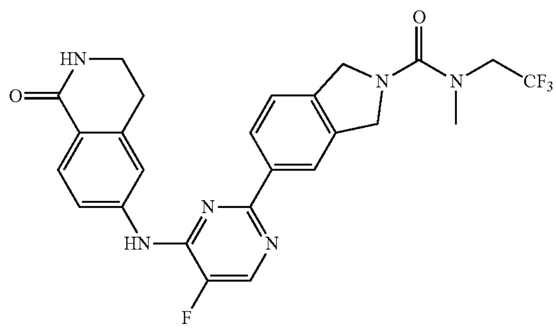 [SMILES: CN(CC(F)(F)F)C(=O)N1Cc2ccc(-c3ncc(F)c(Nc4ccc5c(c4)CCNC5=O)n3)cc2C1] |
| C79. | 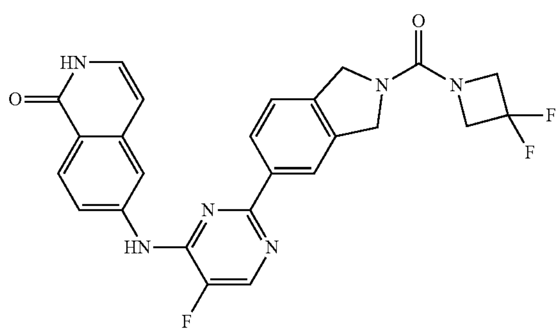 [SMILES: O=C(N1Cc2ccc(-c3ncc(F)c(Nc4ccc5c(=O)[nH]ccc5c4)n3)cc2C1)N1CC(F)(F)C1] |
| C80. | 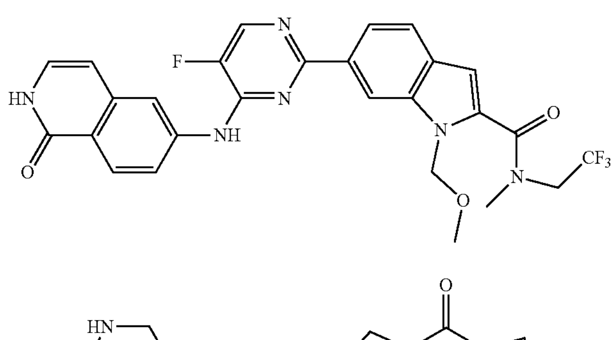 |
| C81. | 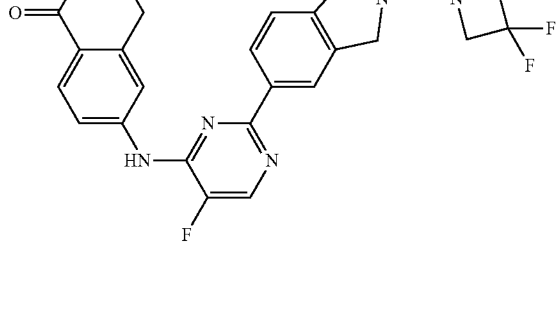 |

| No. | Structure |
|---|---|
| C82. | ![structure] |

Pharmaceutical Composition and Therapeutic Method

In some embodiments, the present invention provides a pharmaceutical composition comprising a prophylactically or therapeutically effective amount of the compound of the present invention or a pharmaceutically acceptable salt, ester, stereoisomer, polymorph, solvate, N-oxide, isotopically labeled compound, metabolite or prodrug thereof and one or more pharmaceutically acceptable carriers, and the pharmaceutical composition is preferably in the form of a solid, semi-solid, liquid, or gas preparation. In some embodiments, the pharmaceutical composition can further comprise one or more additional therapeutic agents.

In some embodiments, the present invention provides use of the compound of the present invention or a pharmaceutically acceptable salt, ester, stereoisomer, polymorph, solvate, N-oxide, isotopically labeled compound, metabolite or prodrug thereof or the pharmaceutical composition of the present invention in the preparation of a medicament for use as a Rho-associated protein kinase (ROCK) inhibitor, preferably a selective ROCK2 inhibitor.

In some embodiments, the present invention provides the compound of the present invention or a pharmaceutically acceptable salt, ester, stereoisomer, polymorph, solvate, N-oxide, isotopically labeled compound, metabolite or prodrug thereof or the pharmaceutical composition of the present invention for use as a Rho-associated protein kinase (ROCK) inhibitor, preferably a selective ROCK2 inhibitor.

In some embodiments, the present invention provides a method for the prophylaxis or treatment of a disease mediated by the Rho-associated protein kinase (ROCK), wherein the method comprises administering to a subject in need thereof an effective amount of the compound of the present invention or a pharmaceutically acceptable salt, ester, stereoisomer, polymorph, solvate, N-oxide, isotopically labeled compound, metabolite or prodrug thereof or the pharmaceutical composition of the present invention.

In some embodiments, the disease mediated by the Rho-associated protein kinase (ROCK) includes an autoimmune disorder (comprising rheumatoid arthritis, systemic lupus erythematosus (SLE; lupus), psoriasis, Crohn's disease, atopic dermatitis, eczema, or graft-versus-host disease (GVHD)); a cardiovascular disorder (comprising hypertension, atherosclerosis, restenosis, cardiac hypertrophy, cerebral ischemia, cerebral vasospasm, or erectile dysfunction); inflammation (comprising asthma, cardiovascular inflammation, ulcerative colitis, or renal inflammation); a central nervous system disorder (comprising neuronal degeneration or spinal cord injury; and the central nervous system disorder is preferably Huntington's disease, Parkinson's disease, Alzheimer's disease, Amyotrophic lateral sclerosis (ALS), or multiple sclerosis); an arterial thrombotic disorder (comprising platelet aggregation, or leukocyte aggregation); a fibrotic disorder (comprising liver fibrosis, lung fibrosis, or kidney fibrosis); a neoplastic disease (comprising a lymphoma, carcinoma (e.g., squamous cell cancer, small-cell lung cancer, pituitary cancer, esophageal cancer, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, bladder cancer, liver cancer, breast cancer, colon cancer, colorectal cancer, endometrial or uterine carcinoma, salivary gland carcinoma, kidney cancer, prostate cancer, vulval cancer, thyroid cancer, brain cancer, endometrial cancer, testis cancer, cholangiocarcinoma, gallbladder carcinoma, gastric cancer, melanoma, or head and neck cancer), leukemia, astrocytoma, soft tissue sarcoma, sarcoma, or blastoma); a metabolic syndrome; insulin resistance; hyperinsulinemia; type 2 diabetes; glucose intolerance; osteoporosis; an ocular disorder (comprising ocular hypertension, age related macular degeneration (AMD), choroidal neovascularization (CNV), diabetic macular edema (DME), iris neovascularization, uveitis, glaucoma (comprising primary open-angle glaucoma, acute angle-closure glaucoma, pigmentary glaucoma, congenital glaucoma, normal tension glaucoma, secondary glaucoma or neo vascular glaucoma), or retinitis of prematurity (ROP)).

In some embodiments, the disease mediated by the Rho-associated protein kinase (ROCK) includes lupus nephritis, atherosclerosis, rheumatoid arthritis (RA), hemangioma, angiofibroma, lung fibrosis, psoriasis, corneal graft rejection, insulin-dependent diabetes mellitus, multiple sclerosis, myasthenia gravis, Chron's disease, autoimmune nephritis, primary biliary cirrhosis, acute pancreatitis, allograph rejection, allergic inflammation, contact dermatitis, delayed hypersensitivity, inflammatory bowel disease, septic shock, osteoporosis, osteoarthritis, neuronal inflammation, Osier-Weber syndrome, restenosis, fungal infection, parasitic infection, and viral infection.

The term "pharmaceutically acceptable carrier" in the present invention refers to a diluent, auxiliary material, excipient, or vehicle with which a therapeutic is administered, and it is, within the scope of sound medical judgment, suitable for contact with the tissues of human beings and animals without excessive toxicity, irritation, allergic response, or other problem or complication, commensurate with a reasonable benefit/risk ratio.

The pharmaceutically acceptable carrier which can be employed in the pharmaceutical composition of the present invention includes, but is not limited to sterile liquids, such as water and oils, including those of petroleum, animal, vegetable or synthetic origin, such as peanut oil, soybean oil, mineral oil, sesame oil and the like. Water is an exemplary carrier when the pharmaceutical composition is administered intravenously. Physiological salines as well as aqueous dextrose and glycerol solutions can also be employed as liquid carriers, particularly for injectable solutions. Suitable pharmaceutical excipients include starch, glucose, lactose, sucrose, gelatin, maltose, chalk, silica gel, sodium stearate, glycerol monostearate, talc, sodium chloride, dried skim milk, glycerol, propylene glycol, water, ethanol and the like. The pharmaceutical composition, if desired, can also contain minor amounts of wetting or emulsifying agents, or pH buffering agents. Oral formulations can include standard carriers such as pharmaceutical grades of mannitol, lactose, starch, magnesium stearate, sodium saccharine, cellulose, magnesium carbonate, etc. Examples of suitable pharmaceutical carriers are described in e.g., Remington's Pharmaceutical Sciences (1990).

The pharmaceutical composition of the present invention can act systemically and/or topically. To this end, it can be administered through a suitable route, such as through injection, (intravenous, intraarterial, subcutaneous, intraperitoneal, intramuscular injection, including dripping), or transdermal administration, or administered via oral, buccal, nasal, transmucosal, topical, as an ophthalmic formulation, or via inhalation.

For these routes of administration, the pharmaceutical composition of the present invention can be administered in a suitable dosage form.

Such dosage forms include, but are not limited to tablets, capsules, lozenges, hard candies, powders, sprays, creams, salves, suppositories, gels, pastes, lotions, ointments, aqueous suspensions, injectable solutions, elixirs, and syrups.

As used herein, the term "effective amount" refers to the amount of a compound being administered which will relieve to some extent one or more of the symptoms of the disorder being treated.

Dosage regimens may be adjusted to provide the optimum desired response. For example, a single bolus may be administered, several divided doses may be administered over time, or the dose may be proportionally reduced or increased as indicated by the exigencies of the therapeutic situation. It is to be noted that dosage values may vary with the type and severity of the condition to be alleviated, and may include single or multiple doses. It is to be further understood that for any particular subject, specific dosage regimens should be adjusted over time according to the individual need and the professional judgment of the person administering or supervising the administration of the composition.

The amount of the compound of the present invention administered will be dependent on the subject being treated, the severity of the disorder or condition, the rate of administration, the disposition of the compound and the discretion of the prescribing physician. Generally, an effective dosage is in the range of about 0.0001 to about 50 mg per kg body weight per day, for example about 0.01 to about 10 mg/kg/day, in single or divided doses. For a 70 kg human, this would amount to about 0.007 mg to about 3500 mg/day, for example about 0.7 mg to about 700 mg/day. In some instances, dosage levels below the lower limit of the aforesaid range may be more than adequate, while in other cases, still larger doses may be employed without causing any harmful side effect, provided that such larger doses are first divided into several small doses for administration throughout the day.

The content or dosage of the compound of the present invention in the pharmaceutical composition is about 0.01 mg to about 1000 mg, suitably 0.1-500 mg, preferably 0.5-300 mg, more preferably 1-150 mg, particularly preferably 1-50 mg, e.g., 1.5 mg, 2 mg, 4 mg, 10 mg, 25 mg, etc.

Unless otherwise indicated, the term "treating" or "treatment", as used herein, means reversing, alleviating, inhibiting the progress of, or preventing the disorder or condition to which such term applies, or one or more symptoms of such disorder or condition.

As used herein, the term "subject" includes a human or non-human animal. An exemplary human subject includes a human subject having a disease (such as one described herein) (referred to as a patient), or a normal subject. The term "non-human animal" as used herein includes all vertebrates, such as non-mammals (e.g., birds, amphibians, reptiles) and mammals (such as non-human primates, livestock and/or domesticated animals (such as sheep, dog, cat, cow, pig and the like).

In some embodiments, the pharmaceutical composition of the present invention can further comprise one or more additional therapeutic agents or prophylactic agents.

EXAMPLES

The present invention is further described with reference to the following examples, which are not provided to limit the scope of the present invention.

The structure of the compound was confirmed by nuclear magnetic resonance spectrum ($^1$H NMR) or mass spectrum (MS).

Chemical shifts ($\delta$) are expressed in parts per million (ppm). $^1$H NMR was recorded on a Bruker BioSpin GmbH 400 spectrometer, the test solvent was deuterated methanol ($CD_3OD$), deuterated chloroform ($CDCl_3$) or hexadeuterated dimethyl sulfoxide ($DMSO-d_6$), and the internal standard was tetramethylsilane (TMS).

The LC-MS assay was conducted on Shimadzu LC-MS-2020 liquid chromatography-mass spectrometer (Manufacturer: Shimadzu, Model: Shimadzu LC-MS-2020).

Preparative high-performance liquid chromatography was conducted on Waters 2767 (waters sunfire, C18, 19×250 mm 10 um chromatographic column).

Thin layer chromatography (TLC) was performed with Huanghai HSGF 254 (5×20 cm) silica gel plates, and preparative thin layer chromatography was performed with GF 254 (0.4~0.5 nm) silica gel plates produced in Yantai.

The reaction was monitored by thin layer chromatography (TLC) or LC-MS, the developing solvent system included dichloromethane and methanol system, hexane and ethyl acetate system, as well as petroleum ether and ethyl acetate system, and was adjusted (by adjusting the volume ratio the solvents, or by adding triethylamine, etc.) according to the polarity of the compound to be separated.

The microwave reaction was conducted by BiotageInitiator+(400 W, RT 300° C.) microwave reactor.

Silica gel (200~300 mesh) produced by Yucheng Chemical Co., Ltd was normally employed as a stationary phase in column chromatography. The eluent system included dichloromethane and methanol system, as well as hexane and ethyl acetate system, and was adjusted (by adjusting the volume ratio the solvents, or by adding triethylamine, etc.) according to the polarity of the compound to be separated.

In the following examples, unless otherwise specified, the reaction temperature was room temperature (20° C.~30° C.).

The reagents employed in the Examples were purchased from companies such as Acros Organics, Aldrich Chemical Company, or Bide Pharmatech Ltd. etc.

The abbreviations as used in the present invention have the following meanings:

| Abbreviation | Meaning |
| --- | --- |
| ACN | acetonitrile |
| AcNH$_2$ | acetamide |
| AcOH | acetic acid |
| AcOK/KOAc | potassium acetate |
| aq. | aqueous solution |
| Boc$_2$O | di-teri-butyl dicarbonate |
| Cs$_2$CO$_3$ | cesium carbonate |
| DCM | dichloromethane |
| DIEA/DIPEA | N,N-diisopropylethylamine |
| DMAP | dimethylaminopyridine |
| DMF | N,N-dimethylformamide |
| DMSO | dimethyl sulfoxide |
| EA | ethyl acetate |
| Et$_3$N | triethylamine |
| EtOH | ethanol |
| FA | formic acid |
| HATU | O-(7-azabenzotriazol-1-yl)-N,N,N',N'-tetramethyluronium hexafluorophosphate |
| HCl | hydrochloric acid |
| H$_2$O | water |
| K$_2$CO$_3$ | potassium carbonate |
| KOH | potassium hydroxide |
| m-CPBA | chloroperoxybenzoic acid |
| MeCN | acetonitrile |
| MeOH | methanol |
| Na$_2$CO$_3$ | sodium carbonate |
| NaH | sodium hydride |
| NaOH | sodium hydroxide |
| n-BuLi | n-butyllithium |
| NH$_4$Cl | ammonium chloride |
| NMP | N-methylpyrrolidone |
| NPC | bis(4-nitrophenyl)carbonate |
| Pd/C | palladium/carbon |
| Pd$_2$(dba)$_3$ | tris(dibenzylideneacetone)dipalladium |
| Pd(dppf)Cl$_2$ | [1,1'-bis(diphenylphosphino)ferrocene]dichloropalladimn |
| Pd(OAc)$_2$ | palladium acetate |
| Pd(PPh$_3$)$_4$ | tetrakis(triphenylphosphine)palladium |
| Pd(PPh$_3$)$_2$Cl$_2$ | dichlorobis(triphenylphosphine)palladium |
| PE | petroleum ether |
| POCl$_3$ | phosphorus oxychloride |
| SOCl$_2$ | thionyl chloride |
| t-BuOH | tert-butanol |
| t-BuXPhos | 2-di-tert-butylphosphino-2',4',6'-triisopropylbiphenyl |
| TEA | triethylamine |
| TFA | trifluoroacetic acid |
| TFAA | trifluoroacetic anhydride |
| THF | tetrahydrofuran |
| Xantphos | 4,5-bis(diphenylphosphino)-9,9-dimethylxanthene |

Example 1: Preparation of 6-((2-(5-(3,3-difluoro-azetidine-1-carbonyl)isoindolin-2-yl)pyrimidin-4-yl)amino)isoquinolin-1(2H)-one (C1)

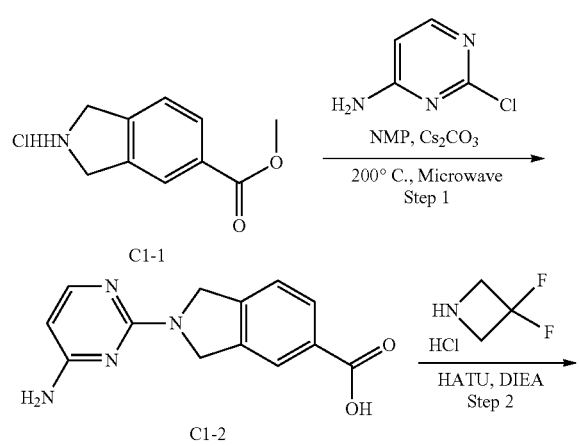

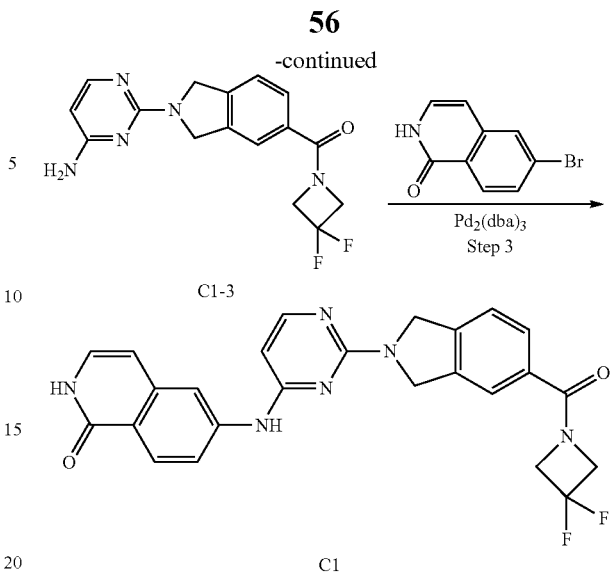

Step 1:

C1-1 (446 mg, 2.09 mmol) and 2-chloropyrimidin-4-amine (270 mg, 2.09 mmol) were dissolved in NMP (12 mL), cesium carbonate (1.02 g, 3.13 mmol) was added, and the reaction was performed under microwave radiation at 200° C. for 0.5 hour. LC-MS indicated the reaction was complete. Dichloromethane (120 mL) was added at room temperature with stirring, and the stirring was continued for 0.5 hour. The reaction was filtered, and the solid was collected, and dried to afford C1-2 (300 mg, brown solid, yield 56%). MS m/z (ESI): 257.0 [M+H]$^+$.

Step 2:

C1-2 (230 mg, 0.76 mmol), 3,3-difluoroazetidine hydrochloride (197 mg, 1.52 mmol) and HATU (289 mg, 0.76 mmol) were dissolved in DMF (5 mL), DIPEA (294 mg, 2.28 mmol) was added, and the reaction was stirred at room temperature for 1 hour. LC-MS indicated the reaction was complete. The solvent was removed by evaporation under reduced pressure, and the residue was separated by combi-flash column chromatography on silica gel (methanol/dichloromethane, 0-5%) to afford C1-3 (110 mg, brown solid, yield 43.7%).

$^1$H NMR (400 MHz, DMSO-d$_6$) δ 8.74 (d, J=4.3 Hz, 1H), 8.51 (d, J=8.4 Hz, 1H), 7.80 (d, J=4.0 Hz, 1H), 7.73 (s, 1H), 7.64 (d, J=8.0 Hz, 1H), 7.11 (s, 2H), 4.80 (s, 4H), 3.65-3.57 (m, 2H), 3.15-3.09 (m, 2H). MS m/z (ESI): 332.0 [M+H]$^+$.

Step 3:

C1-3 (100 mg, 0.3 mmol), 6-bromoisoquinolin-1(2H)-one (67.2 mg, 0.3 mmol) and cesium carbonate (293 mg, 0.9 mmol) were mixed in 1,4-dioxane (5 mL), purge with N$_2$ was performed for 3 times, and then Pd$_2$(dba)$_3$ (27.5 mg, 0.03 mmol) and Xantphos (52 mg, 0.09 mmol) were added. Purge with N$_2$ was performed again for 3 times, and then the reaction was placed in an oil bath at 90° C., and allowed to proceed for 16 hours. LC-MS indicated there was a small amount of the product. Pd$_2$(dba)$_3$ (27.5 mg, 0.03 mmol) and Xantphos (52 mg, 0.09 mmol) were supplemented, and the reaction was further allowed to proceed in an oil bath at 90° C. for 24 hours. LC-MS indicated the conversion rate of the product increased. The reaction solution was cooled to room temperature, filtered, the filtrate was concentrated under reduced pressure to dryness, and the crude product was separated by preparative liquid chromatography (acetonitrile/water (0.1% TFA), 20~60%, 30 minutes) to afford C1 (13 mg, light yellow solid, yield 7.4%).

$^1$H NMR (400 MHz, DMSO-d$_6$) δ 11.18 (s, 1H), 10.82 (s, 1H), 8.24 (d, J=8.0 Hz, 1H), 8.17 (s, 1H), 8.06 (d, J=8.0 Hz, 1H), 7.88-7.78 (m, 2H), 7.73-7.67 (m, 1H), 7.64-7.55 (m,

1H), 7.23-7.17 (m, 1H), 6.64 (t, J=6.8 Hz, 1H), 6.47 (d, J=6.8 Hz, 1H), 5.08 (s, J=8.0 Hz, 2H), 4.95 (s, J=8.0 Hz, 2H), 4.79 (s, 2H), 4.51 (s, 2H). MS m/z (ESI): 474.6 [M+H]+.

Example 2: Preparation of 6-((2-(2-(3,3-difluoro-azetidine-1-carbonyl)-1H-indol-6-yl)-5-fluoropyrimidin-4-yl)amino)isoquinolin-1(2H)-one (C9I <sup>1</sup>H NMR (400 MHz, DMSO-d<sub>6</sub>) δ 11.88 (s, 1H), 7.61 (s, 1H), 7.60 (d, J=8.6 Hz, 1H), 7.20 (d, J=8.6 Hz, 1H), 6.94 (s, 1H), 4.98 (s, 2H), 4.56 (s, 2H). MS m/z (ESI): 314.9, 316.9 [M+H]+.

Step 2:
Compound C9-2 (1.151 g, 3.66 mmol), bis(pinacolato)diboron (1.024 g, 4.03 mmol) and potassium acetate (1.077 g, 10.98 mmol) were dissolved in 1,4-dioxane (20 mL), purge with N<sub>2</sub> was performed for 3 times, followed by

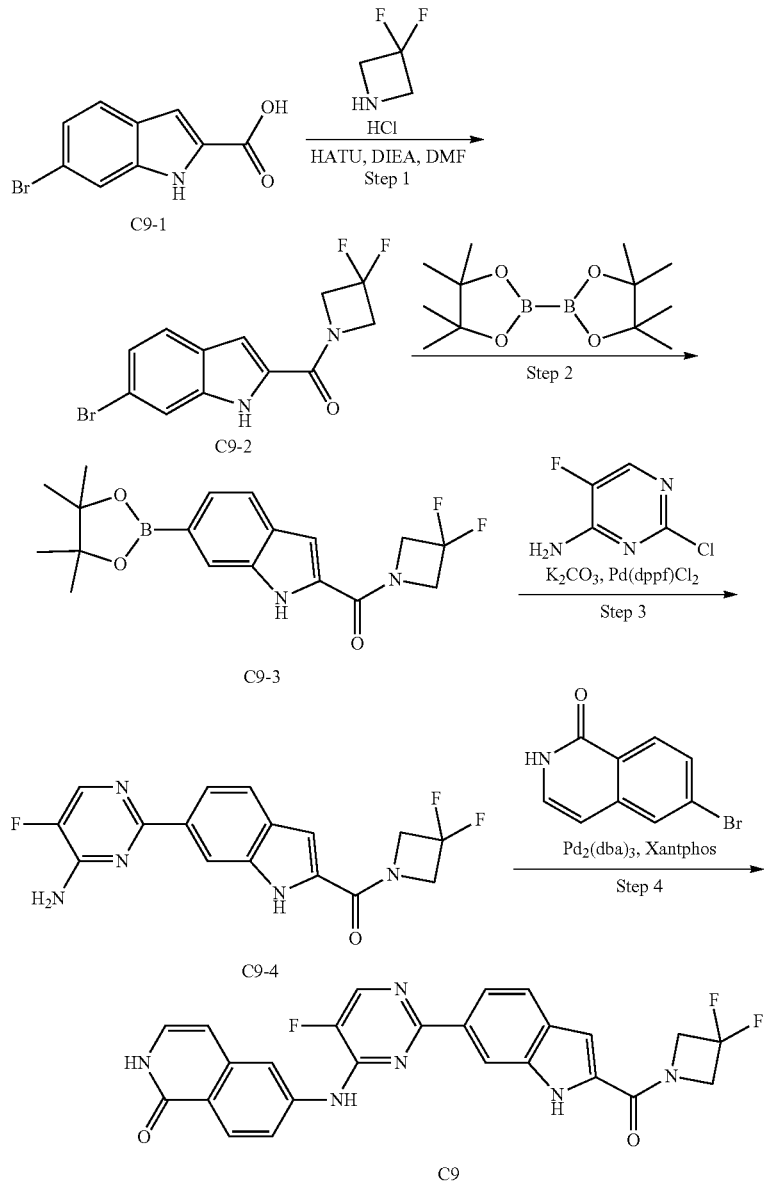

Step 1:
C9-1 (31.3 g, 130 mmol), 3,3-difluoroazetidine hydrochloride (20 g, 140 mmol), HATU (60 g, 160 mmol) and DMF (330 mL) were added to a 1 L flask, DIEA (50 g, 390 mmol) was added with stirring, and the reaction was performed at room temperature overnight. LC-MS indicated the reaction was complete. The reaction solution was concentrated, water (200 mL), methanol (20 mL) and acetonitrile (20 mL) were added, the mixture was stirred at room temperature for 1 hour, and filtered. The solid was collected and dried to afford C9-2 (41 g, brown solid, yield 100%).

addition of Pd(dppf)Cl<sub>2</sub> (536 mg, 0.732 mmol). Purge with N<sub>2</sub> was performed again for 3 times, and then the reaction was heated under reflux for 16 hours. LC-MS indicated the reaction was complete. The reaction was cooled to room temperature, insoluble materials were filtered off, and the organic phase was concentrated under reduced pressure to afford a crude product, which was separated by column chromatography on silica gel (dichloromethane:methanol=30:1) to afford compound C9-3 (700 mg, brown solid, yield 53%).

¹H NMR (400 MHz, DMSO-d₆) δ 11.90 (s, 1H), 7.83 (s, 1H), 7.62 (d, J=8.0 Hz, 1H), 7.35 (d, J=8.1 Hz, 1H), 6.92 (s, 1H), 4.99 (s, 2H), 4.58 (s, 2H), 1.31 (s, 12H). MS m/z (ESI): 363.0 [M+H]⁺.

Step 3:

Compound C9-3 (300 mg, 0.83 mmol) and 2-chloro-5-fluoropyrimidin-4-amine (122 mg, 0.83 mmol) were dissolved in 1,4-dioxane (20 mL), water (2 mL), potassium carbonate (343 mg, 2.49 mmol) and Pd(dppf)Cl₂ (61 mg, 0.08 mmol) were added, and then purge with nitrogen was performed for three times. The reaction solution was stirred at 110° C. for 16 hours. LC-MS indicated the reaction was complete, the reaction solution was cooled to room temperature, and the reaction solvent was removed by rotary evaporation in vacuum. The residue was separated and purified by column chromatography on silica gel (dichloromethane:methanol=10:1), to afford a crude product of compound C9-4 (400 mg, brown solid).

¹H NMR (400 MHz, DMSO-d6) δ 12.00 (s, 1H), 8.38 (s, 1H), 8.25 (s, 1H), 8.03 (d, J=8.4 Hz, 1H), 7.66 (d, J=8.3 Hz, 1H), 7.31 (s, 2H), 6.94 (s, 1H). MS m/z (ESI): 347.8 [M+H]⁺.

Step 4:

Compound C9-4 (100 mg, 0.29 mmol) and 6-bromoisoquinolin-1(2H)-one (65 mg, 0.29 mmol) were dissolved in 1,4-dioxane (10 mL), cesium carbonate (283 mg, 0.87 mmol), Pd₂(dba)₃ (27 mg, 0.03 mmol) and Xantphos (34 mg, 0.06 mmol) were added, purge with nitrogen was performed for three times, and the reaction solution was stirred under microwave radiation at 110° C. for 1 hour. LC-MS indicated the reaction was complete. The reaction solution was cooled to room temperature, filtered, and the reaction solvent was removed by rotary evaporation in vacuum. The resulting crude product was purified by preparative HPLC (ACN/H₂O (0.1% TFA), 20~60%) to afford compound C9 (20 mg, yellow solid, yield 14%).

¹HNMR (400 MHz, DMSO-d₆) δ 12.14 (s, 1H), 11.12 (s, 1H), 9.9 (s, 1H), 8.58 (s, 1H), 8.49 (s, 1H), 8.25 (d, J=8.2 Hz, 2H), 8.09 (s, 2H), 7.75 (d, J=8.6 Hz, 1H), 7.19 (s, 1H), 6.98 (s, 1H), 6.59 (d, J=7.5 Hz, 1H), 5.04 (s, 2H), 4.56 (s, 2H). MS m/z (ESI): 490.7 [M+H]⁺.

The compounds in the following Table were prepared according to methods similar to that described in Example 2.

| No. | Compound Structure | Compound Name | Starting material or regent different from that in Example 2 | Characterization Data |
|---|---|---|---|---|
| C20 | (structure shown) | 6-((2-(2-(3,3-difluoroazetidine-1-carbonyl)-1-(methoxymethyl)-1H-indol-6-yl)-5-fluoropyrimidin-4-yl)amino)isoquinolin-1(2H)-one | (C9-3) in Step 3 was replaced with (C20-2)*. | ¹H NMR (400 MHz, DMSO-d₆) δ 11.15 (s, 1H), 10.03 (s, 1H), 8.60 (d, J = 6.5 Hz, 2H), 8.37 (s, 1H), 8.27-8.10 (m, 2H), 7.96 (d, J = 9.0 Hz, 1H) 7.79 (d, J = 8.6 Hz, 1H), 7.19 (s, 2H), 6.60 (d, J = 7.0 Hz, 1H), 5.95 (s, 2H), 4.65 (s, 4H), 3.20 (s, 3H). MS m/z (ESI): 534.7 [M + H]⁺. |
| C21 | (structure shown) | 6-((2-(2-(3,3-difluoroazetidine-1-carbonyl)-1-(methoxymethyl)-1H-indol-6-yl)pyrimidin-4-yl)amino)isoquinolin-1(2H)-one | (C9-3) in Step 3 was replaced with (C20-2), and (F-pyrimidine-Cl with H₂N) was replaced with (pyrimidine-Cl with H₂N) | ¹H NMR (400 MHz, DMSO-d₆) δ 11.09 (s, 1H), 10.19 (s, 1H), 8.68 (s, 1H), 8.51 (d, J = 6.3 Hz, 1H), 8.32 (s, 1H), 8.28-8.24 (m, 1H), 8.17 (s, 1H), 7.81 (d, J = 8.4 Hz, 1H), 7.77-7.72 (m, 1H), 7.20 (s, 2H), 6.88-6.85 (m, 1H), 6.62-6.57 (m, 1H), 5.97 (s, 2H), 4.87-4.58 (m, 4H), 3.22 (s, 3H). MS m/z (ESI): 516.7 [M + H]⁺. |

| No. | Compound Structure | Compound Name | Starting material or regent different from that in Example 2 | Characterization Data |
|---|---|---|---|---|
| C22 | 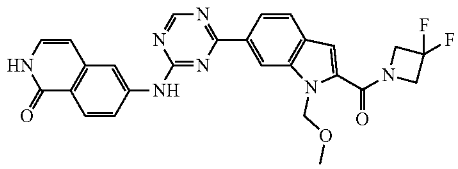 [SMILES: COCn1c(C(=O)N2CC(F)(F)C2)cc2ccc(-c3ncnc(Nc4ccc5c(=O)[nH]ccc5c4)n3)cc21] | 6-((4(2-(3,3-difluoro-azetidine-1-carbonyl)-1-(methoxy-methyl)-1H-indol-6-yl)-1,3,5-triazin-2-yl)amino)isoquinolin-1(2H)-one | (C9-3) in Step 3 was replaced with (C20-2), and was replaced with | 41 NMR (400 MHz, DMSO-d$_6$) δ 11.14 (s, 1H), 10.73 (s, 1H), 8.95 (s, 1H), 8.77 (s, 1H), 8.28 (s, 2H), 8.18 (s, 1H), 7.85 (s, 2H), 7.20 (d, J = 19.9 Hz, 2H), 6.56 (s, 1H), 5.96 (s, 2H), 4.93 (bs, 2H), 4.59 (bs, 2H), 3.22 (s, 3H). MS m/z (ESI): 517.8 [M + H]$^+$. |
| C38-5 | 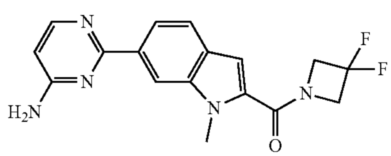 [SMILES: Cn1c(C(=O)N2CC(F)(F)C2)cc2ccc(-c3nccc(N)n3)cc21] | (6-(4-amino-pyrimidin-2-yl)-1-methyl-1H-indol-2-yl)(3,3-difluoro-azetidin-1-yl)methanone | (C9-1) in Step 3 was replaced with ; in Step 3 wass replaced with ; and Step 4 was omitted. | $^1$H NMR (400 MHz, DMSO-d$_6$) δ 8.45 (s, 1H), 8.19 (d, J = 5.7 Hz, 1H), 8.14 (d, J = 8.4 Hz, 1H), 7.66 (d, J = 8.5 Hz, 1H), 7.04 (s, 1H), 6.90 (s, 2H), 6.36 (d, J = 5.8 Hz, 1H), 4.84 (s, 2H), 4.58 (s, 2H), 4.00 (s, 3H). |

Synthesis of Intermediates C20-1 and C20-2:

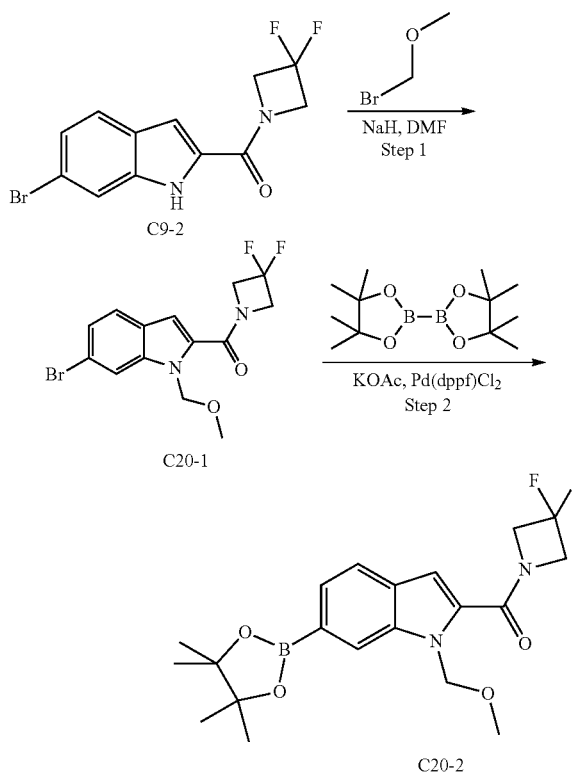

Step 1

Compound C9-2 (9 g, 28.6 mmol) was dissolved in DMF (100 mL), and was cooled to 0° C. in an ice water bath under the protection of N₂. NaH (60%, 1.7 g, 42.9 mmol) was added in portions, and after stirring for 0.5 hour, bromomethyl methyl ether (5.4 g, 42.9 mmol) was added. The reaction was allowed to warmed to room temperature and stirred for 16 hours. LC-MS indicated the reaction was complete. The reaction solution was cooled to 0° C., added with water (10 mL), and concentrated to remove the solvent. The resulting residue was dissovled by adding dichloromethane (200 mL), washed with water (100 mL×3), and the organic phase was dried over anhydrous sodium sulfate, and rotary evaporated to dryness, to afford compound C20-1 (10.2 g, grey solid, yield 98%).

$^1$H NMR (400 MHz, CDCl$_3$) δ 7.76 (s, 1H), 7.53 (d, J=8.4 Hz, 1H), 7.33 (d, J=8.5 Hz, 1H), 6.79 (s, 1H), 5.89 (s, 2H), 4.64 (t, J=10.5 Hz, 4H), 3.33 (s, 3H). MS m/z (ESI): 380.6, 382.7 [M+Na]$^+$.

Step 2:

Compound C20-1 (10.2 g, 28.4 mmol), bis(pinacolato)diboron (7.94 g, 31.3 mmol) and potassium acetate (8.35 g, 85.2 mmol) were dissolved in 1,4-dioxane (120 mL), purge with N₂ was performed for 3 times, and then Pd(dppf)Cl₂ (2.08 g, 2.84 mmol) was added. Purge with N₂ was performed again for 3 times, and then the reaction was heated to 100° C., and allowed to proceed under reflux for 16 hours. LC-MS indicated the reaction was complete. The reaction was cooled to room temperature, the reaction solution was concentrated under reduced pressure to afford a crude product, which was separated by column chromatography on silica gel (petroleum ether:ethyl acetate=4:1) to afford compound C20-2 (11 g, white solid, yield 95.4%).

$^1$H NMR (400 MHz, DMSO-d$_6$) δ 7.94 (d, J=4.8 Hz, 1H), 7.67 (d, J=7.9 Hz, 1H), 7.47 (d, J=7.9 Hz, 1H), 7.13 (s, 1H), 5.89 (s, 2H), 4.72 (d, J=122.5 Hz, 4H), 3.15 (s, 3H), 1.33 (s, 12H). MS m/z (ESI): 429.1 [M+Na]$^+$.

Example 3: Preparation of 6-((2-(2-(3,3-difluorocyclobutane-1-carbonyl)isoindolin-5-yl)pyrimidin-4-yl)amino)isoquinolin-1(2H)-one (C54)

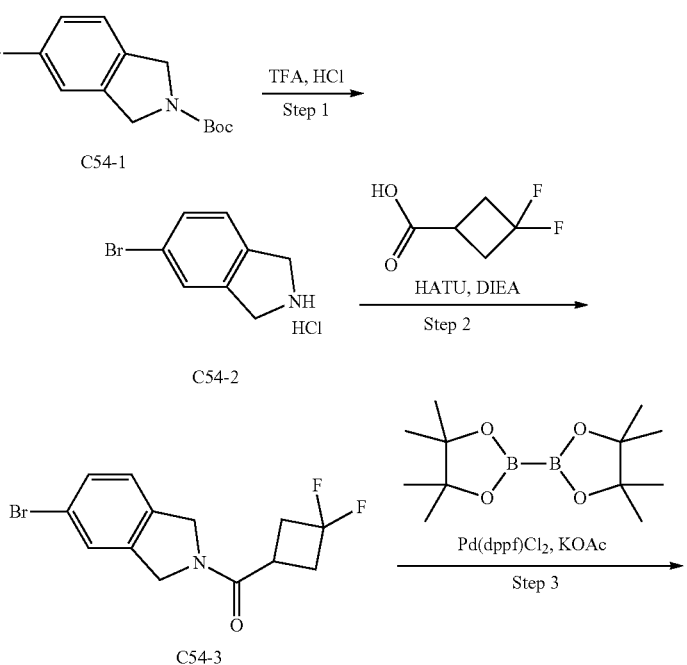

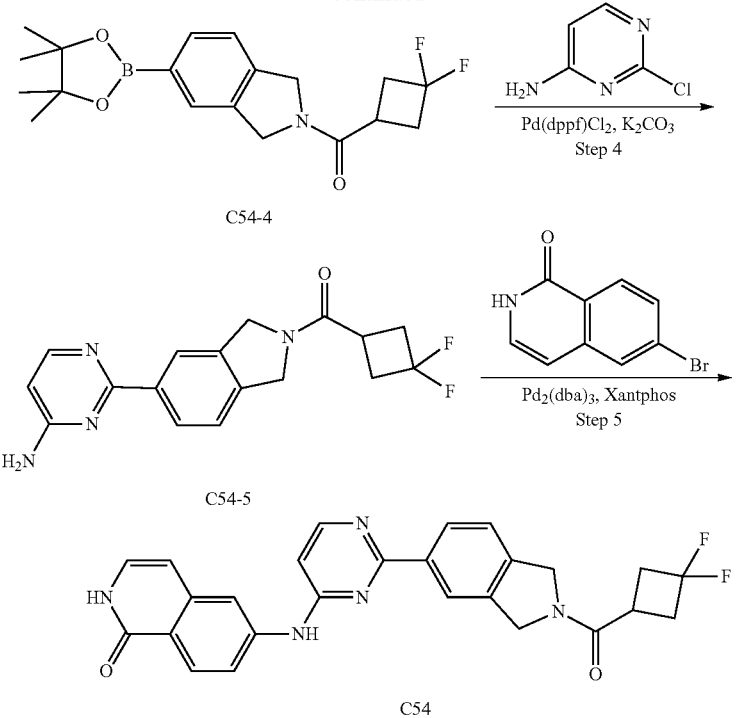

Step 1:

Compound C54-1 (20 g, 67 mmol) was dissolved in dichloromethane (20 mL), trifluoroacetic acid (50 mL) was added, and the reaction solution was stirred at room temperature for 16 hours. The reaction solvent and trifluoroacetic acid were removed by rotary evaporation in vacuum, the residue was added with 20 mL water and 40 mL concentrated hydrochloric acid, and the precipitated solid was filtered and dried to afford compound C54-2 (15.3 g, grey solid).

$^1$H NMR (400 MHz, CDCl$_3$) δ 7.39 (s, 1H), 7.34 (d, J=8.2 Hz, 1H), 7.12 (d, J=8.0 Hz, 1H), 4.22 (d, J=14.1 Hz, 4H). MS m/z (ESI): 197.9, 199.8 [M-Cl]$^+$.

Step 2:

3,3-difluorocyclobutylcarboxylic acid (3.1 g, 23 mmol) was dissolved in N,N-dimethylformamide (100 mL), HATU (9.5 g, 25 mmol), diisopropylethylamine (8.7 g, 67 mmol) and C54-2 (4.5 g, 19 mmol) were sequentially added, and the reaction was further stirred at room temperature for 16 hours. The reaction solvent was removed by rotary evaporation in vacuum, the residue was dissolved in 20 mL dichloromethane, washed with water (20 mL×3), and then the organic phase was concentrated until solid precipitated. After fully precipitated, the solid was filtered, and dried to afford a crude product of C54-3 (4.2 g, grey solid, yield 70%).

MS m/z (ESI): 315.7, 317.8 [M+H]$^+$.

Step 3:

Compound C54-3 (4.1 g, 13 mmol) and bis(pinacolato)diboron (4.1 g, 16 mmol) were dissolved in N,N-dimethylformamide (100 mL), potassium acetate (4.1 g, 16 mmol) and Pd(dppf)Cl$_2$ (0.95 g, 1.3 mmol) were added, purge with nitrogen was performed for three times, and the reaction solution was stirred at 110° C. for 16 hours. LC-MS indicated the reaction was complete. The reaction solution was cooled to room temperature, and the reaction solvent was removed by rotary evaporation in vacuum. The residue was separated and purified by column chromatography on silica gel (petroleum ether:ethyl acetate=5:1), to afford compound C54-4 (3.8 g, white solid, yield 81%).

$^1$H NMR (400 MHz, CDCl$_3$) δ 7.73-7.79 (m, 2H), 728-7.35 (m, 1H), 4.78-4.85 (m, 4H), 3.09-3.17 (m, 1H), 2.94-3.05 (m, 2H), 2.80-2.85 (m, 2H), 1.38 (s, 12H). MS m/z (ESI): 363.9 [M+H]$^+$.

Step 4:

Compound C54-4 (545 mg, 1.5 mmol), 2-chloropyrimidin-4-amine (176.3 mg, 1.5 mmol), potassium carbonate (621 mg, 4.5 mmol) and Pd(dppf)Cl$_2$ (110 mg, 0.15 mmol) were mixed in dioxane (25 mL) and water (2.5 mL), purge with nitrogen was performed for 3 times, and the reaction was allowed to proceed in an oil bath at 110° C. overnight. LC-MS indicated the reaction was complete. The reaction solution was cooled to room temperature, filtered, the filtrate was concentrated under reduced pressure, and the crude product was separated by combi-flash column chromatography on silica gel (methanol/dichloromethane=0~5%) to afford compound C54-5 (300 mg, light yellow solid, yield 60.6%).

$^1$H NMR (300 MHz, DMSO-d$_6$) δ 8.37-8.16 (m, 3H), 7.45-7.35 (m, 1H), 6.92 (s, 2H), 6.36 (d, J=5.6 Hz, 1H), 4.86 (s, 2H), 4.73 (s, 2H), 3.28-3.24 (m, 1H), 2.90-2.79 (m, 4H).

Step 5:

Compound C54-5 (100 mg, 0.3 mmol), 6-bromoisoquinolin-1(2H)-one (68 mg, 0.3 mmol), cesium carbonate (196 mg, 0.6 mmol), Pd$_2$(dba)$_3$ (27.5 mg, 0.03 mmol) and Xantphos (17.5 mg, 0.03 mmol) were mixed in dioxane (2 mL), purge with nitrogen was performed for 3 times, and the reaction was allowed to proceed in an oil bath at 110° C. overnight. LC-MS indicated the reaction was complete. The reaction was cooled to room temperature, filtered to remove insoluble salts, the filtrate was concentrated under reduced pressure, and the resulting crude product was purified by preparative HPLC (ACN/H₂O (0.1% TFA), 20~60%), to afford compound C54 (8 mg, yellow solid, yield 4.5%).

¹H NMR (400 MHz, DMSO-d₆) δ 11.09 (d, J=4.0 Hz, 1H), 10.24 (s, 1H), 8.49 (dd, J=8.0, 2.0 Hz, 1H), 8.34 (s, 1H), 8.30 (d, J=12.0 Hz, 1H), 8.21 (t, J=2.0 Hz, 1H), 8.19-8.12 (m, 1H), 7.84-7.73 (m, 1H), 7.54 (dd, J=16.0, 8.0 Hz, 1H), 7.20-7.15 (m, 1H), 6.88 (d, J=8.0 Hz, 1H), 6.52 (d, J=8.0 Hz, 1H), 4.92 (d, J=12.0 Hz, 2H), 4.77 (d, J=17.0 Hz, 2H), 3.34-3.27 (m, 1H), 2.90-2.81 (m, 4H). MS m/z (ESI): 473.6 [M+H]⁺.

The compounds in the following Table were prepared according to methods similar to that described in Example 3.

| No. | Compound Structure | Compound Name | Starting material or regent different from that in Example 3 | Characterization Data |
|---|---|---|---|---|
| C3 | 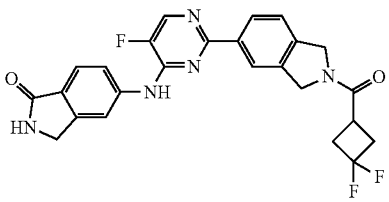 [SMILES: O=C1NCc2cc(Nc3nc(-c4ccc5c(c4)CN(C(=O)C4CC(F)(F)C4)C5)ncc3F)ccc21] | 5-((2-(2-(3,3-difluoroo-cyclobutane-1-carbonyl)isoindolin-5-yl)-5-fluoro-pyrimidin-4-yl)amino)isoindolin-1-one | in Step 4 was replaced with and in Step 5 was replaced with | ¹H NMR (400 MHz, DMSO-d₆) δ 9.99 (s, 1H), 8.56 (s, 1H), 8.45 (d, J = 5.1 Hz, 1H), 8.24 (d, J = 8.5 Hz, 2H), 8.15 (d, J = 14.7 Hz, 1H), 7.94 (d, J = 7.8 Hz, 1H), 7.71 (d, J = 8.2 Hz, 1H), 7.51-7.46 (m, 1H), 4.89 (d, J = 10.5 Hz, 2H), 4.74 (d, J = 15.9 Hz, 2H), 4.44 (s, 2H), 3.29 (s, 1H), 2.86 (dd, J = 16.5, 8.4 Hz, 4H). MS m/z (ESI): 480.1 [M + H]⁺. |
| C5 | 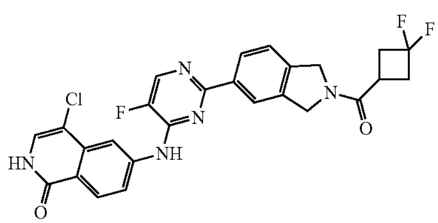 [SMILES: O=C(C1CC(F)(F)C1)N1Cc2ccc(-c3ncc(F)c(Nc4ccc5c(=O)[nH]cc(Cl)c5c4)n3)cc2C1] | 4-chloro-6-((2-(2-(3,3-difluoroo-cyclobutane-1-carbonyl)isoindolin-5-yl)-5-fluoro-pyrimidin-4-yl)amino)isoquinolin-1(2H)-one | in Step 4 was replaced with and in Step 5 was replaced with | ¹H NMR (400 MHz, DMSO-d₆) δ 11.48 (s, 1H), 10.19 (s, 1H), 8.94 (d, J = 40.2 Hz, 1H), 8.62 (s, 1H), 8.45-8.36 (m, 2H), 8.24 (d, J = 8.3 Hz, 1H), 7.91 (dd, J = 27.6, 8.5 Hz, 1H), 7.56-7.44 (m, 2H), 4.89 (s, 2H), 4.75 (s, 2H), 3.16-3.05 (m, 1H), 2.91-2.82 (m, 4H). MS m/z (ESI): 525.7 [M + H]⁺. |

-continued

| No. | Compound Structure | Compound Name | Starting material or regent different from that in Example 3 | Characterization Data |
|---|---|---|---|---|
| C6 | 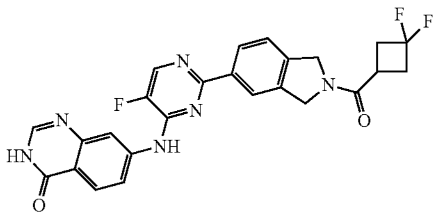 [SMILES: O=C(C1CC(F)(F)C1)N1Cc2ccc(-c3ncc(F)c(Nc4ccc5c(=O)[nH]cnc5c4)n3)cc2C1] | 7-((2-(2-(3,3-difluoroo-cyclobutane-1-carbonyl)isoindolin-5-yl)-5-fluoro-pyrimidin-4-yl)amino)quinazolin-4(3H)-one | $H_2N$-pyrimidine-Cl in Step 4 was replaced with F-pyrimidine-$NH_2$-Cl; and HN-isoquinolinone-Br in Step 5 was replaced with HN-quinazolinone-Br. | $^1$H NMR (400 MHz, DMSO-$d_6$) δ 10.14 (s, 1H), 8.61 (d, J = 4.0 Hz, 1H), 8.34-8.23 (m, 4H), 8.17 (d, J = 4.0 Hz, 1H), 8.14 (s, 1H), 8.10-8.04 (m, 1H), 7.49 (q, J = 8.0 Hz, 1H), 4.89 (d, J = 8.0 Hz, 2H), 4.75 (d, J = 12.0 Hz, 2H), 3.31-3.28 (m, 1H), 2.89-2.81 (m, 4H). MS m/z (ESI): 493.1 [M + H]$^+$. |
| C7 | 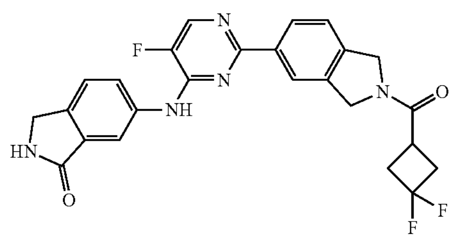 [SMILES: O=C1NCc2ccc(Nc3nc(-c4ccc5c(c4)CN(C(=O)C4CC(F)(F)C4)C5)ncc3F)cc21] | 6-((2-(2-(3,3-difluoroo-cyclobutane-1-carbonyl)isoindolin-5-yl)-5-fluoro-pyrimidin-4-yl)amino)isoindolin-1-one | $H_2N$-pyrimidine-Cl in Step 4 was replaced with F-pyrimidine-$NH_2$-Cl; and HN-isoquinolinone-Br in Step 5 was replaced with HN-isoindolinone-Br. | $^1$H NMR (400 MHz, DMSO-$d_6$) δ 9.93 (s, 1H), 8.62 (s, 1H), 8.53 (s, 1H), 8.36 (d, J = 21.2 Hz, 1H), 8.28-8.23 (m, 2H), 8.05-7.98 (m, 1H), 7.62 (d, J = 8.1 Hz, 1H), 7.49-7.43 (m, 1H), 4.88 (d, J = 5.8 Hz, 2H), 4.74 (d, J = 5.8 Hz, 2H), 4.38 (s, 2H), 3.33-3.24 (m, 1H), 2.90-2.79 (m, 4H). MS m/z (ESI): 479.8 [M + H]$^+$. |
| C8 | 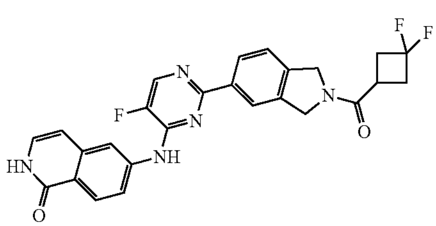 [SMILES: O=C(C1CC(F)(F)C1)N1Cc2ccc(-c3ncc(F)c(Nc4ccc5c(=O)[nH]ccc5c4)n3)cc2C1] | 6-((2-(2-(3,3-difluoroo-cyclobutane-1-carbonyl)isoindolin-5-yl)-5-fluoro-pyrimidin-4-yl)amino)isoquinolin-1(2H)-one | $H_2N$-pyrimidine-Cl in Step 4 was replaced with F-pyrimidine-$NH_2$-Cl. | $^1$H NMR (400 MHz, DMSO-$d_6$) δ 11.13 (d, J = 4.0 Hz, 1H), 10.03 (s, 1H), 8.57 (d, J = 4.0 Hz, 1H), 8.27-8.19 (m, 4H), 7.95 (q, J = 8.0 Hz, 1H), 7.49 (q, J = 8.0 Hz, 1H), 7.18 (q, J = 8.0 Hz, 1H), 6.50 (dd, J = 8.0, 4.0 Hz, 1H), 4.89 (d, J = 12.0 Hz, 2H), 4.75 (d, |

| No. | Compound Structure | Compound Name | Starting material or regent different from that in Example 3 | Characterization Data |
|---|---|---|---|---|
| | | | | J = 16.0 Hz, 2H), 3.33-3.26 (m, 1H), 2.89-2.83 (m, 4H). MS m/z (ESI): 491.6 [M + H]+. |
| C12 | 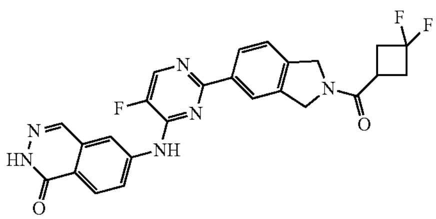 [SMILES: O=C(C1CC(F)(F)C1)N1Cc2ccc(-c3ncc(F)c(Nc4ccc5c(=O)[nH]ncc5c4)n3)cc2C1] | 6-((2-(2-(3,3-difluoroo-cyclobutane-1-carbonyl) isoindolin-5-yl)-5-fluoro-pyrimidin-4-yl)amino) phthalazin-1(2H)-one | in Step 4 was replaced with ; in Step 5 was replaced with | 1H NMR (400 MHz, DMSO-d6) δ 12.56 (s, 1H), 10.28 (s, 1H), 8.63 (d, J = 4.0 Hz, 1H), 8.50 (d, J = 24.0 Hz, 1H), 8.37 (d, J = 4.0 Hz, 1H), 8.29-8.23 (m, 3H), 7.52 (q, J = 8.0 Hz, 1H), 4.90 (d, J = 16.0 Hz, 2H), 4.76 (d, J = 16.0 Hz, 2H), 3.28-3.24 (m, 1H), 2.89-2.83 (m, 4H). MS m/z (ESI): 493.1 [M + H]+. |

Example 4: Preparation of 3,3-difluorocyclobutyl 5-(5-fluoro-4-((1-oxo-1,2-dihydroisoquinolin-6-yl) amino)pyrimidin-2-yl)isoindoline-2-carboxylate (C10) and 6-((5-fluoro-2-(2-(4,4,4-trifluoro-3-methylbutanoyl)isoindolin-5-yl)pyrimidin-4-yl)amino) isoquinolin-1(2H)-one (C37)

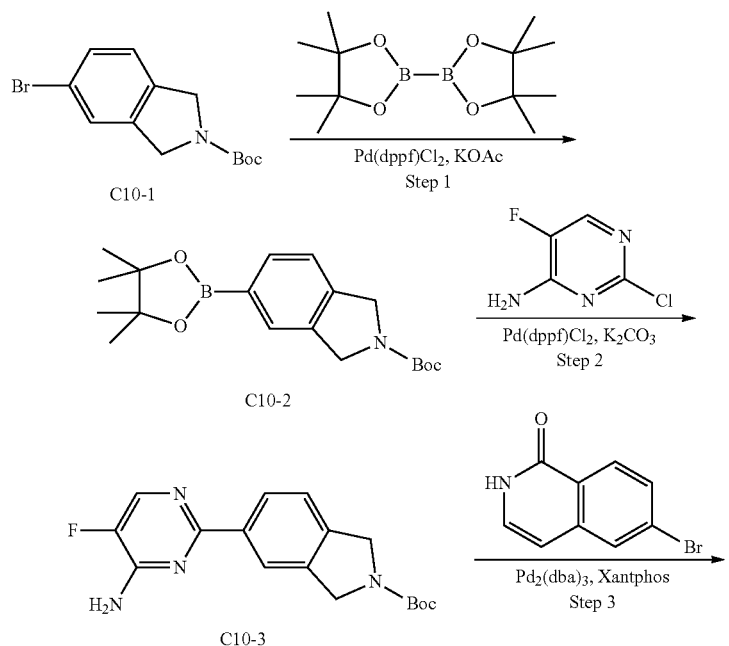

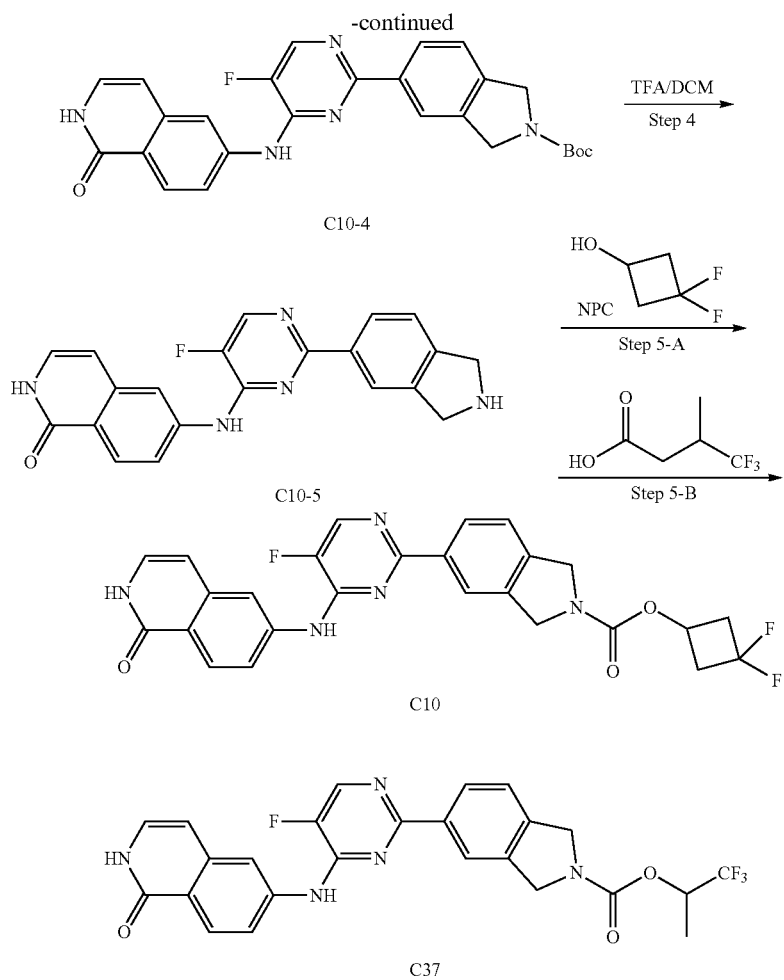

Step 1:

Compound C10-1 (46 g, 0.15 mol) and bis(pinacolato)diboron (46 g, 0.18 mol) were dissolved in N,N-dimethylformamide (800 mL), potassium acetate (46 g, 0.47 mol) and Pd(dppf)Cl$_2$ (10 g, 14 mmol) were added, purge with nitrogen was performed for three times, and the reaction solution was stirred at 110° C. for 16 hours. LC-MS indicated the reaction was complete. The reaction solution was cooled to room temperature, and the reaction solvent was removed by rotary evaporation in vacuum. The residue was separated and purified by column chromatography on silica gel (petroleum ether:ethyl acetate=20:1~5:1), to afford compound C10-2 (37 g, white solid, 66% yield).

$^1$H NMR (400 MHz, CDCl$_3$) δ 7.67-7.72 (m, 2H), 7.22-7.29 (m, 1H), 4.62-4.69 (m, 4H), 1.52 (s, 9H), 1.35 (s, 12H). MS m/z (ESI): 367.9 [M+Na]$^+$.

Step 2:

Compound C10-2 (1.0 g, 2.90 mmol) and 2-chloro-5-fluoropyrimidin-4-amine (427 mg, 2.89 mmol) were dissolved in 1,4-dioxane (30 mL), water (3 mL), potassium carbonate (1.2 g, 8.7 mmol) and Pd(dppf)Cl$_2$ (636 mg, 0.87 mmol) were added, purge with nitrogen was performed for three times, and the reaction solution was stirred at 110° C. for 16 hours. LC-MS indicated the reaction was complete. The reaction solution was cooled to room temperature, and concentrated under reduced pressure to remove the solvent. The residue was separated and purified by column chromatography on silica gel (petroleum ether:ethyl acetate=20:1~5:1), to afford compound C10-3 (700 mg, white solid, yield 66%).

$^1$H NMR (400 MHz, DMSO-d$_6$) δ 8.25 (d, J=3.3 Hz, 1H), 8.19-8.12 (m, 2H), 7.40 (s, 1H), 7.34 (s, 2H), 4.63 (d, J=8.7 Hz, 5H), 1.07 (s, 10H). MS m/z (ESI): 330.9 [M+H]$^+$.

Step 3:

Compound C10-3 (560 mg, 1.7 mmol) and 6-bromoisoquinolin-1(2H)-one (380 mg, 0.18 mol) were dissolved in 1,4-dioxane (20 mL), cesium carbonate (1.66 g, 5.09 mmol), Pd$_2$(dba)$_3$ (62 mg, 0.68 mmol) and Xantphos (1.18 g, 2.03 mmol) were added, purge with nitrogen was performed for three times, and the reaction solution was stirred at 110° C. for 16 hours. LC-MS indicated the reaction was complete. The reaction solution was cooled to room temperature, filtered, and the reaction solvent was removed by rotary evaporation invacuum, to afford compound C10-4 (340 mg, yellow solid, yield 66%).

MS m/z (ESI): 473.8 [M+H]$^+$.

Step 4:

Compound C10-4 (340 mg, 0.72 mmol) was dissolved in dichloromethane (10 mL), trifluoroacetic acid (5 mL) was added, and the reaction solution was stirred at room temperature for 3 hours. LC-MS indicated the reaction was complete. The reaction solution was cooled to room temperature, and the reaction solvent was removed by rotary evaporation in vacuum, to afford compound a crude product of C10-5 (500 mg, yellow solid).

MS m/z (ESI): 374.1 [M+H]⁺.

Step 5-A:

3,3-difluorocyclobutanol (32 mg, 0.29 mmol) and bis(4-nitrophenyl)carbonate (81 mg, 0.27 mmol) were dissolved in N,N-dimethylformamide (10 mL), triethylamine (162 mg, 1.61 mmol) was added, and the reaction solution was stirred at room temperature for 2 h. Compound C10-5 (100 mg, 0.27 mol) was added, and the reaction solution was further stirred at room temperature for 16 hours. LC-MS indicated the reaction was complete. The reaction solution was cooled to room temperature, and the reaction solvent was removed by rotary evaporation in vacuum. The residue was separated and purified by preparative chromatography, to afford compound C10 (12.32 mg, yellow solid, yield 9%).

¹H NMR (400 MHz, DMSO-d₆) δ 11.14 (s, 1H), 10.04 (s, 1H), 8.58 (s, 1H), 8.33-8.16 (m, 4H), 7.95 (dd, J=20.3, 8.6 Hz, 1H), 7.50 (s, 1H), 7.21-7.16 (m, 1H), 6.52 (d, J=6.8 Hz, 1H), 4.92 (s, 1H), 4.75 (dd, J=22.6, 13.7 Hz, 4H), 3.13-3.05 (m, 2H), 2.82-2.72 (m, 2H). MS m/z (ESI): 507.8 [M+H]⁺.

Step 5-B:

Compound C10-5 (100 mg, 0.268 mmol) and HATU (112 mg, 0.295 mmol) were dissolved in N,N-dimethylformamide (5 mL), 4,4,4-trifluoro-3-methylbutanoic acid (42 mg, 0.268 mmol) and diisopropylethylamine (173 mg, 1.339 mmol) were added, and the reaction was stirred at room temperature for 16 hours. The reaction solution was added with water (10 mL), extracted with dichloromethane (20 mL×3), the organic phase was concentrated under reduced pressure, and then the resulting residue was purified by preparative HPLC, to afford compound C37 (90.15 mg, white solid, yield 65%).

¹H NMR (400 MHz, DMSO-d₆) δ 11.14 (s, 1H), 10.05 (s, 1H), 8.60 (s, 1H), 8.31-8.20 (m, 4H), 7.96 (dd, J=25.8, 9.0 Hz, 1H), 7.55-7.46 (m, 1H), 7.23-7.13 (m, 1H), 6.52 (t, J=6.1 Hz, 1H), 4.97 (t, J=9.3 Hz, 2H), 4.76 (d, J=16.8 Hz, 2H), 2.93 (s, 1H), 2.83-2.62 (m, 2H), 1.16 (d, J=6.7 Hz, 3H). MS m/z (ESI): 511.6 [M+H]⁺.

The compounds in the following Table were prepared according to methods similar to that described in Example 4.

| No. | Compound Structure | Compound Name | Starting material or regent from that in Example 4 | Characterization Data |
|---|---|---|---|---|
| C11 | (structure) | tert-butyl 5-(5-fluoro-4-((1-oxo-1,2-dihydro-isoquinolin-6-yl)amino)pyrimidin-2-yl)isoindoline-2-carboxylate | i.e., Intermediate C10-4 | ¹H NMR (400 MHz, DMSO-d₆) δ 11.15 (s, 1H), 10.04 (s, 1H), 8.59 (d, J = 3.3 Hz, 1H), 8.25 (dd, J = 31.2, 18.0 Hz, 3H), 7.95 (dd, J = 23.7, 8.4 Hz, 1H), 7.49 (s, 1H), 7.19 (s, 1H), 6.53 (d, J = 5.5 Hz, 2H), 4.66 (d, J = 13.7 Hz, 4H), 1.48 (s, 9H). MS m/z (ESI): 473.7 [M + H]⁺. |
| C14 | (structure) | 3,3-difluoro-cyclobutyl 5-(5-fluoro-4-((1-oxo-1,2,3,4-tetrahydro-isoquinolin-6-yl)amino)pyrimidin-2-yl)isoindoline-2-carboxylate | in Step 3 was replaced with (structure); and Step 5-B was omitted. | ¹H NMR (400 MHz, DMSO-d₆) δ 9.92 (s, 1H), 8.56 (s, 1H), 8.23 (d, J = 8.4 Hz, 2H), 7.95-7.83 (m, 3H), 7.53-7.46 (m, 1H), 4.92 (s, 1H), 4.74 (dd, J = 22.7, 12.9 Hz, 4H), 3.42 (s, 2H), 3.09 (s, 2H), 2.96 (s, 2H), 2.82-2.71 (m, 2H). MS m/z (ESI): 509.5 [M + H]⁺. |

-continued

| No. | Compound Structure | Compound Name | Starting material or regent from that in Example 4 | Characterization Data |
|---|---|---|---|---|
| C17 | 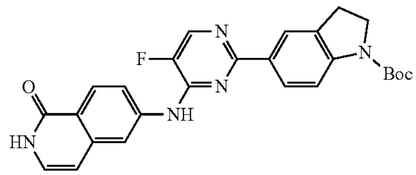 [SMILES: CC(C)(C)OC(=O)N1CCc2cc(-c3ncc(F)c(Nc4ccc5c(=O)[nH]ccc5c4)n3)ccc21] | tert-butyl 5-(5-fluoro-4-((1-oxo-1,2-dihydro-isoquinolin-6-yl)amino)pyrimidin-2-yl)indoline-2-carboxylate | in Step 1 was replaced with ; and Step 4, Step 5-A and Step 5-B were omitted. | $^1$H NMR (400 MHz, DMSO-$d_6$) δ 11.12 (d, J = 4.0 Hz, 1H), 9.96 (s, 1H), 8.51 (d, J = 4.0 Hz, 1H), 8.32 (s, 1H), 8.22-8.08 (m, 3H), 7.89 (d, J = 8.0 Hz, 1H), 7.17 (t, J = 8.0 Hz, 1H), 6.49 (d, J = 8.0 Hz, 1H), 3.97 (t, J = 8.0 Hz, 2H), 3.15 (t, J = 8.0 Hz, 2H), 1.52 (s, 9H). MS m/z (ESI): 474.1 [M + H]$^+$. |
| C16 | 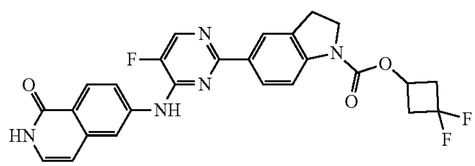 [SMILES: O=C(OC1CC(F)(F)C1)N1CCc2cc(-c3ncc(F)c(Nc4ccc5c(=O)[nH]ccc5c4)n3)ccc21] | 3,3-difluoro-cyclobutyl 5-(5-fluoro-4-((1-oxo-1,2-dihydro-isoquinolin-6-yl)amino)pyrimidin-2-yl)indoline-2-carboxylate | in Step 1 was replaced with ; and Step 5-B was omitted. | $^1$H NMR (400 MHz, DMSO-$d_6$) δ 11.13 (s, 1H), 9.99 (s, 1H), 8.53 (d, J = 3.3 Hz, 1H), 8.31 (s, 1H), 8.19-8.14 (m, 2H), 7.91 (s, 1H), 7.82 (s, 1H), 7.22-7.14 (m, 1H), 6.50 (d, J = 8.0 Hz, 1H), 5.00 (s, 1H), 4.12-3.99 (m, 2H), 3.24-3.04 (m, 4H), 2.95-2.74 (m, 2H). MS m/z (ESI): 507.5 [M + H]$^+$. |
| C18 | 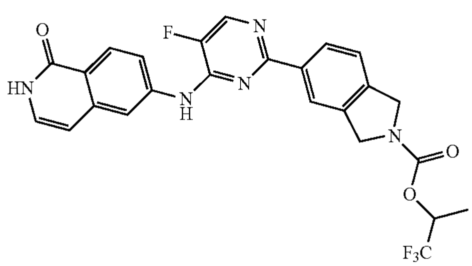 [SMILES: CC(OC(=O)N1Cc2ccc(-c3ncc(F)c(Nc4ccc5c(=O)[nH]ccc5c4)n3)cc2C1)C(F)(F)F] | 1,1,1-trifluoro-propan-2-yl 5-(5-fluoro-4-((1-oxo-1,2-dihydro-isoquinolin-6-yl)amino)pyrimidin-2-yl)isoindoline-2-carboxylate | in Step 5-A was replaced with ; and Step 5-B was omitted. | $^1$H NMR (400 MHz, DMSO-$d_6$) δ 11.14 (s, 1H), 10.04 (s, 1H), 8.60 (s, 1H), 8.30-8.20 (m, 5H), 8.01-7.91 (m, 1H), 7.52 (s, 1H), 7.21-7.17 (m, 1H), 6.52 (s, 1H), 4.78 (d, J = 16.2 Hz, 4H), 1.43 (d, J = 6.4 Hz, 3H). MS m/z (ESI): 513.7 [M + H]$^+$. |

| No. | Compound Structure | Compound Name | Starting material or regent from that in Example 4 | Characterization Data |
|---|---|---|---|---|
| C19 | 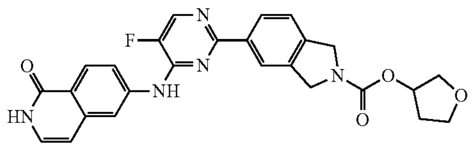 [SMILES: O=C(OC1CCOC1)N1Cc2ccc(-c3ncc(F)c(Nc4ccc5c(=O)[nH]ccc5c4)n3)cc2C1] | tetrahydrofuran-3-yl 5-(5-fluoro-4-((1-oxo-1,2-dihydroisoquinolin-6-yl)amino)pyrimidin-2-yl)isoindoline-2-carboxylate | in Step 5-A was replaced with and Step 5-B was omitted. | 1H NMR (400 MHz, DMSO-d₆) δ 11.13 (s, 1H), 10.04 (s, 1H), 8.58 (s, 1H), 8.31-8.18 (m, 4H), 7.95 (d, J = 12.1 Hz, 1H), 7.50 (s, 1H), 7.18 (s, 1H), 6.50 (s, 1H), 5.23 (s, 1H), 4.72 (d, J = 15.7 Hz, 4H), 3.84 (d, J = 9.1 Hz, 2H), 3.78-3.75 (m, 2H), 2.01 (s, 2H). MS m/z (ESI): 487.8 [M + H]⁺. |
| C24 | 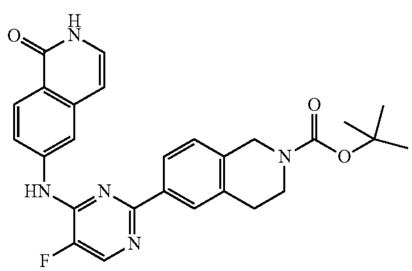 [SMILES: CC(C)(C)OC(=O)N1CCc2cc(-c3ncc(F)c(Nc4ccc5c(=O)[nH]ccc5c4)n3)ccc2C1] | tert-butyl 6-(5-fluoro-4-((1-oxo-1,2-dihydroisoquinolin-6-yl)amino)pyrimidin-2-yl)-3,4-dihydroisoquinolin-2(1H)-carboxylate | in Step 1 was replaced with and Step 4, Step 5-A and Step 5-B were omitted. | ¹H NMR (400 MHz, DMSO-d₆) δ 11.15 (s, 1H), 10.04 (s, 1H), 8.57 (d, J = 3.1 Hz, 1H), 8.35 (s, 1H), 8.18 (d, J = 8.6 1H), 8.12 (s, 2H), 7.89 (d, J = 8.7 Hz, 1H), 7.33 (d, J = 8.5 Hz, 1H), 7.19 (t, J = 6.3 Hz, 1H), 6.51 (d, J = 6.8 Hz, 1H), 4.57 (s, 2H), 3.61 (s, 2H), 2.90 (s, 2H), 1.45 (s, 9H). MS m/z (ESI): 487.8 [M + H]⁺. |
| C23 | 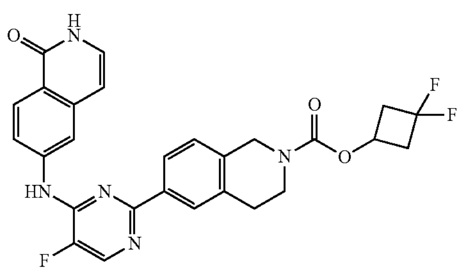 [SMILES: O=C(OC1CC(F)(F)C1)N1CCc2cc(-c3ncc(F)c(Nc4ccc5c(=O)[nH]ccc5c4)n3)ccc2C1] | 3,3-difluorocyclobutyl 6-(5-fluoro-4-((1-oxo-1,2-dihydroisoquinolin-6-yl)amino)pyrimidin-2-yl)-3,4-dihydroisoquinolin-2(1H)-carboxylate | in Step 1 was replaced with and Step 5-B was omitted. | ¹H NMR (400 MHz, DMSO-d₆) δ 11.12 (d, J = 5.2 Hz, 1H), 10.01 (s, 1H), 8.55 (s, 1H), 8.32 (s, 1H), 8.18 (d, J = 8.7 Hz, 1H), 8.11 (s, 2H), 7.89 (d, J = 8.7 Hz, 1H), 7.34 (d, J = 6.7 Hz, 1H), 7.18 (t, J = 6.3 Hz, 1H), 6.49 (d, J = 7.2 Hz, 1H), 4.94-4.82 (m, 1H), 4.63 (d, J = 25.8 Hz, 2H), 3.67 (s, 2H), 3.04 (dq, J = 11.8, 7.5 Hz, 2H), 2.92 (s, 2H), 2.73 (ddd, J = 19.5, 14.2, 4.8 Hz, 2H). MS m/z (ESI): 521.7 [M + H]⁺. |

| No. | Compound Structure | Compound Name | Starting material or regent from that in Example 4 | Characterization Data |
|---|---|---|---|---|
| C25 | 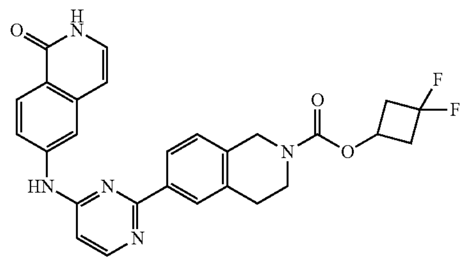 [SMILES: O=C(OC1CC(F)(F)C1)N1CCc2cc(-c3nccc(Nc4ccc5c(=O)[nH]ccc5c4)n3)ccc2C1] | 3,3-difluorocyclobutyl 6-(4-((1-oxo-1,2-dihydroisoquinolin-6-yl)amino)pyrimidin-2-yl)-3,4-dihydroisoquinolin-2(1H)-carboxylate | in Step 1 was replaced with ; in Step 2 was replaced with ; and Step 5-B was omitted. | $^1$H NMR (400 MHz, DMSO-$d_6$) δ 11.13 (s, 1H), 10.54 (s, 1H), 8.47 (d, J = 6.0 Hz, 1H), 8.20 (m, 4H), 7.71 (d, J = 8.6 Hz, 1H), 7.41 (d, J = 7.2 Hz, 1H), 7.19 (t, J = 6.0 Hz, 1H), 6.91 (d, J = 6.0 Hz, 1H), 6.51 (d, J = 7.1 Hz, 1H), 4.93-4.83 (m, 1H), 4.73-4.59 (m, 2H), 3.68 (s, 2H), 3.12-2.99 (m, 2H), 2.98-2.88 (m, 2H), 2.82-2.63 (m, 2H). MS m/z (ESI): 503.8 [M + H]$^+$. |
| C26 | 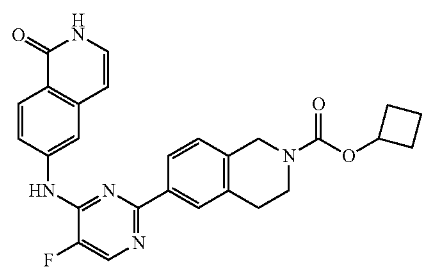 [SMILES: O=C(OC1CCC1)N1CCc2cc(-c3ncc(F)c(Nc4ccc5c(=O)[nH]ccc5c4)n3)ccc2C1] | cyclobutyl 6-(5-fluoro-4-((1-oxo-1,2-dihydroisoquinolin-6-yl)amino)pyrimidin-2-yl)-3,4-dihydroisoquinolin-2(1H)-carboxylate | in Step 1 was replaed with ; in Step 5-A was replaced with ; and Step 5-B was omitted. | $^1$H NMR (400 MHz, DMSO-$d_6$) δ 11.12 (d, J = 5.1 Hz, 1H), 10.01 (s, 1H), 8.55 (d, J = 3.0 Hz, 1H), 8.33 (s, 1H), 8.18 (d, J = 8.8 Hz, 1H), 8.10 (d, J = 5.4 Hz, 2H), 7.89 (d, J = 8.8 Hz, 1H), 7.33 (d, J = 8.5 Hz, 1H), 7.18 (t, J = 6.3 Hz, 1H), 6.49 (d, J = 7.0 Hz, 1H), 4.88 (d, J = 7.4 Hz, 1H), 4.59 (s, 2H), 3.64 (s, 2H), 2.90 (s, 2H), 2.32-2.20 (m, 2H), 2.10-1.96 (m, 2H), 1.78-1.66 (m, 1H), 1.63-1.49 (m, 1H). MS m/z (BSI): 485.8 [M + H]$^+$. |
| C30 | 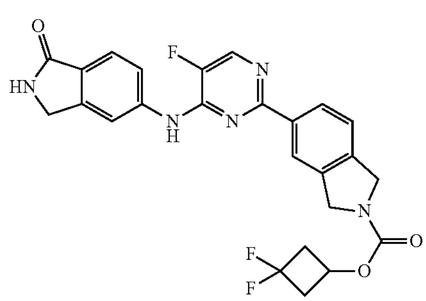 [SMILES: O=C1NCc2cc(Nc3nc(-c4ccc5c(c4)CN(C(=O)OC4CC(F)(F)C4)C5)ncc3F)ccc21] | 3,3-difluorocyclobutyl 5-(5-fluoro-4-((1-oxo-isoindolin-5-yl)amino)pyrimidin-2-yl)isoindoline-2-carboxylate | in Step 3 was replaced with ; and Step 5-B was omitted. | $^1$H NMR (400 MHz, DMSO-$d_6$) δ 9.98 (s, 1H), 8.55 (s, 1H), 8.43 (s, 1H), 8.20 (dd, J = 16.0, 8.8 Hz, 3H), 7.94 (dd, J = 14.2, 8.2 Hz, 1H), 7.71 (d, J = 8.0 Hz, 1H), 7.48 (d, J = 5.8 Hz, 1H), 4.91 (s, 1H), 4.73 (dd, J = 22.4, 13.5 Hz, 4H), 4.43 (s, 2H), 3.12- |

| No. | Compound Structure | Compound Name | Starting material or regent from that in Example 4 | Characterization Data |
|---|---|---|---|---|
| | | | | 3.07 (m, 2H), 2.83-2.70 (m, 2H). MS m/z (ESD: 495.5 [M + H]⁺. |
| C31 | 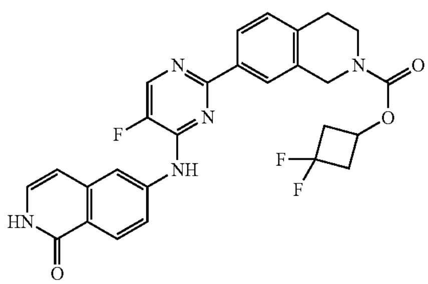 [SMILES: O=C(OC1CC(F)(F)C1)N1CCc2ccc(-c3ncc(F)c(Nc4ccc5c(=O)[nH]ccc5c4)n3)cc2C1] | 3,3-difluoro-cyclobutyl 7-(5-fluoro-4-((1-oxo-1,2-dihydro-isoquinolin-6-yl)amino)pyrimidin-2-yl)-3,4-dihydro-isoquinolin-2(1H)-carboxylate | in Step 1 was replaced with and Step 5-B was omitted. | ¹H NMR (400 MHz, DMSO-d₆) δ 11.13 (d, J = 4.8 Hz, 1H), 10.03 (s, 1H), 8.57 (d, J = 2.6 Hz, 1H), 8.35 (s, 1H), 8.19 (d, J = 8.7 Hz, 1H), 8.10 (s, 2H), 7.90 (s, 1H), 7.34 (d, J = 8.0 Hz, 1H), 7.17 (s, 1H), 6.51 (d, J = 6.8 Hz, 1H), 4.91-4.84 (m, 1H), 4.68 (d, J = 31.0 Hz, 2H), 3.66 (s, 2H), 3.06 (s, 2H), 2.89 (s, 2H), 2.76 (s, 2H). MS m/z (ESD: 521.8 [M + H]⁺. |
| C35 | 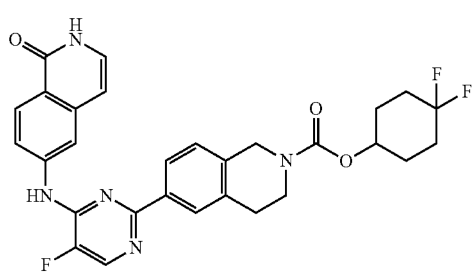 [SMILES: O=C(OC1CCC(F)(F)CC1)N1CCc2cc(-c3ncc(F)c(Nc4ccc5c(=O)[nH]ccc5c4)n3)ccc2C1] | 4,4-difluoro-cyclobutyl 6-(5-fluoro-4-((1-oxo-1,2-dihydro-isoquinolin-6-yl)amino)pyrimidin-2-yl)-3,4-dihydro-isoquinolin-2(1H)-carboxylate | in Step 1 was replaced with ; in Step 5-A was replaced with ; and Step 5-B was omitted. | ¹H NMR (400 MHz, DMSO-d₆) δ 11.13 (s, 1H), 10.02 (s, 1H), 8.59-8.54 (m, 1H), 8.33 (s, 1H), 8.18 (d, J = 8.7 Hz, 1H), 8.11 (s, 2H), 7.89 (d, J = 9.0 Hz 1H), 7.36 (d, J = 7.8 Hz, 1H), 7.18 (t, J = 6.3 Hz, 1H), 6.49 (d, J = 6.8 Hz, 1H), 4.88-4.80 (m, 1H), 4.70-4.56 (m, 3H), 3.66 (s, 2H), 2.96-2.87 (m, 2H), 2.12-1.90 (m, 4H), 1.90-1.72 (m, 4H). MS [M + H]⁺. |

-continued

| No. | Compound Structure | Compound Name | Starting material or regent from that in Example 4 | Characterization Data |
|---|---|---|---|---|
| C39 | 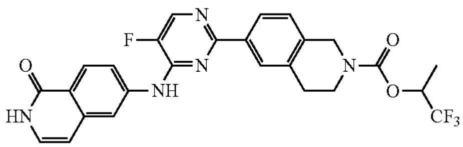 [SMILES: CC(OC(=O)N1CCc2cc(-c3ncc(F)c(Nc4ccc5c(=O)[nH]ccc5c4)n3)ccc2C1)C(F)(F)F] | 1,1,1-trifluoropropan-2-yl 6-(5-fluoro-4-((1-oxo-1,2-dihydroisoquinolin-6-yl)amino)pyrimidin-2-yl)-3,4-dihydroisoquinolin-2(1H)-carboxylate | Br—[isoindoline]—Boc in Step 1 was replaced with Br—[tetrahydroisoquinoline]—Boc ; HO—[cyclobutane with 2F] in Step 5-A was replaced with HO—CH(CH₃)—CF₃; and Step 5-B was omitted. | $^1$H NMR (400 MHz, DMSO-$d_6$) δ 11.13 (d, J = 4.9 Hz, 1H), 10.03 (s, 1H), 8.56 (s, 1H), 8.33 (s, 1H), 8.18 (d, J = 8.6 Hz, 1H), 8.11 (d, J = 5.9 Hz, 2H), 7.89 (d, J = 8.8 Hz, 1H), 7.37 (d, J = 8.2 Hz, 1H), 7.18 (t, J = 6.2 Hz, 1H), 6.50 (d, J = 7.0 Hz, 1H), 5.47-5.32 (m, 1H), 4.69-4.61 (m, 2H), 3.68 (s, 2H), 2.94 (s, 2H), 1.39 (d, J = 6.5 Hz, 3H). MS m/z (ESI): 527.6 [M + H]$^+$. |

| No. | Compound Structure | Compound Name | Starting material or regent from that in Example 4 | Characterization Data |
|---|---|---|---|---|
| C40 | 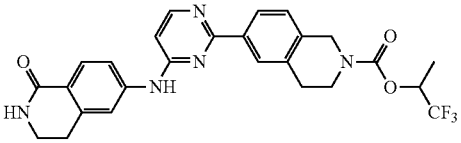 [SMILES: CC(OC(=O)N1CCc2cc(-c3nccc(Nc4ccc5c(c4)CCNC5=O)n3)ccc2C1)C(F)(F)F] | 1,1,1-trifluoro-propan-2-yl 6-(4-((1-oxo-1,2,3,4-tetrahydro-isoquinolin-6-yl)amino)pyrimidin-2-yl)-3,4-dihydro-isoquinolin-2(1H)-carboxylate | (see structures at right) | $^1$H NMR (400 MHz, DMSO-d$_6$) δ 9.98 (s, 1H), 8.44 (d, J = 5.8 Hz, 1H), 8.18 (d, J = 4.9 Hz, 2H), 7.92 (s, 1H), 7.85 (d, J = 8.4 Hz, 1H), 7.77 (s, 1H), 7.65 (d, J = 8.0 Hz, 1H), 7.37 (d, J = 8.5 Hz, 1H), 6.80 (d, J = 5.8 Hz, 1H), 5.43-5.35 (m, 1H), 4.66 (s, 2H), 3.69 (s, 2H), 2.95 (s, 4H), 1.40 (d, J = 6.6 Hz, 3H), 1.00 (d, J = 6.5 Hz, 2H). MS m/z (ESI): 512.1 [M + H]$^+$. |

-continued

| No. | Compound Structure | Compound Name | Starting material or regent from that in Example 4 | Characterization Data |
|---|---|---|---|---|
| C41 | 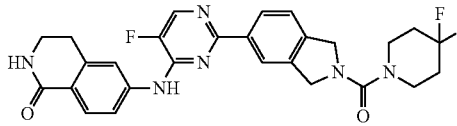 | 6-((2-(2-(4,4-difluoro-piperidine-1-carbonyl)isoindolin-5-yl)-5-fluoro-pyrimidin-4-yl)amino)-3,4-dihydro-isoquinolin-1(2H)-one | 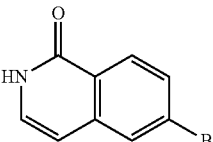<br>in Step 3 was replaced with<br>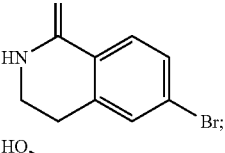<br>in Step 5-A was replaced with<br>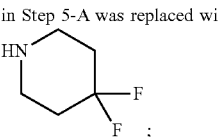<br>and Step 5-B was omitted. s | $^1$H NMR (400 MHz, DMSO-$d_6$) δ 9.91 (s, 1H), 8.55 (d, J = 3.5 Hz, 1H), 8.24-8.18 (m 2H), 7.90 (d, J = 7.6 Hz, 3H), 7.83 (s, 1H), 7.46 (d, J = 8.4 Hz, 1H), 4.82 (d, J = 9.9 Hz, 4H), 3.46-3.39 (m, 6H), 2.96 (t, J = 6.5 Hz, 2H), 2.04 (dd, J = 17.1, 11.6 Hz, 4H). MS m/z (ESI): 522.9 [M + H]$^+$. |
| C44 | 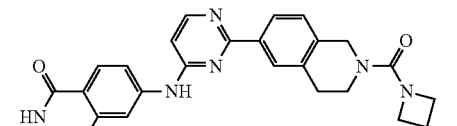 | 6-((2-(2-(3,3-difluoro-azetidine-1-carbonyl)-1,2,3,4-tetrahydro-isoquinolin-6-yl)pyrimidin-4-yl)amino)isoquinolin-1(2H)-one | 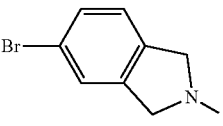<br>in Step 1 was replaed with<br>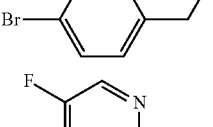<br>in Step 2 was replaced with<br>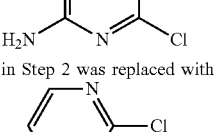<br>in Step 5-A was replaced with<br>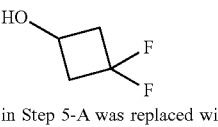<br>and Step 5-B was omitted. | $^1$H NMR (400 MHz, DMSO-$d_6$) δ 11.12 (d, J = 5.3 Hz, 1H), 10.37 (s, 1H), 8.47 (d, J = 6.1 Hz, 1H), 8.25 (d, J = 1.8 Hz, 1H), 8.21-8.14 (m, 3H), 7.71 (dd, J = 8.8, 2.1 Hz, 1H), 7.43-7.37 (m, 1H), 7.21-7.15 (m, 1H), 6.89 (d, J = 6.1 Hz, 1H), 6.50 (d, J = 7.1 Hz, 1H), 4.55 (s, 2H), 4.41 (t, J = 13.0 Hz, 5H), 3.57 (t, J = 5.8 Hz, 2H), 2.94 (t, J = 5.6 Hz, 2H). MS m/z (ESI): 488.7 [M + H]$^+$. |

-continued

| No. | Compound Structure | Compound Name | Starting material or regent from that in Example 4 | Characterization Data |
|---|---|---|---|---|
| C66 | 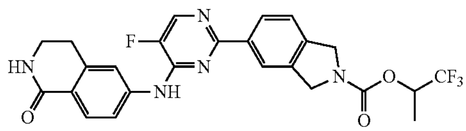 | 1,1,1-trifluoro-propan-2-yl 5-(5-fluoro-4-((1-oxo-1,2,3,4-tetrahydro-isoquinolin-6-yl)amino)pyrimidin-2-yl)isoindolin-2-carboxylate | in Step 3 was replaed with ; and in Step 5-A was replaced with ; and Step 5-B was omitted. | $^1$H NMR (400 MHz, DMSO-$d_6$) δ 9.91 (s, 1H), 8.56 (d, J = 3.4 Hz, 1H), 8.24 (d, J = 8.0 Hz, 2H), 7.95-7.81 (m, 4H), 7.50 (d, J = 7.7 Hz 1H) 5.44-5.39 m 1H) 4.78 (t, J = 12.3 Hz, 4H), 3.42 (d, J = 3.0 Hz, 2H), 2.98-2.93 (m, 2H), 1.47-1.40 (m, 3H). MS m/z (ESI): 516.0 [M + H]$^+$. |
| C72 | 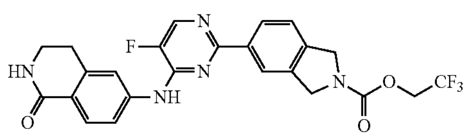 [SMILES: O=C1NCCc2cc(Nc3nc(-c4ccc5c(c4)CN(C(=O)OCC(F)(F)F)C5)ncc3F)ccc21] | 2,2,2-trifluoro-ethyl 5-(5-fluoro-4-((1-oxo-1,2-dihydro-isoquinolin-6-yl)amino)pyrimidin-2-yl)isoindolin-2-carboxylate | in Step 5-A was replaced with ; and Step 5-B was omitted. | $^1$H NMR (400 MHz, DMSO-$d_6$) δ 11.14 (s, 1H), 10.04 (s, 1H), 8.59 (d, J = 3.6 Hz, 1H), 8.31-8.25 (m, 3H), 8.24-8.19 (m, 1H), 7.98-7.89 (m, 1H), 7.52 (d, J = 8.0 Hz, 1H), 7.18 (dd, J = 13.7, 7.8 Hz, 1H), 6.52 (d, J = 7.1 Hz, 1H), 4.80 (dd, J = 13.9, 7.0 Hz, 6H). MS m/z (ESI): 499.6 [M + H]$^+$. |
| C73 | 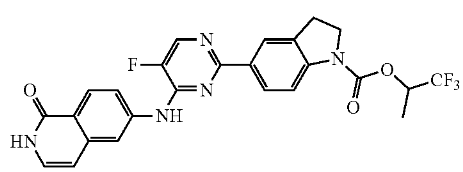 [SMILES: CC(OC(=O)N1CCc2cc(-c3ncc(F)c(Nc4ccc5c(=O)[nH]ccc5c4)n3)ccc21)C(F)(F)F] | 1,1,1-trifluoro-propan-2-yl 5-(5-fluoro-4-((1-oxo-1,2-dihydro-isoquinolin-6-yl)amino)pyrimidin-2-yl)indoline-1-carboxylate | in Step 1 was replaced with ; in Step 5-A was replaced with ; and Step 5-B was omitted. | $^1$H NMR (400 MHz, DMSO-$d_6$) δ 11.14 (s, 1H), 10.00 (s, 1H), 8.55 (d, J = 3.5 Hz, 1H), 8.31 (s, 1H), 8.23-8.16 (m, 3H), 7.93-7.84 (m, 1H), 7.25-7.16 (m, 1H), 6.51 (d, J = 6.9 Hz, 1H), 5.52 (s, 1H), 4.07 (t, J = 8.6 Hz, 2H), 3.23 (d, J = 8.6 Hz, 2H) 1.48 (s, 3H). MS m/z (ESI): 513.6 [M + H]$^+$. |

-continued

| No. | Compound Structure | Compound Name | Starting material or regent from that in Example 4 | Characterization Data |
|---|---|---|---|---|
| C76 | 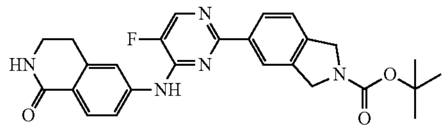 [SMILES: CC(C)(C)OC(=O)N1Cc2ccc(-c3ncc(F)c(Nc4ccc5c(c4)CCNC5=O)n3)cc2C1] | tert-butyl 5-(5-fluoro-4-((1-oxo-1,2,3,4-tetrahydro-isoquinolin-6-yl)amino)pyrimidin-2-yl)isoindoline-2-carboxylate | in Step 3 was replaced with ; and Step 4 Step 5-A and Step 5-B were omitted. | ¹H NMR (400 MHz, DMSO-d₆) δ 9.91 (s, 1H), 8.54 (d, J = 3.6 Hz, 1H), 8.22-8.20 (m, 2H), 7.96-7.82 (m, 4H), 7.47 (t, J = 7.2 Hz, 1H), 4.69-4.64 (m, 4H), 3.41-3.43 (m, 2H), 2.96-2.90 (m, 2H), 1.48 (s, 9H). MS m/z (ESI): 476.1 [M + H]⁺. |
| C78 | 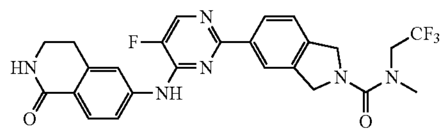 [SMILES: CN(CC(F)(F)F)C(=O)N1Cc2ccc(-c3ncc(F)c(Nc4ccc5c(c4)CCNC5=O)n3)cc2C1] | 5-(5-fluoro-4-((1-oxo-1,2,3,4-tetrahydro-isoquinolin-6-yl)amino)pyrimidin-2-yl)-N-methyl-N-(2,2,2-trifluoro-ethyl)isoindoline-2-carboxylate | in Step 3 was replaced with ; in Step 5-A was replaced with ; and Step 5-B was omitted. | ¹H NMR (400 MHz, DMSO-d₆) δ 9.91 (s, 1H), 8.55 (d, J = 3.6 Hz, 1H), 8.22 (d, J = 6.4 Hz, 2H), 7.90 (d, J = 6.9 Hz, 3H), 7.82 (s, 1H), 7.48 (d, J = 8.4 Hz, 1H), 4.81 (d, J = 11.4 Hz, 4H), 4.18 (d, J = 9.8 Hz, 2H), 3.42 (dd, J = 6.4, 4.0 Hz, 2H) 3.12 (s, 3H), 2.95 (t, J = 6.4 Hz, 2H). MS m/z (ESI): 514:7 [M + H]⁺. |
| C79 | 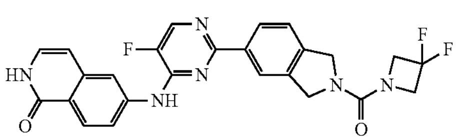 [SMILES: O=C(N1Cc2ccc(-c3ncc(F)c(Nc4ccc5c(=O)[nH]ccc5c4)n3)cc2C1)N1CC(F)(F)C1] | 6-((2-(2-(3,3-difluoro-azetidine-1-carbonyl)isoindolin-5-yl)-5-fluoro-pyrimidin-4-yl)amino)isoquinolin-1(2H)-one | in Step 5-A of Example 4 was replaced with ; and Step 5-B was omitted. | ¹H NMR (400 MHz, MeOD) δ 8.41 (d, J = 3.2 Hz, 1H), 8.34-8.30 (m, 4H), 7.96 (d, J = 8.8 Hz, 1H), 7.47 (d, J = 8.0 Hz, 1H), 7.22 (d, J = 7.2 Hz, 1H), 6.69 (d, J = 6.8 Hz, 1H), 4.89-4.83 (m, 4H), 4.51 (t, J = 12.4 Hz, 4H). MS m/z (ESI): 492.5 [M + H]⁺. |

| No. | Compound Structure | Compound Name | Starting material or regent from that in Example 4 | Characterization Data |
|---|---|---|---|---|
| C81 | 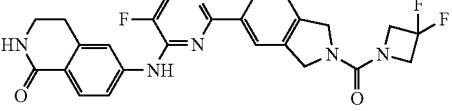 | 6-((2-(2-(3,3-difluoro-azetidine-1-carbonyl)isoindolin-5-yl)-5-fluoro-pyrimidin-4-yl)amino)-3,4-dihydro-isoquinolin-1(2H)-one | 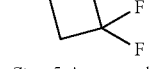 in Step 3 was replaced with 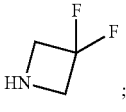 and 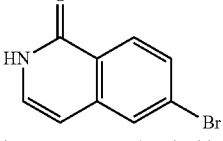 in Step 5-A was replaced with 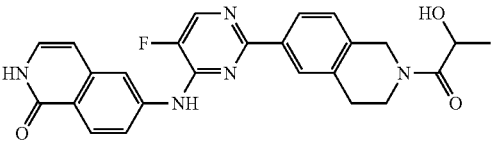 [SMILES: CC(O)C(=O)N1CCc2cc(-c3ncc(F)c(Nc4ccc5c(=O)[nH]ccc5c4)n3)ccc2C1] ; and Step 5-B was omitted. | $^1$H NMR (400 MHz, DMSO-$d_6$) δ 9.91 (s, 1H), 8.55 (d, J = 3.5 Hz, 1H), 8.23 (d, J = 8.4 Hz, 2H), 7.89 (t, J = 4.1 Hz, 3H), 7.82 (s, 1H), 7.47 (d, J = 8.2 Hz, 1H), 4.74 (d, J = 10.9 Hz, 4H), 4.45 (t, J = 13.0 Hz, 4H), 3.42 (s, 2H), 2.95 (t, J = 6.5 Hz, 2H). MS m/z (ESI): 494.6 [M + H]$^+$. |
| C36 | 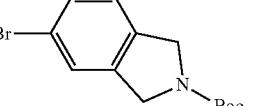 | 6-((5-fluoro-2-(2-(2-hydroxy-propanoyl)-1,2,3,4-tetrahydro-isoquinolin-6-yl)primidin-4-yl)amino)isoquinolin-1(2H)-one | 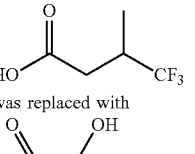 in Step 1 was replaced with 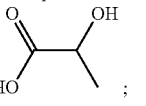 ; 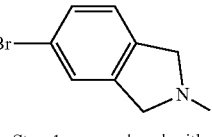 was replaced with  ; and Step 5-A was omitted. | $^1$H NMR (400 MHz, DMSO-$d_6$) δ 11.12 (d, J = 5.2 Hz, 1H), 10.02 (s, 1H), 8.56 (d, J = 3.2 Hz, 1H), 8.32 (s, 1H), 8.18 (d, J = 8.7 Hz, 1H), 8.11 (s, 2H), 7.89 (d, J = 8.9 Hz, 1H), 7.36 (d, J = 8.6 Hz, 1H), 7.18 (t, J = 6.2 Hz, 1H), 6.50 (d, J = 7.2 Hz, 1H), 4.91-4.70 (m, 1H), 4.69 (d, J = 6.8 Hz, 1H), 4.53 (d, J = 6.6 Hz, 1H), 3.81 (s, 2H), 2.90 (t, J = 28.0 Hz, 2H), 1.22 (dd, J = 14.5, 6.3 Hz, 4H). MS m/z (ESI): 459.8 [M + H]$^+$. |

| No. | Compound Structure | Compound Name | Starting material or regent from that in Example 4 | Characterization Data |
|---|---|---|---|---|
| C15 | 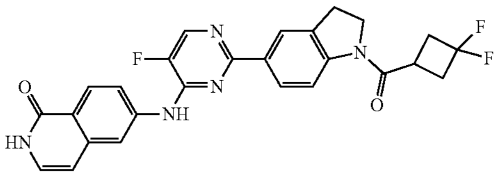 [SMILES: O=C(C1CC(F)(F)C1)N1CCc2cc(-c3ncc(F)c(Nc4ccc5c(=O)[nH]ccc5c4)n3)ccc21] | 6-((2-(1-(3,3-difluoroo-cyclobutane-1-carbonyl)indolin-5-yl)-5-fluoro-pyrimidin-4-yl)amino)isoquinolin-1-(2H)-one | Br-[indoline-Boc] in Step 1 was replaced with Br-[indoline-Boc]; and HO-CH2-CH(CH3)-CF3 in Step 5-B was replaced with HO-C(O)-[cyclobutane-F,F]; and Step 5-A was omitted. | ¹H NMR (400 MHz, DMSO-d₆) δ 11.12 (d, J = 4.0 Hz, 1H), 9.99 (s, 1H), 8.53 (d, J = 4.0 Hz, 1H), 8.31 (s, 1H), 8.24-8.07 (m, 4H), 7.90 (d, J = 8.0 Hz, 1H), 7.18 (t, J = 8.0 Hz, 1H), 6.50 (d, J = 8.0 Hz, 1H), 4.12 (t, J = 8.0 Hz, 2H), 3.41-3.31 (n, 1H), 3.24 (t, J = 8.0 Hz, 2H), 2.96-2.82 (m, 4H). MS m/z (ESI): 492.1 [M + H]⁺. |
| C48 | 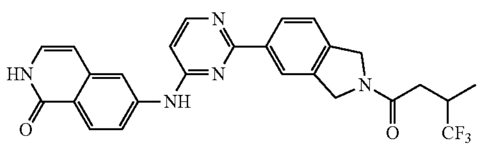 [SMILES: CC(CC(=O)N1Cc2ccc(-c3nccc(Nc4ccc5c(=O)[nH]ccc5c4)n3)cc2C1)C(F)(F)F] | 6-((2-(2-(4,4,4-trifluoro-3-methyl-butanoyl)isoindolin-5-yl)pyrimidin-4-yl)amino)isoquinolin-1(2H)-one | [F-pyrimidine-NH2-Cl] in Step 2 was replaced with [pyrimidine-NH2-Cl]; and Step 5-A was omitted. | ¹H NMR (400 MHz, DMSO-d₆) δ 13.09 (s, 1H), 10.25 (s, 1H), 8.35 (d, J = 4.9 Hz, 1H), 8.24 (d, J = 12.0 Hz, 2H), 8.14 (d, J = 8.5 Hz, 3H), 7.61 (d, J = 8.7 Hz, 1H), 7.55 (d, J = 8.8 Hz, 2H), 6.77 (s, 1H), 4.96 (d, J = 7.0 Hz, 2H), 4.76 (d, J = 11.4 Hz, 2H), 2.93 (d, J = 7.3 Hz, 1H), 2.76 (d, J = 16.4 Hz, 1H), 2.56 (s, 1H), 1.15 (d, J = 6.8 Hz, 3H). MS m/z (ESI): 494.0 [M + H]⁺. |
| C51 | 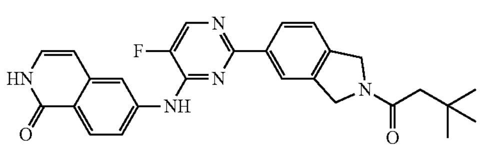 [SMILES: CC(C)(C)CC(=O)N1Cc2ccc(-c3ncc(F)c(Nc4ccc5c(=O)[nH]ccc5c4)n3)cc2C1] | 6-((2-(2-(3,3-dimethyl-butanoyl)isoindolin-5-yl)-5-fluoro-pyrimidin-4-yl)amino)isoquinolin-1(2H)-one | HO-CH2-CH(CH3)-CF3 in Step 5-B was replaced with HO-CH2-C(CH3)3; and Step 5-A was omitted. | ¹H NMR (400 MHz, DMSO-d₆) δ 11.15 (s, 1H), 10.05 (s, 1H), 8.59 (d, J = 2.9 Hz, 1H), 8.32 (d, J = 2.0 Hz, 1H), 8.26-8.19 (m, 2H), 8.00 (d, J = 8.8 Hz, 1H), 7.94-7.85 (m, 1H), 7.50 (dd, J = 12.9, 8.3 Hz, 1H), 7.22-7.16 (m, 1H), 6.52 (dd, J = 6.9, 3.8 Hz, 1H), 4.93 (d, J = 9.7 Hz, 2H), 4.72 (d, J = 17.6 Hz, 2H), 2.30 (d, J = 4.3 Hz, 2H), 1.07 (d, J = 1.4 Hz, 9H). MS m/z (ESI): 471.7 [M + H]⁺. |

-continued

| No. | Compound Structure | Compound Name | Starting material or regent from that in Example 4 | Characterization Data |
|---|---|---|---|---|
| C56 | 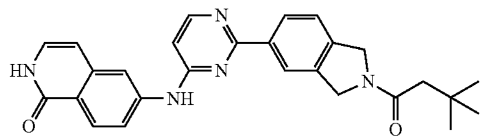 [SMILES: CC(C)(C)CC(=O)N1Cc2ccc(-c3nccc(Nc4ccc5c(=O)[nH]ccc5c4)n3)cc2C1] | 6-((2-(2-(3,3-dimethyl-butanoyl)isoindolin-5-yl)pyimidin-4-yl)amino)isoquinolin-1(2H)-one | (structures shown) in Step 2 was replaced with (structure); in Step 5-B was replaced with (structure); and Step 5-A was omitted. | $^1$H NMR (400 MHz, DMSO-$d_6$) δ 11.10 (s, 1H), 10.24 (s, 1H), 8.49 (d, J = 5.9 Hz, 1H), 8.29 (dd, J = 21.1, 10.8 Hz, 3H), 8.20 (dd, J = 8.6, 5.9 Hz, 1H), 7.77 (d, J = 37.6 Hz, 1H), 7.53 (d, J = 5.3 Hz, 1H), 7.18 (d, J = 7.0 Hz, 1H), 6.88 (d, J = 5.8 Hz, 1H), 6.52 (d, J = 7.4 Hz, 1H), 4.94 (d, J = 10.0 Hz, 2H), 4.74 (d, J = 18.1 Hz, 2H), 2.30 (d, J = 5.2 Hz, 2H), 1.07 (d, J = 1.9 Hz, 9H). MS m/z (ESI): 454.1 [M + H]$^+$. |
| C62 | 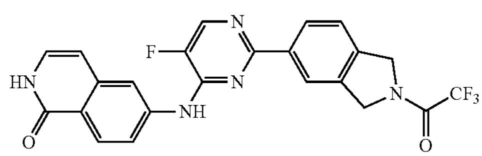 [SMILES: O=C(N1Cc2ccc(-c3ncc(F)c(Nc4ccc5c(=O)[nH]ccc5c4)n3)cc2C1)C(F)(F)F] | 6-((5-fluoro-2-(2-(2,2,2-trifluoro-butanoyl)isoindolin-5-yl)pyrimidin-4-yl)amino)isoquinolin-1(2H)-one | (structure) in Step 5-B was replaced with TFAA, and the reaction conditions were changed to employing DIPEA as the base, and DCM as the solvent; and Step 5-A was omitted. | $^1$H NMR (400 MHz, DMSO-$d_6$) δ 11.14 (s, 1H), 10.05 (s, 1H), 8.60 (d, J = 3.5 Hz, 1H), 8.25 (ddd, J = 11.5, 8.8, 5.9 Hz, 4H), 7.96 (dd, J = 17.9, 9.8 Hz, 1H), 7.56 (t, J = 8.9 Hz, 1H), 7.19 (dd, J = 13.0, 7.1 Hz, 1H), 6.52 (s, 1H), 5.14 (d, J = 13.5 Hz, 2H), 4.94 (d, J = 17.5 Hz, 2H). MS m/z (ESI): 469.6 [M + H]$^+$. |
| C63 | 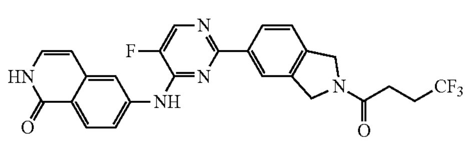 [SMILES: O=C(CCC(F)(F)F)N1Cc2ccc(-c3ncc(F)c(Nc4ccc5c(=O)[nH]ccc5c4)n3)cc2C1] | 6-((5-fluoro-2-(2-(4,4,4-trifluoro-butanoyl)isoindolin-5-yl)pyrimidin-4-yl)amino)isoquinolin-1(2H)-one | (structure) in Step 5-B was replaced with (structure); and Step 5-A was omitted. | $^1$H NMR (400 MHz, DMSO-$d_6$) δ 11.13 (s, 1H), 10.04 (s, 1H), 8.60-8.56 (m, 1H), 8.30-8.20 (m, 4H), 7.96 (dd, J = 20.6, 10.9 Hz, 1H), 7.52 (t, J = 8.7 Hz, 1H), 7.19 (dd, J = 13.4, 7.3 Hz, 1H), 6.55-6.49 (m, 1H), 4.97 (d, J = 11.1 Hz, 2H), 4.75 (d, J = 16.4 Hz, 2H), 2.73-2.67 (m, 2H), 2.61 (d, J = 11.3 Hz, 2H). MS m/z (ESI): 497.7 [M + H]$^+$. |

-continued

| No. | Compound Structure | Compound Name | Starting material or regent from that in Example 4 | Characterization Data |
|---|---|---|---|---|
| C64 | 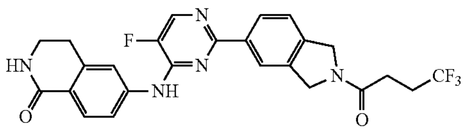 [SMILES: O=C1NCCc2cc(Nc3nc(-c4ccc5c(c4)CN(C(=O)CCC(F)(F)F)C5)ncc3F)ccc21] | 6-((5-fluoro-2-(2-(4,4,4-trifluoro-butanoyl)isoindolin-5-yl)pyrimidin-4-yl)amino)-3,4-dihydro-isoquinolin-1(2H)-one | (6-bromo-isoquinolin-1(2H)-one) in Step 3 was replaced with (6-bromo-3,4-dihydroisoquinolin-1(2H)-one); in Step 5-B was replaced with (4,4,4-trifluorobutanoic acid); and Step 5-A was omitted. | $^1$H NMR (400 MHz, DMSO-$d_6$) δ 9.91 (s, 1H), 8.56 (d, J = 2.0 Hz, 1H), 8.28-8.20 (m, 2H), 7.95-7.80 (m, 4H), 7.49 (d, J = 8.9 Hz, 1H), 4.96 (d, J = 9.4 Hz, 2H), 4.74 (d, J = 14.8 Hz, 2H), 3.41 (s, 4H), 2.96 (s, 2H), 2.71-2.66 (m, 2H). MS m/z (ESI): 500.1 [M + H]$^+$. |
| C67 | 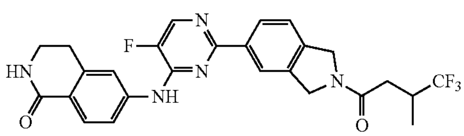 [SMILES: CC(CC(=O)N1Cc2ccc(-c3ncc(F)c(Nc4ccc5c(c4)CCNC5=O)n3)cc2C1)C(F)(F)F] | 6-((5-fluoro-2-(2-(4,4,4-trifluoro-3-methyl-butanoyl)isoindolin-5-yl)pyrimidin-4-yl)amino)-3,4-dihydro-isoquinolin-1(2H)-one | (6-bromo-isoquinolin-1(2H)-one) in Step 3 was replaced with (6-bromo-3,4-dihydroisoquinolin-1(2H)-one); and Step 5-A was omitted. | $^1$H NMR (400 MHz, DMSO-$d_6$) δ 9.91 (s, 1H), 8.56 (d, J = 2.1 Hz, 1H), 8.27-8.19 (m, 2H), 7.96-7.80 (m, 4H), 7.50 (dd, J = 11.2, 8.2 Hz, 1H), 4.96 (t, J = 8.6 Hz, 2H), 4.75 (d, J = 15.0 Hz, 2H), 3.46-3.39 (m, 4H), 2.98-2.93 (m, 4H), 2.76 (d, J = 16.4 Hz, 1H), 1.15 (d, J = 6.9 Hz, 3H). MS m/z (ESI): 514.1 [M + H]$^+$. |
| C70 | 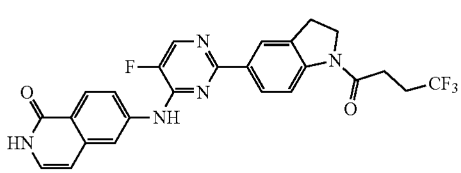 [SMILES: O=C(CCC(F)(F)F)N1CCc2cc(-c3ncc(F)c(Nc4ccc5c(=O)[nH]ccc5c4)n3)ccc21] | 6-((5-fluoro-2-(1-(4,4,4-trifluoro-butanoyl)indolin-5-yl)pyrimidin-4-yl)amino)isoquinolin-1(2H)-one | (5-bromo-indoline-N-Boc) in Step 1 was replaced with (6-bromo-indoline-N-Boc); in Step 5-B was replaced with (4,4,4-trifluorobutanoic acid); and Step 5-A was omitted. | $^1$H NMR (400 MHz, DMSO-$d_6$) δ 11.12 (d, J = 5.6 Hz, 1H), 9.99 (s, 1H), 8.54 (d, J = 3.5 Hz, 1H), 8.33 (d, J = 1.8 Hz, 1H), 8.22-8.13 (m, 4H), 7.90 (dd, J = 8.8, 2.0 Hz, 1H), 7.19 (dd, J = 7.0, 5.9 Hz, 1H), 6.51 (d, J = 7.0 Hz, 1H), 4.21 (t, J = 8.5 Hz, 2H), 3.25 (t, J = 8.4 Hz, 2H), 2.94-2.71 (m, 2H), 2.60 (t, J = 7.7 Hz, 2H). MS m/z (ESI): 497.6 [M + H]$^+$. |

| No. | Compound Structure | Compound Name | Starting material or regent from that in Example 4 | Characterization Data |
|---|---|---|---|---|
| C71 | (structure of 6-((5-fluoro-2-(1-(4,4,4-trifluoro-3-methylbutanoyl)indolin-5-yl)pyrimidin-4-yl)amino)isoquinolin-1(2H)-one) | 6-((5-fluoro-2-(1-(4,4,4-trifluoro-3-methyl-butanoyl)indolin-5-yl)pyrimidin-4-yl)amino)isoquinolin-1(2H)-one | (6-bromo-isoindoline-Boc) in Step 1 was replaced with (5-bromo-indoline-Boc); and Step 5-A was omitted. | $^1$H NMR (400 MHz, DMSO-$d_6$) δ 11.12 (d, J = 5.4 Hz, 1H), 9.99 (s, 1H), 8.54 (d, J = 3.6 Hz, 1H), 8.34 (d, J = 1.8 Hz, 1H), 8.22-8.13 (m, 4H), 7.90 (dd, J = 8.8, 2.0 Hz, 1H), 7.19 (dd, J = 7.0, 5.9 Hz, 1H), 6.51 (d, J = 7.0 Hz, 1H), 4.27-4.11 (m 2H), 3.25 (t, J = 8.4 Hz, 2H), 2.98 (d, J = 9.7 Hz, 1H), 2.89 (dd, J = 17.0, 3.3 Hz, 1H), 2.62 (dd, J = 16.8, 9.2 Hz, 1H), 1.18 (d, J = 6.9 Hz, 3H). MS m/z (ESI): 511.6 [M + H]$^+$. |
| C74 | (structure of 6-((5-fluoro-2-(1-(4,4,4-trifluoro-3-methylbutanoyl)indolin-5-yl)pyrimidin-4-yl)amino)-3,4-dihydroisoquinolin-1(2H)-one) | 6-((5-fluoro-2-(1-(4,4,4-trifluoro-3-methyl-butanoyl)indolin-5-yl)pyrimidin-4-yl)amino)-3,4-dihydro-isoquinolin-1(2H)-one | (6-bromo-isoindoline-Boc) in Step 1 was replaced with (5-bromo-indoline-Boc); (6-bromo-isoquinolin-1(2H)-one) in Step 3 was replaced with (6-bromo-3,4-dihydroisoquinolin-1(2H)-one); and Step 5-A was omitted. | $^1$H NMR (400 MHz, DMSO-$d_6$) δ 9.89 (s, 1H), 8.51 (d, J = 3.6 Hz, 1H), 8.20-8.12 (m, 3H), 7.99 (s, 1H), 7.88 (d, J = 8.5 Hz, 1H), 7.81 (d, J = 6.3 Hz, 2H), 4.21 (d, J = 9.1 Hz, 2H), 3.45-3.40 (m, 2H), 3.24 (t, J = 8.3 Hz, 2H), 2.96 (t, J = 6.5 Hz, 3H), 2.88 (d, J = 11.5 Hz, 1H), 2.61 (dd, J = 16.7, 9.3 Hz, 1H), 1.18 (d, J = 6.8 Hz, 3H). MS m/z (ESI): 513.6 [M + H]$^+$. |

| No. | Compound Structure | Compound Name | Starting material or regent from that in Example 4 | Characterization Data |
|---|---|---|---|---|
| C82 | 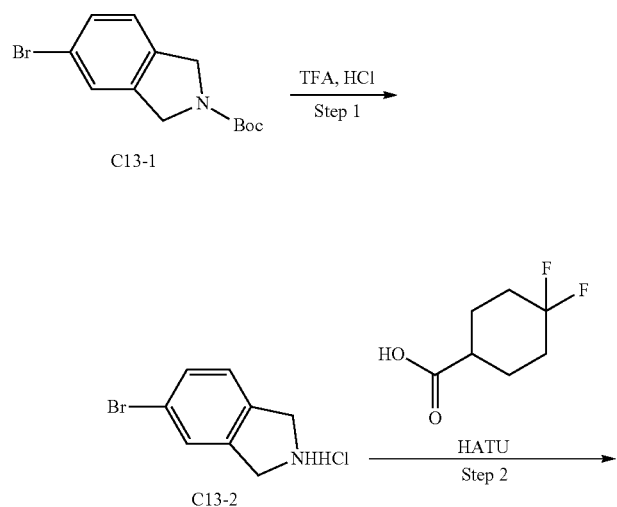 | 6-((5-fluoro-2-(2-(4,4,4-trifluoro-3,3-dimethyl-butanoyl)isoindolin-5-yl)pyrimidin-4-yl)amino)-3,4-dihydro-isoquinolin-1(2H)-one | in Step 3 was replaced with ; and Step 5-A was omitted. in Step 5-B was replaced with | $^1$H NMR (400 MHz, DMSO-$d_6$) δ 9.90 (s, 1H), 8.54 (s, 1H), 8.24-8.21 (m, 2H), 7.96-7.82 (m, 4H), 7.49 (t, J = 8.0 Hz, 1H), 4.94 (d, J = 10.0 Hz, 2H), 4.73 (d, J = 14.4 Hz, 2H), 3.43-3.41 (m, 2H), 2.97-2.93 (m, 2H), 2.60 (d, J = 3.6 Hz, 2H), 1.32 (s, 6H). MS m/z (ESI): 527.6 [M + H]$^+$. |

Example 5: Preparation of 6-((2-(2-(4,4-difluorocyclohexane-1-carbonyl)isoindolin-5-yl)-5-fluoropyrimidin-4-yl)amino)isoquinolin-1(2H)-one (C13)

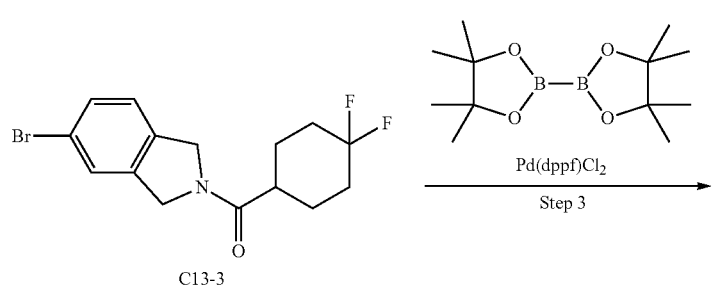

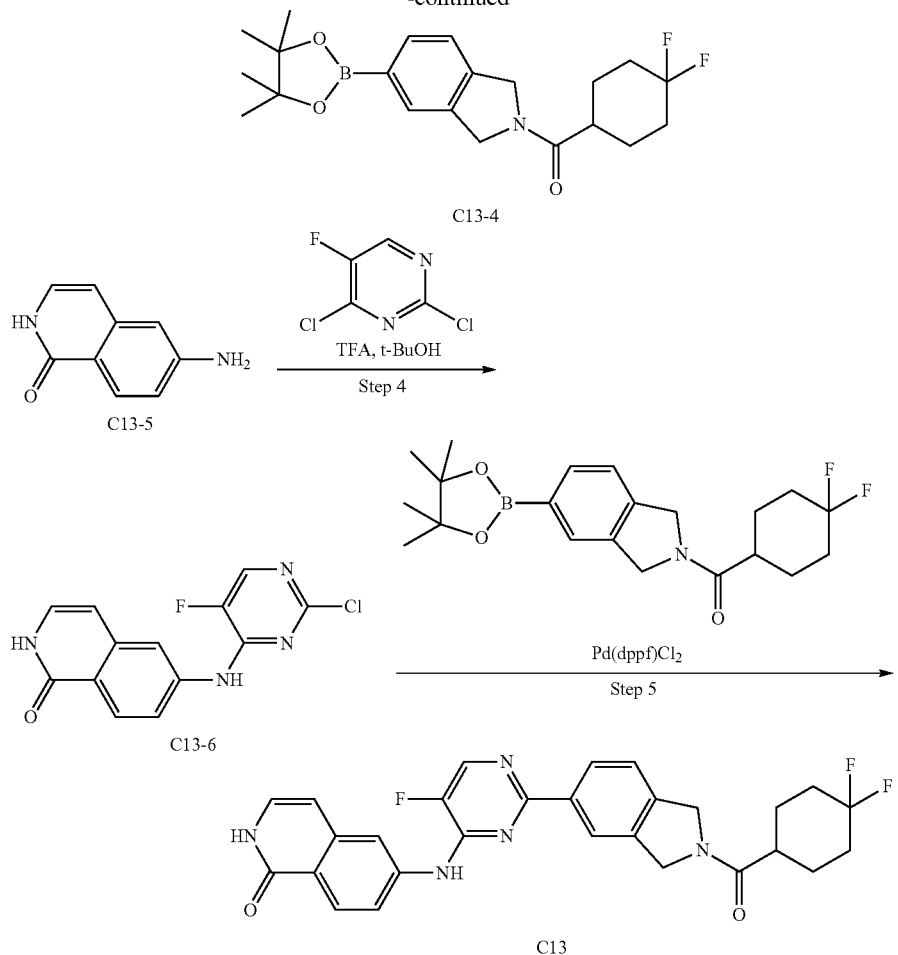

Step 1:

Compound C13-1 (20 g, 67 mmol) was dissolved in dichloromethane (20 mL), trifluoroacetic acid (50 mL) was added, and the reaction solution was stirred at room temperature for 16 hours. The reaction solvent and trifluoroacetic acid were removed by rotary evaporation in vacuum, the residue was added with water (20 mL) and concentrated hydrochloric acid (40 mL), and the precipitated solid was filtered and dried to afford compound C13-2 (15.3 g, grey solid, yield 97%).

$^1$H NMR (400 MHz, CDCl$_3$) δ 7.39 (s, 1H), 7.34 (d, J=8.2 Hz, 1H), 7.12 (d, J=8.0 Hz, 1H), 4.22 (d, J=14.1 Hz, 4H). MS m/z (ESI): 197.9, 199.8 [M-Cl]$^+$.

Step 2:

Compound C13-2 (932 mg, 4 mmol) and 4,4-difluorocyclohexane-1-carboxylic acid (656 mg, 4 mmol) were dissolved in N,N-dimethylformamide (30 mL), HATU (1.69 g, 4.4 mmol) and diisopropylethylamine (1.55 g, 12 mmol) were added, and the reaction was allowed to proceed at room temperature overnight. LC-MS indicated the reaction was complete. The reaction solution was concentrated under reduced pressure, the residue was dissolved in dichloromethane (20 mL), washed with water (20 mL×3), and then the organic phase was rotary evaporated to dryness. The residue was separated and purified by column chromatography on silica gel (petroleum ether:ethyl acetate=2:1) to afford compound C13-3 (1.1 g, white solid, yield 80%).

$^1$H NMR (400 MHz, CDCl$_3$) δ 7.43 (dd, J=15.6, 8.7 Hz, 2H), 7.16 (dd, J=21.7, 8.1 Hz, 1H), 4.80 (dd, J=33.8, 14.4 Hz, 4H), 2.54-2.49 (m, 1H), 2.34-2.17 (m, 1H), 2.03-1.71 (m, 3H). MS m/z (ESI): 343.8, 345.8 [M+H]$^+$.

Step 3:

Compound C13-3 (1.16 g, 3.37 mmol) and bis(pinacolato)diboron (941 mg, 3.7 mmol) were dissolved in 1,4-dioxane (35 mL), potassium acetate (980 mg, 10 mmol) was added, and purge with nitrogen was performed for 3 times. Pd(dppf)Cl$_2$ (732 mg, 1.0 mmol) was added, purge with nitrogen was performed for 3 times, and the reaction was placed in an oil bath at 90° C., and allowed to proceed overnight. LC-MS indicated the reaction was complete. The reaction solution was cooled to room temperature, concentrated under reduced pressure, and the residue was separated and purified by column chromatography on silica gel (petroleum ether:ethyl acetate=4:1) to afford compound C13-4 (1.3 g, white solid, yield 98.6%).

$^1$H NMR (400 MHz, DMSO-d$_6$) δ 7.67-7.59 (m, 2H), 7.36 (dd, J=12.2, 7.6 Hz, 1H), 4.94 (d, J=12.4 Hz, 2H), 4.65 (d, J=5.4 Hz, 2H), 2.71 (t, J=11.2 Hz, 1H), 2.08 (s, 2H), 1.90 (dd, J=21.2, 9.7 Hz, 4H), 1.64 (d, J=11.5 Hz, 2H), 1.30 (s, 12H). MS m/z (ESI): 391.8 [M+H]$^+$.

Step 4:

Compound C13-5 (500 mg, 3.12 mmol) and 2,4-dichloro-5-fluoropyrimidine (520 mg, 3.12 mmol) were added to tert-butanol (12 mL), trifluoroacetic acid (3.56 g, 31.2 mmol) was added, and the reaction was placed in an oil bath at 100° C., and allowed to proceed for 24 hours. The reaction solution was cooled to room temperature, concentrated under reduced pressure, and the residue was purified by combi-flash chromatography (petroleum ether:ethyl acetate=4:1) to afford compound C13-6 (420 mg, yellow solid, yield 46%). MS m/z (ESI): 290.8 [M+H]$^+$.

Step 5:

Compound C13-4 (129 mg, 0.33 mmol) and C13-6 (96 mg, 0.33 mmol) were dissolved in a mixed solution of 1,4-dioxane/water (10:1) (16.5 mL), potassium carbonate (138 mg, 0.99 mmol) was added, and purge with nitrogen was performed for 3 times. Pd(dppf)Cl$_2$ (74 mg, 0.099 mmol) was added, purge with nitrogen was performed for 3 times, and the reaction was placed in an oil bath at 110° C., and allowed to proceed overnight. LC-MS indicated the reaction was complete. The reaction solution was cooled to room temperature, concentrated under reduced pressure, and the residue was purified by preparative thin-layer chromatography and high performance liquid chromatography to afford compound C13 (11.3 mg, light yellow solid, yield 7%).

$^1$H NMR (400 MHz, DMSO-d$_6$) δ 11.14 (s, 1H), 10.05 (s, 1H), 8.58 (s, 1H), 8.33-8.14 (m, 4H), 7.97 (dd, J=40.4, 8.9 Hz, 1H), 7.50 (t, J=8.7 Hz, 1H), 7.19 (dd, J=12.5, 6.2 Hz, 1H), 6.51 (d, J=6.0 Hz, 1H), 5.02 (d, J=9.5 Hz, 2H), 4.72 (d, J=15.9 Hz, 2H), 2.74 (s, 1H), 2.09 (s, 2H), 2.01-1.85 (m, 4H), 1.70-1.60 (m, 2H). MS m/z (ESI): 519.5 [M+H]$^+$.

The compounds in the following Table were prepared according to methods similar to that described in Example 5.

| No. | Compound Structure | Compound Name | Starting material or regent different from that in Example 5 | Characterization Data |
|---|---|---|---|---|
| C50 | 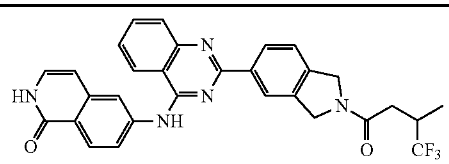 | 6-((2-(2-(4,4,4-trifluoro-3-methylbutanoyl))isoindolin-5-yl)quinazolin-4-yl)amino)isoquinolin-1(2H)-one | in Step 2 was replaced with<br><br>Step 3 was performed with the product of this step, and the product obtained in Step 3 was employed in Step 5;<br><br>in Step 4 was replaced with | $^1$H NMR (400 MHz, DMSO-d$_6$) δ 11.19 (s, 1H), 10.44 (d, J = 16.6 Hz, 1H), 8.68 (d, J = 8.3 Hz, 1H), 8.52-8.33 (m, 3H), 8.29 (d, J = 8.4 Hz, 1H), 8.08 (dd, J = 23.9, 7.6 Hz, 1H), 7.97 (s, 2H), 7.73 (s, 1H), 7.59-7.51 (m, 1H), 7.22 (dd, J = 13.3, 7.1 Hz, 1H), 6.58 (d, J = 7.1 Hz, 1H), 5.04-4.93 (m, 2H), 4.78 (d, J = 17.0 Hz, 2H), 2.98-2.89 (m, 1H), 2.77 (d, J = 16.3 Hz, 1H), 2.60-2.53 (m, 1H), 1.16 (d, J = 6.8 Hz, 3H). MS m/z (ESI): 544.1 [M + H]$^+$. |
| C33 | 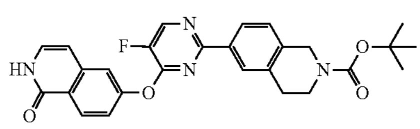 [SMILES: CC(C)(C)OC(=O)N1CCc2cc(-c3ncc(F)c(Oc4ccc5c(=O)[nH]ccc5c4)n3)ccc2C1] | tert-butyl 6-(5-fluoro-4-((1-oxo-1,2-dihydroisoquinolin-6-yl)oxy)pyrimidin-2-yl)-3,4-dihydroisoquinoline-2(1H)-carboxylate | Step 1 and Step 2 were omitted, starting from Step 3, C13-3 was replaced with<br><br>C13-5 in Step 4 was replaced with<br><br>TFA was replaced with TEA, t-BuOH was replaced with EtOH. | $^1$H NMR (400 MHz, CDCl$_3$) δ 11.37 (d, J = 6.2 Hz, 1H), 8.94 (d, J = 2.7 Hz, 1H), 8.31 (d, J = 8.8 Hz, 1H), 7.88 (s, 1H), 7.79 (d, J = 8.1 Hz, 1H), 7.68 (d, J = 2.3 Hz, 1H), 7.52 (dd, J = 8.8 Hz, J = 2.4 Hz, 1H), 7.24 (s, 2H), 6.58 (d, J = 6.9 Hz, 1H), 4.50 (s, 2H), 3.54 (s, 2H), 2.77 (s, 2H), 1.42 (s, 9H). MS m/z (ESI): 488.7 [M + H]$^+$. |

Example 6: Preparation of 3,3-difluorocyclobutyl 2-(5-fluoro-4-((1-oxo-1,2-dihydroisoquinolin-6-yl)amino)pyrimidin-2-yl)-6,7-dihydrothieno[3,2-c]pyridine-5(4H)-carboxylate (C27) and 6-((5-fluoro-2-(5-(4,4,4-trifluoro-3-methylbutanoyl)-4,5,6,7-tetrahydrothieno[3,2-c]pyridin-2-yl)pyrimidin-4-yl)amino)isoquinolin-1(2H)-one (C47)
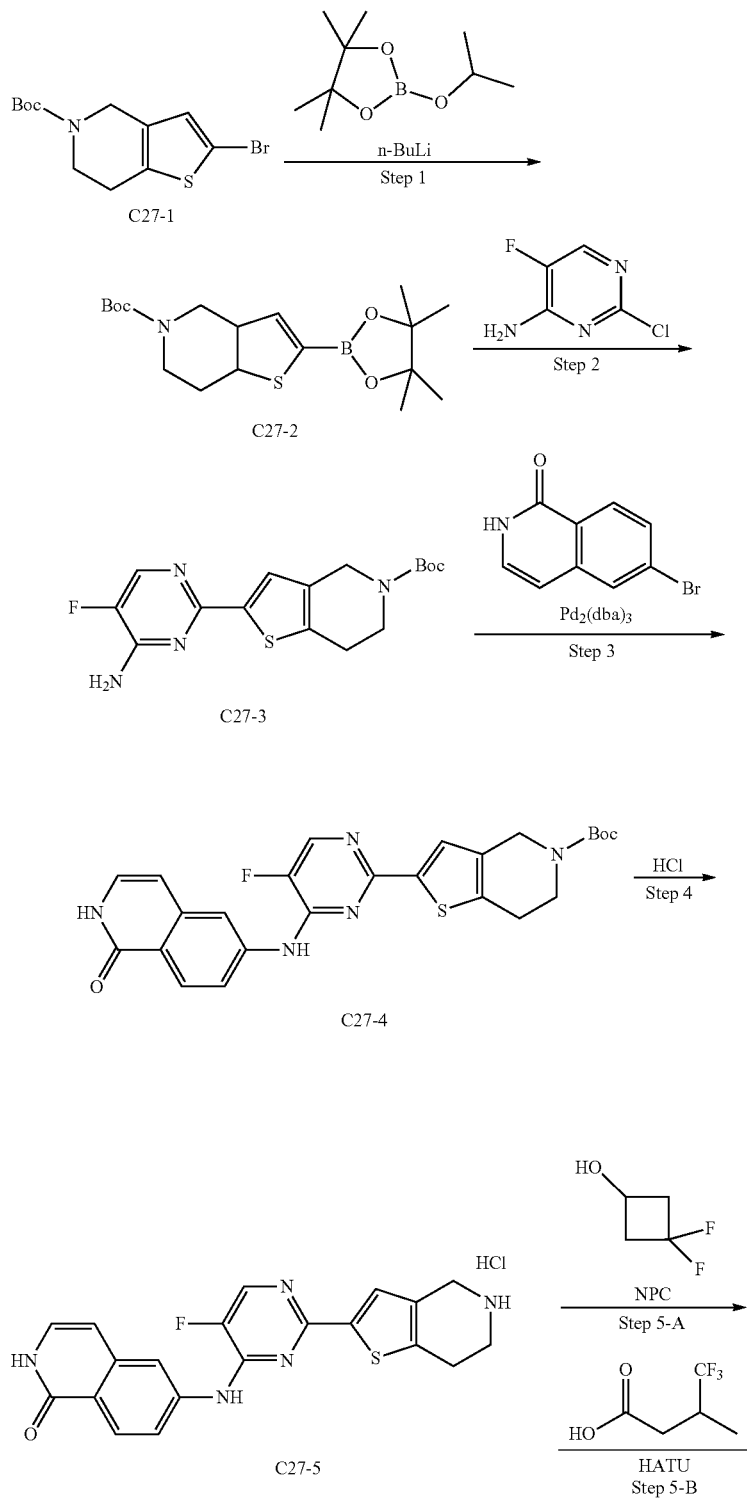

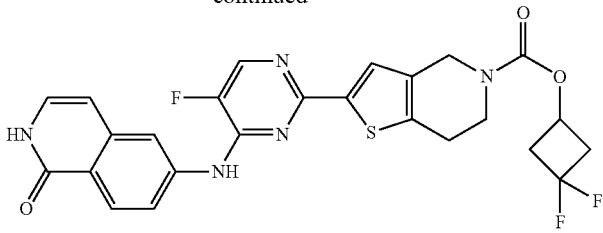

C27

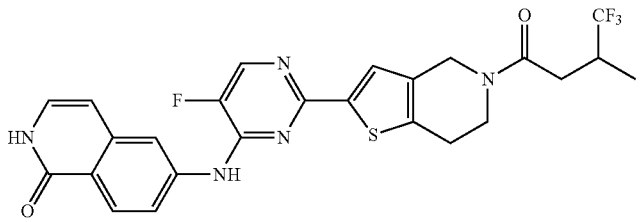

C47

Step 1:

Compound C27-1 (400 mg, 1.257 mmol) was dissolved in anhydrous tetrahydrofuran (10 mL), purge with nitrogen was performed for three times, the reaction solution was cooled to −78° C., n-butyllithium (1.3 M in hexane, 1.2 mL) was added, and the reaction was further stirred at −78° C. for 2 hours. Isopropoxyboronic acid pinacol ester (257 mg, 1.383 mmol) was added, the reaction was slowly warmed to room temperature, and stirred for 16 hours. LC-MS indicated the reaction was complete. The reaction was quenched by adding water (3 mL), and the reaction solvent was removed by rotary evaporation in vacuum, to afford compound C27-2 (450 mg, yellow solid, yield 96%). MS m/z (ESI): 387.8 [M+Na]$^+$.

Step 2:

n-butanol (10 mL) and Pd(dppf)Cl$_2$ (450 mg, 0.616 mmol) were added to a mixture of compound C27-2 (450 mg, 1.232 mmol), 2-chloro-5-fluoropyrimidin-4-amine (182 mg, 1.232 mmol) and potassium phosphate (784 mg, 3.700 mmol), purge with nitrogen was performed for three times, and then the reaction was placed in a microwave reactor at 110° C. and stirred for 30 minutes. LC-MS indicated the reaction was complete. The reaction solution was cooled to room temperature, and the reaction solvent was removed by rotary evaporation in vacuum. The residue was purified by flash column chromatography (EA/PE, 0~30%), to afford compound C27-3 (140 mg, white solid, yield 32%).

$^1$H NMR (400 MHz, DMSO-d$_6$) δ 7.20 (s, 1H), 6.70 (s, 1H), 3.69 (s, 2H), 2.94 (s, 2H), 2.05 (s, 2H), 0.71 (s, 9H). MS m/z (ESI): 350.7 [M+H]$^+$.

Step 3:

1,4-dioxane (15 mL) and Pd$_2$(dba)$_3$ (62 mg, 0.68 mmol) were added to a mixture of compound C27-3 (140 mg, 0.400 mmol), 6-bromoisoquinolin-1(2H)-one (107 mg, 0.479 mmol), cesium carbonate (390 mg, 1.199 mmol) and Xantphos (1.18 g, 2.03 mmol), purge with nitrogen was performed for three times, and the reaction solution was stirred at 110° C. for 16 hours. LC-MS indicated the reaction was complete. The reaction solution was cooled to room temperature, filtered to remove the insoluble materials, and the resulting filtrate was rotary evaporated in vacuum to remove the reaction solvent. The residue was purified by flash column chromatography (MeOH/DCM, 0~5%), to afford compound C27-4 (64 mg, yellow solid, yield 32%).

$^1$H NMR (400 MHz, DMSO-d$_6$) δ 11.13 (s, 1H), 10.01 (s, 1H), 8.47 (d, J=3.4 Hz, 1H), 8.30 (s, 1H), 8.18 (d, J=8.9 Hz, 1H), 7.93 (d, J=8.4 Hz, 1H), 7.61 (s, 1H), 7.18 (t, J=6.2 Hz, 1H), 6.52 (d, J=7.0 Hz, 1H), 4.48 (s, 2H), 3.66 (t, J=5.4 Hz, 2H), 2.85 (s, 2H), 1.45 (s, 9H). MS m/z (ESI): 493.6 [M+H]$^+$.

Step 4:

Compound C27-4 (64 mg, 0.142 mmol) was dissolved in dichloromethane (10 mL), a solution of hydrochloric acid/1,4-dioxane (4 M, 5 mL) was added, and the reaction solution was stirred at room temperature for 16 hours. LC-MS indicated the reaction was complete. The reaction was concentrated under reduced pressure to remove the solvent, to afford a crude product of compound C27-5 (80 mg, yellow solid). MS m/z (ESI): 393.7 [M-Cl]$^+$.

Step 5-A:

3,3-difluorocyclobutanol (18 mg, 0.168 mmol) and bis(4-nitrophenyl)carbonate (47 mg, 0.153 mmol) were dissolved in N,N-dimethylformamide (10 mL), triethylamine (93 mg, 0.915 mmol) was added, and the reaction solution was stirred at 45° C. for 2 hours. Compound C27-5 (60 mg, 0.153 mmol) was added, and the reaction solution was stirred at 45° C. for 16 h. LC-MS indicated the reaction was complete. The reaction solution was cooled to room temperature, the solvent was removed by rotary evaporation. The residue was separated and purified by preparative chromatography (ACN/H$_2$O (0.1% FA), 45~60%), to afford compound C27 (16.9 mg, white solid, yield 21%).

$^1$H NMR (400 MHz, DMSO-d$_6$) δ 11.13 (d, J=5.8 Hz, 1H), 10.01 (s, 1H), 8.47 (d, J=3.4 Hz, 1H), 8.28 (s, 1H), 8.18 (d, J=8.8 Hz, 1H), 7.93 (d, J=7.6 Hz, 1H), 7.62 (s, 1H), 7.18 (t, J=6.4 Hz, 1H), 6.52 (d, J=7.2 Hz, 1H), 4.88 (s, 1H), 4.55 (d, J=23.1 Hz, 2H), 3.72 (s, 2H), 3.10-3.00 (m, 2H), 2.89 (s, 2H), 2.77 (td, J=14.4, 4.8 Hz, 2H). MS m/z (ESI): 527.8 [M+H]$^+$.

Step 5-B:

C27-5 (60 mg, 0.153 mmol) and HATU (55 mg, 0.168 mmol) were dissolved in N,N-dimethylformamide (5 mL), 4,4,4-trifluoro-3-methylbutanoic acid (24 mg, 0.153 mmol) and diisopropylethylamine (99 mg, 0.763 mmol) were added, and the reaction solution was stirred at room temperature for 16 hours. LC-MS indicated the reaction was complete. The reaction solution was cooled to room temperature, and the reaction solvent was removed by rotary evaporation in vacuum. The residue was separated and purified by preparative chromatography (ACN/H$_2$O (0.1% TFA), 40~70%), to afford compound C47 (18.83 mg, white solid, yield 23%).

$^1$H NMR (400 MHz, DMSO-d$_6$) δ 11.13 (s, 1H), 10.01 (s, 1H), 8.47 (d, J=3.6 Hz, 1H), 8.30 (d, J=14.9 Hz, 1H), 8.18 (d, J=8.9 Hz, 1H), 7.93 (t, J=9.7 Hz, 1H), 7.63 (d, J=11.2 Hz, 1H), 7.21-7.17 (m, 1H), 6.53 (d, J=6.4 Hz, 1H), 4.67-4.61 (m, 2H), 3.81 (d, J=23.9 Hz, 3H), 2.96 (s, 2H), 2.85 (s, 2H), 1.11 (dd, J=6.8, 3.6 Hz, 3H). MS m/z (ESI): 531.6 [M+H]$^+$.

The compounds in the following Table were prepared according to methods similar to that described in Example 6.

| No. | Compound Structure | Compound Name | Starting material or regent different from that in Example 6 | Characterization Data |
|---|---|---|---|---|
| C28 | 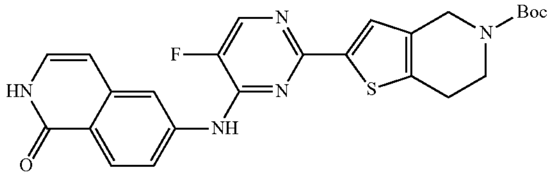 [SMILES: CC(C)(C)OC(=O)N1CCc2sc(-c3ncc(F)c(Nc4ccc5c(=O)[nH]ccc5c4)n3)cc2C1] | tert-butyl 2-(5-fluoro-4-((1-oxo-1,2-dihydroisoquinolin-6-yl)amino)pyrimidin-2-yl)-6,7-dihydrothieno[3,2-c]pyridine-5(4H)-carboxylate | i.e., Intermediate C27-4. | $^1$H NMR (400 MHz, DMSO-d$_6$) δ 11.13 (s, 1H), 10.01 (s, 1H), 8.47 (d, J = 3.4 Hz, 1H), 8.30 (s, 1H), 8.18 (d, J = 8.9 Hz, 1H), 7.93 (d, J = 8.4 Hz, 1H), 7.61 (s, 1H), 7.18 (t, J = 6.2 Hz, 1H), 6.52 (d, J = 7.0 Hz, 1H), 4.48 (s, 2H), 3.66 (t, J = 5.4 Hz, 2H), 2.85 (s, 2H), 1.45 (s, 9H). MS m/z (ESI): 493.6 [M + H]$^+$. |
| C42 | 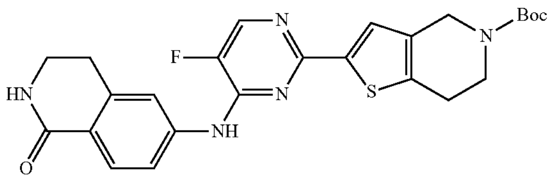 [SMILES: CC(C)(C)OC(=O)N1CCc2sc(-c3ncc(F)c(Nc4ccc5c(c4)CCNC5=O)n3)cc2C1] | tert-butyl 2-(5-fluoro-4-((1-oxo-1,2,3,4-tetrahydroisoquinolin-6-yl)amino)pyrimidin-2-yl)-6,7-dihydrothieno[3,2-c]pyridine-5(4H)-carboxylate | ![Br-isoquinolinone] replaced with ![Br-tetrahydroisoquinolinone] in Step 3 was replaced and the syntheses in Step 4, Step 5-A and Step 5-B were omitted. | $^1$H NMR (400 MHz, DMSO-d$_6$) δ 9.88 (s, 1H), 8.43 (d, J = 3.5 Hz, 1H), 7.89 (d, J = 14.9 Hz, 3H), 7.81 (s, 1H), 7.58 (s, 1H), 4.47 (s, 2H), 3.65 (s, 2H), 3.41 (s, 2H), 2.95 (t, J = 6.3 Hz, 2H), 2.83 (s, 2H), 1.44 (s, 9H). MS m/z (ESI): 495.8 [M + H]$^+$. |
| C43 | 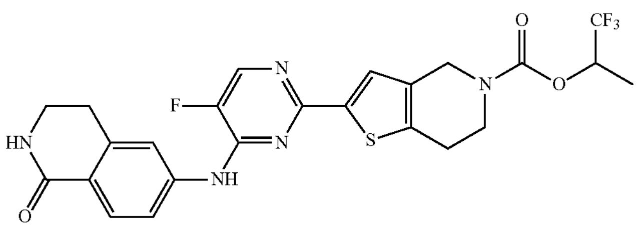 [SMILES: CC(OC(=O)N1CCc2sc(-c3ncc(F)c(Nc4ccc5c(c4)CCNC5=O)n3)cc2C1)C(F)(F)F] | 1,1,1-trifluoropropan-2-yl 2-(5-fluoro-4-((1-oxo-1,2,3,4-tetrahydroisoquinolin-6-yl)amino)pyrimidin-2-yl)-6,7-dihydrothieno[3,2-c]pyridine-5(4H)-carboxylate | ![Br-isoquinolinone] replaced with ![Br-tetrahydroisoquinolinone] in Step 3 was replaced | $^1$H NMR (400 MHz, DMSO-d$_6$) δ 9.88 (s, 1H), 8.44 (d, J = 3.6 Hz, 1H), 7.87 (s, 3H), 7.80 (s, 1H), 7.63 (s, 1H), 5.40 (s, 1H), 4.56 (s, 2H), 3.74 (s, 2H), 3.41-3.37 (m, 2H), 2.96 (d, J = 6.2 Hz, 2H), 2.90 (s, 2H), 1.40 (d, J = 6.5 Hz, 3H). MS m/z (ESI): 535.5 [M + H]$^+$. |

| No. | Compound Structure | Compound Name | Starting material or regent different from that in Example 6 | Characterization Data |
|---|---|---|---|---|
| C45 | 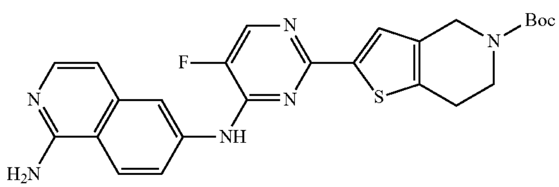 [SMILES: CC(C)(C)OC(=O)N1CCc2sc(-c3ncc(F)c(Nc4ccc5c(N)nccc5c4)n3)cc2C1] | tert-butyl 2-(4-((1-aminoisoquinolin-6-yl)amino)-5-fluoropyrimidin-2-yl)-6,7-dihydrothieno[3,2-c]pyridine-5(4H)-carboxylate | HO— (cyclobutane with 2F) and in Step 5-A was replaced with OH—CF$_3$ in Step 5-A; and Step 5-B was omitted. | $^1$H NMR (400 MHz, DMSO-d$_6$) δ 12.84 (s, 1H), 10.35 (s, 1H), 8.88 (s, 1H), 8.55 (t, J = 6.2 Hz, 1H), 8.22 (d, J = 9.2 Hz, 1H), 7.66 (dd, J = 14.8, 7.8 Hz, 2H), 7.11 (dd, J = 57.6, 29.0 Hz, 1H), 4.48 (s, 2H), 3.67 (t, J = 5.6 Hz, 2H), 2.86 (s, 2H), 1.45 (s, 9H). MS m/z (ESI): 492.6 [M + H]$^+$. Br-isoquinolinone in Step 3 was replaced with Br-aminoisoquinoline; and Step 4, Step 5-A and Step 5-B were omitted. |
| C46 | 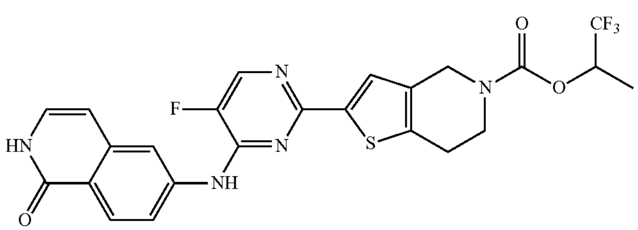 [SMILES: CC(OC(=O)N1CCc2sc(-c3ncc(F)c(Nc4ccc5c(=O)[nH]ccc5c4)n3)cc2C1)C(F)(F)F] | 1,1,1-trifluoropropan-2-yl 2-(5-fluoro-4-((1-oxo-1,2-dihydroisoquinolin-6-yl)amino)pyrimidin-2-yl)-6,7-dihydrothieno[3,2-c]pyridine-5(4H)-carboxylate | HO— (cyclobutane with 2F) in Step 5-A was replaced with OH—CF$_3$; and Step 5-B was omitted. | $^1$H NMR (400 MHz, DMSO-d$_6$) δ 11.13 (d, J = 4.7 Hz, 1H), 10.01 (s, 1H), 8.47 (d, J = 3.4 Hz, 1H), 8.28 (d, J = 14.6 Hz, 1H), 8.17 (d, J = 8.7 Hz, 1H), 7.92 (d, J = 8.5 Hz, 1H), 7.64 (s, 1H), 7.18 (m, 1H), 6.52 (d, J = 6.6 Hz, 1H), 5.39 (m, 1H), 4.56 (s, 2H), 3.74 (s, 2H), 2.90 (s, 2H), 1.39 (d, J = 6.5 Hz, 3H). MS m/z (ESI): 534.0 [M + H]$^+$. |

| No. | Compound Structure | Compound Name | Starting material or regent different from that in Example 6 | Characterization Data |
|---|---|---|---|---|
| C59 | 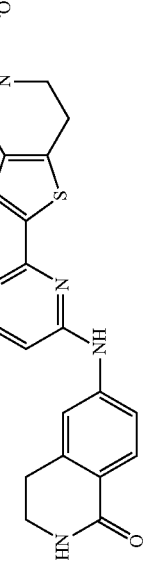 | 1,1,1-trifluoropropan-2-yl 2-(4-((1-oxo-1,2,3,4-tetrahydroisoquinolin-6-yl)amino)pyrimidin-2-yl)-6,7-dihydrothieno[3,2-c]pyridine-5(4H)-carboxylate | 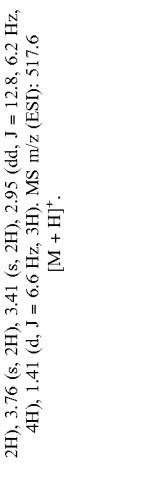 in Step 2 was replaced with 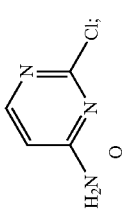; <br><br>in Step 3 was replaced with <br><br>in Step 5-A was replaced with <br><br>; and Step 5-B was omitted. | $^1$H NMR (400 MHz, DMSO-$d_6$) δ 10.08 (s, 1H), 8.34 (d, J = 6.0 Hz, 1H), 7.86 (d, J = 8.4 Hz, 1H), 7.84-7.69 (m, 4H), 6.72 (d, J = 6.2 Hz, 1H), 5.45-5.36 (m, 1H), 4.58 (s, 2H), 3.76 (s, 2H), 3.41 (s, 2H), 2.95 (dd, J = 12.8, 6.2 Hz, 4H), 1.41 (d, J = 6.6 Hz, 3H). MS m/z (ESI): 517.6 [M + H]$^+$. |

| No. | Compound Structure | Compound Name | Starting material or regent different from that in Example 6 | Characterization Data |
|---|---|---|---|---|
| C60 | 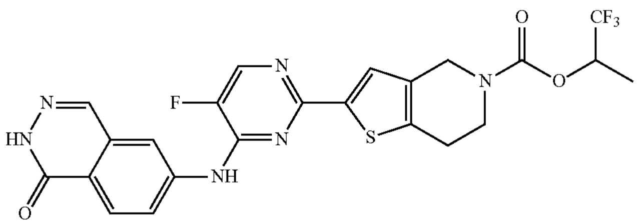 | 1,1,1-trifluoropropan-2-yl 2-(5-fluoro-4-((1-oxo-1,2-dihydrophthalazin-6-yl)amino)pyrimidin-2-yl)-6,7-dihydrothieno[3,2-c]pyridine-5(4H)-carboxylate | ![Br-phthalazinone] in Step 3 was replaced with ![Br-phthalazinone variant] | $^1$H NMR (400 MHz, DMSO-d$_6$) δ 12.55 (s, 1H), 10.26 (s, 1H), 8.52 (d, J = 3.6 Hz, 1H), 8.39 (s, 1H), 8.24 (s, 2H), 7.69 (s, 1H), 7.22-6.95 (m, 1H), 5.40 (s, 1H), 4.59 (s, 2H), 3.75 (s, 2H), 2.92 (s, 2H), 1.40 (d, J = 6.6 Hz, 3H), MS m/z (ESI): 534.6 [M + H]$^+$. |
| C61 | 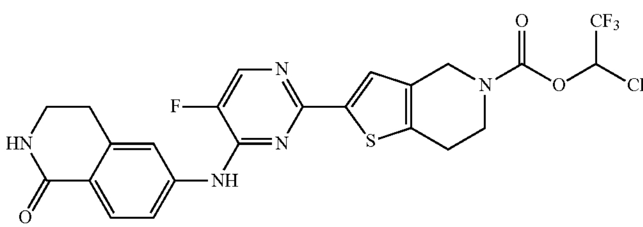 | 1,1,1,3,3,3-hexafluoropropan-2-yl 2-(5-fluoro-4-((1-oxo-1,2,3,4-tetrahydroisoquinolin-6-yl)amino)pyrimidin-2-yl)-6,7-dihydrothieno[3,2-c]pyridine-5(4H)-carboxylate | ![Br-isoquinolinone] in Step 3 was replaced with ![Br-tetrahydroisoquinolinone]; ![HO-cyclobutane-CF3] in Step 5-A was replaced with ![HO-CF3]; and Step 5-B was omitted. | $^1$H NMR (400 MHz, DMSO-d$_6$) δ 9.88 (s, 1H), 8.44 (d, J = 3.3 Hz, 1H), 7.87 (s, 3H), 7.80 (s, 1H), 7.64 (d, J = 7.9 Hz, 1H), 6.67 (d, J = 4.4 Hz, 1H), 4.63 (s, 2H), 3.80 (s, 2H), 3.41 (s, 2H), 2.94 (s, 4H). MS m/z (ESI): 589.6 [M + H]$^+$. |

| No. | Compound Structure | Compound Name | Starting material or regent different from that in Example 6 | Characterization Data |
|---|---|---|---|---|
| C65 | (structure shown) | (R)-1,1,1-trifluoropropan-2-yl 2-(5-fluoro-4-((1-oxo-1,2,3,4-tetrahydroisoquinolin-6-yl)amino)pyrimidin-2-yl)-6,7-dihydrothieno[3,2-c]pyridine-5(4H)-carboxylate | 5-A was replaced with HO—⟨cyclobutyl⟩—F,F in Step; F₃C—CH(OH)—CF₃; and Step 5-B was omitted. Br-isoquinolinone in Step 3 was replaced with Br-isoquinolinone; HO—⟨cyclobutyl⟩—F,F in Step; (R)-F₃C—CH(OH)—; and Step 5-B was omitted. | ¹H NMR (400 MHz, DMSO-d₆) δ 9.88 (s, 1H), 8.44 (d, J = 3.6 Hz, 1H), 7.84 (d, J = 28.2 Hz, 3H), 7.63 (s, 1H), 7.02 (d, J = 51.5 Hz, 1H), 5.40 (s, 1H), 4.56 (s, 2H), 3.74 (s, 2H), 2.95 (s, 4H), 2.08 (s, 2H), 1.40 (d, J = 6.8 Hz, 3H). MS m/z (ESI): 535.6 [M + H]⁺. |

| No. | Compound Structure | Compound Name | Starting material or regent different from that in Example 6 | Characterization Data |
|---|---|---|---|---|
| C75 | (structure shown) | 2,2,2-trifluoroethyl 2-(5-fluoro-4-((1-oxo-1,2,3,4-tetrahydroisoquinolin-6-yl)amino)pyrimidin-2-yl)-6,7-dihydrothieno[3,2-c]pyridine-5(4H)-carboxylate | (6-bromoisoquinolin-1(2H)-one structure) in Step 3 was replaced with (6-bromo-3,4-dihydroisoquinolin-1(2H)-one structure); HOCH₂CF₃; and Step 5-B was omitted. | ¹H NMR (400 MHz, DMSO-d₆) δ 9.89-9.88 (m, 1H), 8.44 (d, J = 3.7 Hz, 1H), 7.84 (d, J = 26.8 Hz, 3H), 7.63 (s, 1H), 7.23-6.94 (m, 1H), 4.77 (d, J = 9.1 Hz, 2H), 4.58 (d, J = 9.2 Hz, 2H), 3.76-3.74 (m, 2H), 3.41 (s, 2H), 2.95 (s, 2H), 2.90 (s, 2H). MS m/z (ESI): 521.5 [M + H]⁺. |
| C49 | (structure shown) | 6-((2-(5-(4,4,4-trifluoro-3-methylbutanoyl)-4,5,6,7-tetrahydrothieno[3,2-c]pyridin-2-yl)pyrimidin-4-yl)amino)isoquinolin-1(2H)-one | (3-fluoro-4-amino-2-chloropyrimidine structure) in Step 2 was replaced with (4-amino-2-chloropyrimidine structure); and Step 5-A was omitted. | ¹H NMR (400 MHz, DMSO-d₆) δ 11.08 (d, J = 5.5 Hz, 1H), 10.15 (s, 1H), 8.37 (dd, J = 5.9, 2.3 Hz, 1H), 8.26 (d, J = 8.5 Hz, 1H), 8.17 (d, J = 8.8 Hz, 1H), 7.72 (dd, J = 13.6, 9.5 Hz, 2H), 7.21-7.15 (m, 1H), 6.76 (d, J = 5.9 Hz, 1H), 6.53 (d, J = 7.0 Hz, 1H), 4.71-4.61 (m, 2H), 3.84 (d, J = 5.6 Hz, 2H), 3.81 (s, 1H), 2.98 (s, 1H), 2.87 (s, 1H), 2.77 (d, J = 15.6 Hz, 1H), 2.59 (dd, J = 9.7, 6.6 Hz, 1H), 1.12 (dd, J = 6.8, 2.7 Hz, 3H). MS m/z (ESI): 514.0 [M + H]⁺. |

| No. | Compound Structure | Compound Name | Starting material or regent different from that in Example 6 | Characterization Data |
|---|---|---|---|---|
| C52 | 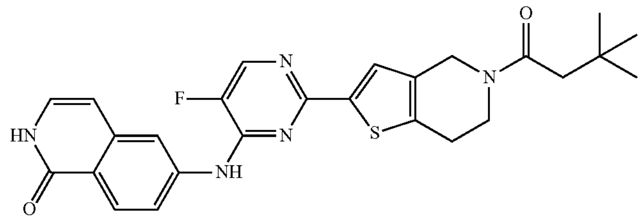 [SMILES: CC(C)(C)CC(=O)N1CCc2sc(-c3ncc(F)c(Nc4ccc5c(=O)[nH]ccc5c4)n3)cc2C1] | 6-((2-(5-(3,3-dimethylbutanoyl)-4,5,6,7-tetrahydrothieno[3,2-c]pyridin-2-yl)-5-fluoropyrimidin-4-yl)amino)isoquinolin-1(2H)-one | ![structure] CF₃ in Step 5-B was replaced with [structure]; and Step 5-A was omitted. | ¹H NMR (400 MHz, DMSO-d₆) δ 11.13 (s, 1H), 10.01 (s, 1H), 8.47 (d, J = 2.6 Hz, 1H), 8.34-8.24 (m, 1H), 8.20-8.15 (m, 1H), 7.97-7.88 (m, 1H), 7.62 (d, J = 5.9 Hz, 1H), 7.19 (s, 1H), 6.52 (s, 1H), 4.64 (d, J = 29.1 Hz, 2H), 3.82 (t, J = 5.6 Hz, 2H), 2.92 (s, 2H), 2.35 (d, J = 11.2 Hz, 2H), 1.01 (d, J = 17.6 Hz, 9H). MS m/z (ESI): 491.6 [M + H]⁺. |
| C53 | 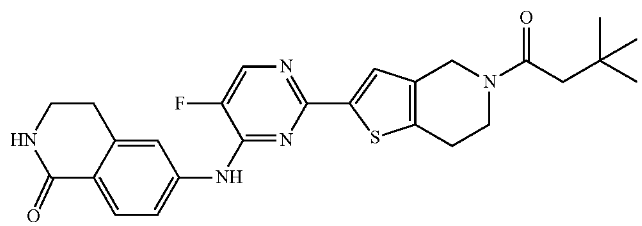 [SMILES: CC(C)(C)CC(=O)N1CCc2sc(-c3ncc(F)c(Nc4ccc5c(c4)CCNC5=O)n3)cc2C1] | 6-((2-(5-(3,3-dimethylbutanoyl)-4,5,6,7-tetrahydrothieno[3,2-c]pyridin-2-yl)-5-fluoropyrimidin-4-yl)amino)-3,4-dihydroisoquinolin-1(2H)-one | [Br-isoquinolinone] in Step 3 was replaced with [Br-dihydroisoquinolinone] and HO-CF₃ in Step 5-B was replaced with [structure]; and Step 5-A was omitted. | ¹H NMR (400 MHz, DMSO-d₆) δ 9.86 (s, 1H), 8.42 (d, J = 3.0 Hz, 1H), 7.90 (dd, J = 17.9, 8.9 Hz, 2H), 7.85 (s, 1H), 7.79 (s, 1H), 7.58 (d, J = 3.8 Hz, 1H), 4.65 (s, 1H), 4.58 (s, 1H), 3.80 (t, J = 5.2 Hz, 2H), 3.41 (s, 2H), 2.94 (s, 2H), 2.89 (s, 1H), 2.79 (d, J = 10.6 Hz, 2H), 2.33 (d, J = 17.2 Hz, 9H). MS m/z (ESI): 494.1 [M + H]⁺. |

| No. | Compound Structure | Compound Name | Starting material or regent different from that in Example 6 | Characterization Data |
|---|---|---|---|---|
| C55 | (structure) | 6-((5-fluoro-2-(5-(4,4,4-trifluoro-3-methylbutanoyl)-4,5,6,7-tetrahydrothieno[3,2-c]pyridin-2-yl)pyridin-4-yl)amino)-3,4-dihydroisoquinolin-1(2H)-one | (structure) in Step 3 was replaced with (structure); and Step 5-A was omitted. | ¹H NMR (400 MHz, DMSO-d₆) δ 9.87 (s, 1H), 8.43 (s, 1H), 7.88 (m, 3H), 7.79 (s, 1H), 7.59 (d, J = 10.5 Hz, 1H), 4.62 (m, 2H), 3.80 (d, J = 16.8 Hz, 3H), 3.41 (s, 2H), 2.94 (d, J = 5.6 Hz, 3H), 2.83 (s, 1H), 2.57 (m, 2H), 1.10 (m, 3H). MS m/z (ESI): 534.1 [M + H]⁺. |
| C57 | (structure) | 6-((2-(5-(3,3-dimethylbutanoyl)-4,5,6,7-tetrahydrothieno[3,2-c]pyridin-2-yl)pyrimidin-4-yl)amino)isoquinolin-1(2H)-one | (structure) in Step 2 was replaced with (structure); (structure) in Step 5-B was replaced with (structure); and Step 5-A was omitted. | ¹H NMR (400 MHz, DMSO-d₆) δ 11.10 (s, 1H), 10.20 (s, 1H), 8.37 (d, J = 5.9 Hz, 1H), 8.25 (d, J = 24.3 Hz, 1H), 8.17 (d, J = 8.7 Hz, 1H), 7.72 (dd, J = 20.7, 8.2 Hz, 2H), 7.18 (t, J = 6.4 Hz, 1H), 6.76 (d, J = 4.2 Hz, 1H), 6.55-6.51 (m, 1H), 4.69 (s, 1H), 4.62 (s, 1H), 3.83 (t, J = 5.5 Hz, 3H), 2.94 (s, 1H), 2.84 (s, 1H), 2.35 (d, J = 9.5 Hz, 2H), 1.01 (d, J = 16.5 Hz, 9H). MS m/z (ESI): 474.1 [M + H]⁺. |

| No. | Compound Structure | Compound Name | Starting material or regent different from that in Example 6 | Characterization Data |
|---|---|---|---|---|
| C68 | (structure shown) | 6-((5-fluoro-2-(5-(4,4,4-trifluorobutanoyl)-4,5,6,7-tetrahydrothieno[3,2-c]pyridin-2-yl)pyrimidin-4-yl)amino)isoquinolin-1(2H)-one | (structure shown) in Step 5-B was replaced with (structure shown); and Step 5-A was omitted. | $^1$H NMR (400 MHz, DMSO-d$_6$) δ 11.11 (d, J = 4.6 Hz, 1H), 10.00 (s, 1H), 8.46 (d, J = 3.1 Hz, 1H), 8.29 (d, J = 12.5 Hz, 1H), 8.17 (d, J = 8.8 Hz, 1H), 7.98-7.88 (m, 1H), 7.62 (d, J = 9.3 Hz, 1H), 7.22-7.13 (m, 1H), 6.52 (d, J = 7.0 Hz, 1H), 4.63 (d, J = 18.2 Hz, 2H), 3.87-3.73 (m, 2H), 2.95 (s, 1H), 2.84 (s, 1H), 2.78-2.65 (m, 2H), 2.57 (s, 1H), 2.37 (dd, J = 12.1, 6.1 Hz, 1H). MS m/z (ESI): 518.0 [M + H]$^+$. |
| C69 | (structure shown) | 6-((5-fluoro-2-(5-(4,4,4-trifluorobutanoyl)-4,5,6,7-tetrahydrothieno[3,2-c]pyridin-2-yl)pyrimidin-4-yl)amino)-3,4-dihydroisoquinolin-1(2H)-one | (structure shown) in Step 3 was replaced with (structure shown) and (structure shown) in Step 5-B was replaced with (structure shown); and Step 5-A was omitted. | $^1$H NMR (400 MHz, DMSO-d$_6$) δ 9.88 (s, 1H), 8.44 (t, J = 3.5 Hz, 1H), 7.87 (dd, J = 26.9, 21.1 Hz, 3H), 7.60 (d, J = 9.0 Hz, 1H), 7.15 (d, J = 51.1 Hz, 1H), 4.63 (d, J = 17.8 Hz, 2H), 3.80 (d, J = 18.3 Hz, 2H), 3.41 (s, 2H), 2.96 (d, J = 6.3 Hz, 2H), 2.91-2.65 (m, 4H), 2.08 (s, 2H). MS m/z (ESI) 519.6 [M + H]$^+$. |

Example 7: Preparation of (6-(4-((1-aminoisoquinolin-6-yl)amino)pyrimidin-2-yl)-1-methyl-1H-indol-2-yl)(3,3-difluoroazetidin-1-yl)methanone (C38)

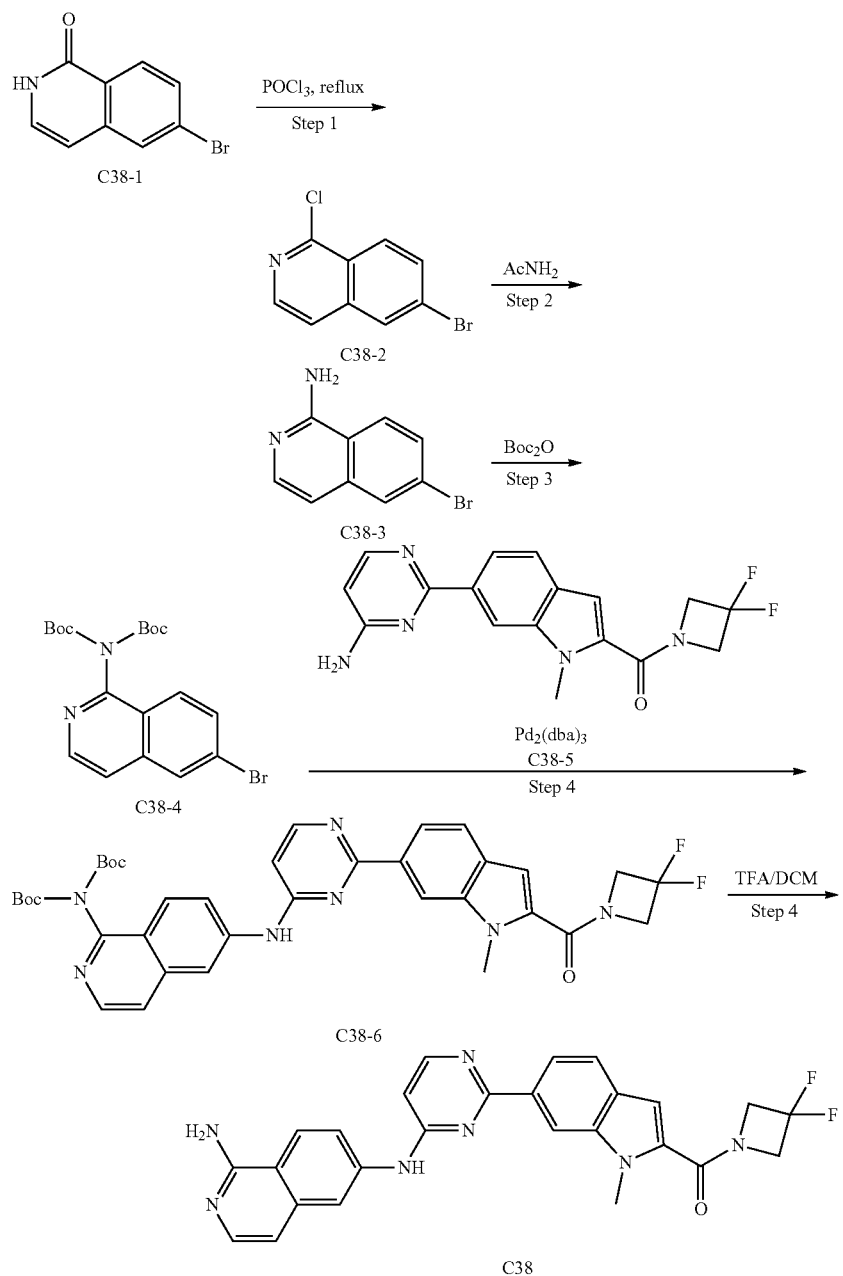

Step 1:

Compound C38-1 (0.5 g, 2.23 mmol) was dissolved in phosphorus oxychloride (5 mL), and the reaction solution was heated to 110° C. and stirred for 2 hours. LC-MS indicated the reaction was complete. The solvent was removed by rotary evaporation, the residue was added with water (10 mL), neutralized with a saturated aqueous solution of sodium bicarbonate, extracted with ethyl acetate (20 mL×2), dried over anhydrous sodium sulfate, filtered, and concentrated under reduced pressure to afford C38-2 (530 mg, yellow solid, yield 97%).

$^1$H NMR (400 MHz, DMSO-d$_6$) δ 8.30 (d, J=5.6 Hz, 1H), 8.21 (d, J=9.0 Hz, 1H), 8.03 (s, 1H), 7.77 (d, J=9.0 Hz, 1H), 7.52 (d, J=5.6 Hz, 1H).

Step 2:

Compound C38-2 (530 mg, 2.18 mmol) and acetamide (1.93 g, 32.7 mmol) were dissolved in NMP (2 mL), potassium carbonate (602 mg, 4.36 mmol) was added, heated to 110° C. and stirred for 2 days. The reaction solution was cooled and then diluted by adding water (20 mL), extracted with ethyl acetate (15 mL×2). The organic phases were combined, washed with water (20 mL) and saturated brine (20 mL), dried over anhydrous sodium sulfate, filtered, and concentrated under reduced pressure. The residue was purified by Flash column chromatography (methanol/dichloromethane, 0~3%), to afford compound C38-3 (60 mg, yellow solid, yield 12.3%).

$^1$H NMR (400 MHz, DMSO-$d_6$) δ 8.13 (d, J=8.8 Hz, 1H), 7.96 (s, 1H), 7.82 (d, J=5.7 Hz, 1H), 7.58 (d, J=8.9 Hz, 1H), 6.91 (s, 2H), 6.87 (d, J=5.7 Hz, 1H).

Step 3:

Compound C38-3 (60 mg, 0.27 mmol) and di-tert-butyl dicarbonate (71 mg, 0.33 mmol) were mixed in tetrahydrofuran (1 mL), DMAP (33 mg, 0.27 mmol) was added at room temperature with stirring, and the reaction was stirred at room temperature for 2 days. LC-MS indicated the reaction was complete. The solvent was removed by evaporation under reduced pressure, to afford a crude product of C38-4 (150 mg, yellowish-brown solid, yield 100%), which was used in the next reaction without purification.

Step 4:

The crude product of Compound C38-4 (130 mg, 0.27 mmol), compound C38-5 (92.6 mg, 0.27 mmol) and cesium carbonate (264 mg, 0.81 mmol) were mixed in 1,4-dioxane (5 mL), purge with $N_2$ was performed for 3 times, and then Pd$_2$(dba)$_3$ (27.5 mg, 0.03 mmol) and Xantphos (52 mg, 0.09 mmol) were added. Purge with N2 was performed again for 3 times, and then the reaction was placed in an oil bath at 100° C. for 16 hours. LC-MS indicated the product formed. The reaction solution was cooled to room temperature, filtered, the filtrate was concentrated under reduced pressure to dryness, and the residue was separated by preparative thin layer chromatography on silica gel (methanol:dichloromethane=1:12), to afford C38-6 (25 mg, yellow solid, yield 13.5%).

MS m/z (ESI): 686.1 [M+H]$^+$.

Step 5:

C38-6 (25 mg, 0.036 mmol) was dissolved in dichloromethane (2 mL), TFA (0.3 mL) was added at room temperature with stirring, and the reaction was stirred at room temperature for 3 hours. LC-MS indicated the reaction was complete. The solvent was removed by evaporation under reduced pressure, the crude product was separated by preparative liquid chromatography (acetonitrile/water (0.1% TFA), 20~60%, 30 minutes) to afford C38 (13 mg, yellow solid, yield 60.2%).

$^1$H NMR (400 MHz, DMSO-$d_6$) δ 12.72 (s, 1H), 10.50 (s, 1H), 8.82 (s, 2H), 8.61 (d, J=3.6 Hz, 1H), 8.59 (s, 1H), 8.55 (d, J=9.2 Hz, 1H), 8.22 (d, J=8.3 Hz, 1H), 8.01 (d, J=9.6 Hz, 1H), 7.79 (d, J=8.4 Hz, 1H), 7.66 (d, J=7.0 Hz, 1H), 7.21 (d, J=7.0 Hz, 1H), 7.10 (s, 1H), 6.93 (d, J=8.0 Hz, 1H), 4.87 (s, 2H), 4.58 (s, 2H), 4.07 (s, 3H). MS m/z (ESI): 486.1 [M+H]$^+$.

The following compounds can be prepared according to methods similar to that described in each of the above Examples.

| Compound No. | Structure | MS m/z (ESI): [M + H] |
|---|---|---|
| C2 | 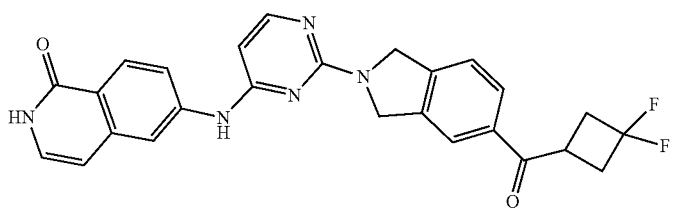 [SMILES: O=C(c1ccc2c(c1)CN(c1nccc(Nc3ccc4c(=O)[nH]ccc4c3)n1)C2)C1CC(F)(F)C1] | 473.6 |
| C4 | 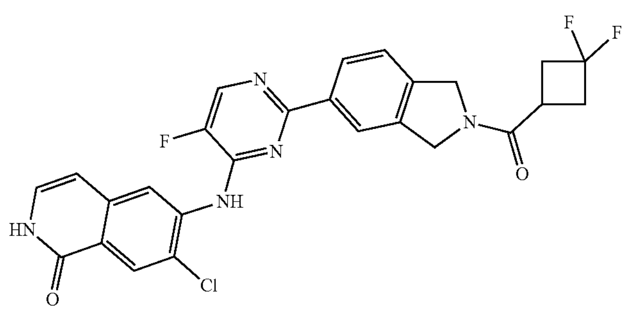 [SMILES: O=C(C1CC(F)(F)C1)N1Cc2ccc(-c3ncc(F)c(Nc4cc5cc[nH]c(=O)c5cc4Cl)n3)cc2C1] | 525.7 |
| C29 | 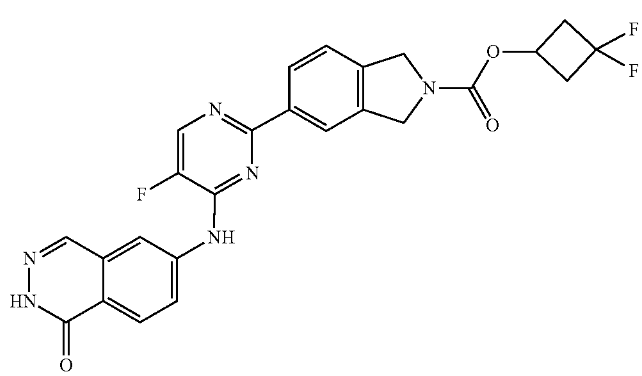 [SMILES: O=C(OC1CC(F)(F)C1)N1Cc2ccc(-c3ncc(F)c(Nc4ccc5c(=O)[nH]ncc5c4)n3)cc2C1] | 508.6 |

-continued

| Compound No. | Structure | MS m/z (ESI): [M + H] |
|---|---|---|
| C32 | 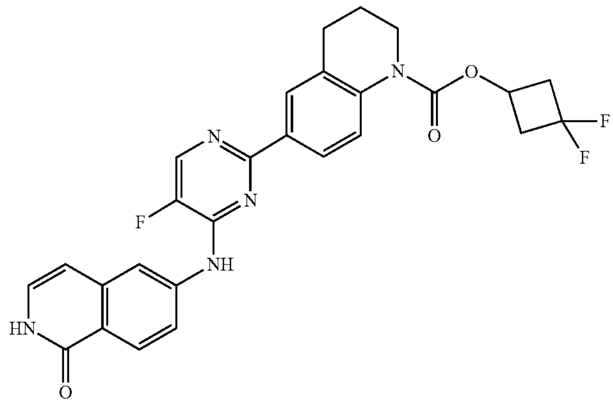 [SMILES: O=C(OC1CC(F)(F)C1)N1CCCc2cc(-c3ncc(F)c(Nc4ccc5c(=O)[nH]ccc5c4)n3)ccc21] | 521.6 |
| C34 | 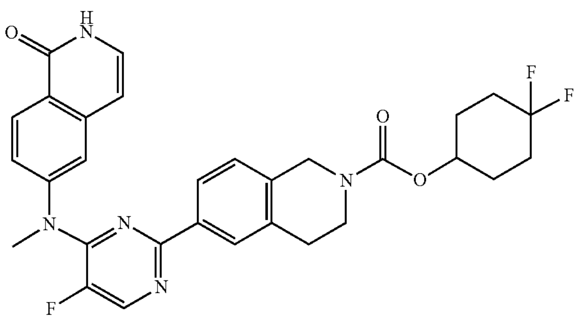 [SMILES: CN(c1ccc2c(=O)[nH]ccc2c1)c1nc(-c2ccc3c(c2)CCN(C(=O)OC2CCC(F)(F)CC2)C3)ncc1F] | 563.8 |
| C58 | 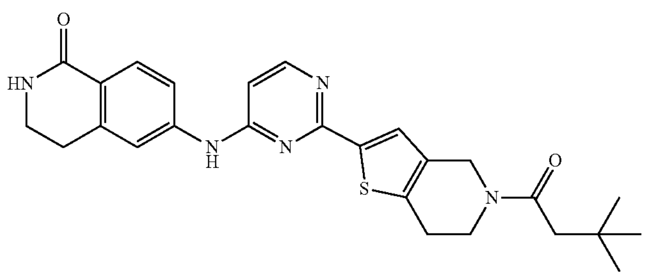 [SMILES: CC(C)(C)CC(=O)N1CCc2sc(-c3nccc(Nc4ccc5c(c4)CCNC5=O)n3)cc2C1] | 475.8 |
| C77 | 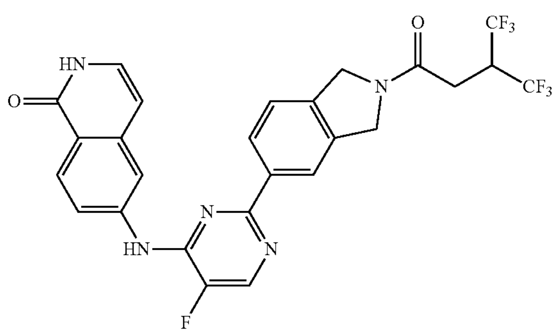 [SMILES: O=C(CC(C(F)(F)F)C(F)(F)F)N1Cc2ccc(-c3ncc(F)c(Nc4ccc5c(=O)[nH]ccc5c4)n3)cc2C1] | 565.6 |
| C80 | 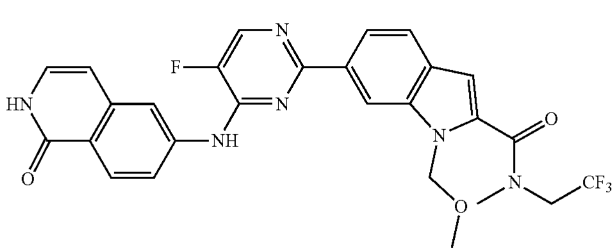 [SMILES: COCn1c(C(=O)N(C)CC(F)(F)F)cc2ccc(-c3ncc(F)c(Nc4ccc5c(=O)[nH]ccc5c4)n3)cc21] | 554.6 |

Biological Assay

The kinase IC$_{50}$ was determined by a commercialized CISBIO kinase detection kit, HTRF KinEASE-STK S2 kit (62ST2PEC). ROCK2 (01-119) employed in the reaction was purchased from Carna Biosciences.

Before the assay, the following working solutions as needed were formulated with corresponding reagents according to the instruction of the kinase detection kit: 1×kinase buffer, 5×STK-S2 substrate working solution (1.5 µM) and 5×ATP working solution (1.5 µM), 5×ROCK2 kinase working solution, 4×Streptavidin-XL665 working solution, and 4×STK-Ab-Cryptate 2 detection solution. Then the assay was performed according to the following procedure.

A solution of a compound at a concentration of 10000 nM was prepared with the 1×kinase buffer containing 2.5% DMSO. Gradient dilution of the solution of the compound was performed with the kinase buffer containing DMSO, so as to obtain solutions of a test compound at 9 different concentrations. In addition to wells of test compounds, a positive well (containing all the reagents except the compound) and a negative well (containing all the reagents except the test compound and kinase) were set. Except for the control wells (positive and negative wells), a solution of a test compound (4 µL) was added to each of the reaction wells, and a solution of 2.5% DMSO was added to the control wells. Then the substrate (2 µM, i.e., 2 µL 5×STK-S2 substrate working solution) was added to each of the reaction wells. The 5×ROCK2 kinase working solution (2 µL, containing 1.4 ng ROCK2 kinase) was added to each of the reaction wells except for the negative well, the volume of which was made up with the 1×kinase buffer (2 µL). The 5×ATP working solution (2 µL) was added to each of the reaction wells, and the mixtures were incubated at room temperature for 2 hours. After the kinase reaction was complete, the 4×Streptavidin-XL665 working solution was added to each of the reaction wells, the solutions were mixed, followed by immediate addition of the 4×STK-Ab-Cryptate 2 detection solution (5 µL), and the mixtures were incubated at room temperature for 1 hour. The fluorescence signal was read on ENVISION (Perkinelmer) (excitation wavelength: 320 inn, and emission wavelength: 665 nm and 615 nm). The inhibitory rate in each well was calculated based on the fluorescence intensity value: ER (Emission Ratio)_(fluorescence intensity at 665 nm/fluorescence intensity at 615 nm); inhibitory rate=(ER$_{positive}$−ER$_{test\ compound}$)/(ER$_{positive}$−ER$_{negative}$)*100%. Curves were plotted and fitted to obtain the median inhibitory concentration (IC$_{50}$) of each teat compound with the PRISM 5.0 software. According to a biological test method similar to the above, the IC$_{50}$ values of the compounds on ROCK1 were also tested. The test results are shown in the following table.

| Compound No. | ROCK2 IC$_{50}$ (nM) | ROCK1 IC$_{50}$ (nM) |
| --- | --- | --- |
| C1 | 129 | >10000 |
| C3 | 287 | >10000 |
| C5 | 13 | >10000 |
| C6 | 76 | >10000 |
| C8 | 16 | >10000 |
| C9 | 4 | >10000 |
| C10 | 11 | >10000 |
| C11 | 34 | >10000 |
| C12 | 17 | >10000 |
| C13 | 38 | >10000 |
| C14 | 28 | >10000 |
| C15 | 79 | >10000 |
| C16 | 19 | >10000 |
| C17 | 421 | >10000 |
| C18 | 31 | >10000 |
| C19 | 25 | >10000 |
| C20 | 238 | >10000 |
| C21 | 108 | >10000 |
| C22 | 130 | >10000 |
| C23 | 173 | >10000 |
| C24 | 222 | >10000 |
| C25 | 45 | >10000 |
| C26 | 356 | >10000 |
| C27 | 8 | >10000 |
| C28 | 6 | >10000 |
| C30 | 216 | >10000 |
| C35 | 93 | >10000 |
| C37 | 117 | >10000 |
| C38 | 264 | >10000 |
| C39 | 102 | >10000 |
| C40 | 270 | >10000 |
| C41 | 151 | >10000 |
| C42 | 31 | >10000 |
| C43 | 71 | >10000 |
| C44 | 57 | >10000 |
| C45 | 491 | >10000 |
| C46 | 21 | >10000 |
| C47 | 15 | >10000 |
| C48 | 13 | >10000 |
| C49 | 7 | >10000 |
| C50 | 280 | >10000 |
| C51 | 53 | >10000 |
| C52 | 28 | >10000 |
| C53 | 135 | >10000 |
| C54 | 17 | >10000 |
| C55 | 51 | >10000 |
| C56 | 24 | >10000 |
| C57 | 16 | >10000 |
| C59 | 33 | >10000 |
| C60 | 13 | >10000 |
| C61 | 170 | >10000 |
| C62 | 139 | >10000 |
| C63 | 24 | >10000 |
| C64 | 109 | >10000 |
| C65 | 80 | >10000 |
| C66 | 82 | >10000 |
| C67 | 101 | >10000 |
| C68 | 9 | >10000 |
| C69 | 45 | >10000 |
| C70 | 15 | >10000 |
| C71 | 25 | >10000 |
| C72 | 24 | >10000 |
| C73 | 78 | >10000 |
| C74 | 54 | >10000 |
| C75 | 37 | >10000 |
| C76 | 49 | >10000 |
| C78 | 40 | >10000 |
| C79 | 46 | >10000 |
| C81 | 129 | >10000 |
| C82 | 129 | >10000 |

According to the above data, the IC$_{50}$ values of the tested compounds on ROCK2 are significantly lower than those on ROCK1, indicating the compound of the present invention has good selectivity towards ROCK2.

Various modifications of the invention in addition to those described herein will become apparent to those skilled in the art from the foregoing description. Such modifications are intended to fall within the scope of the appended claims. Each reference, including all patents, applications, journal articles, books and any other disclosure, referred to herein is hereby incorporated by reference in its entirety.

What is claimed is:

1. A compound or a pharmaceutically acceptable salt, ester, stereoisomer, polymorph, solvate, N-oxide, or isotopically labeled compound thereof, wherein the compound has the structure of Formula (I):

Formula (I)

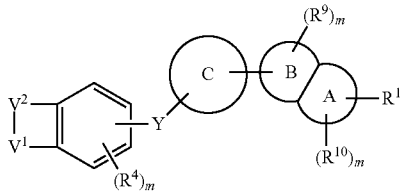

wherein:

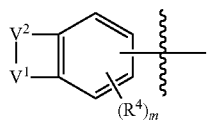

is selected from the group consisting of

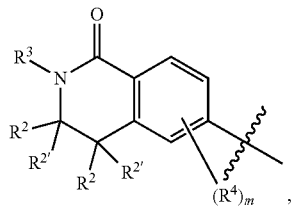,

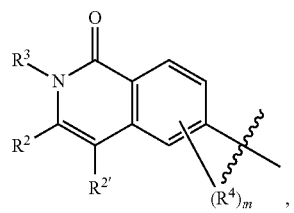,

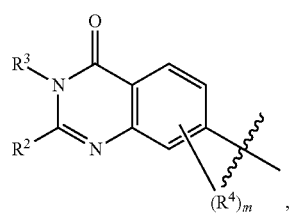,

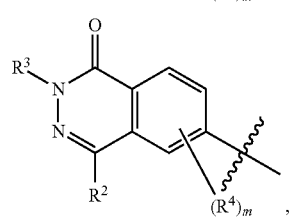,

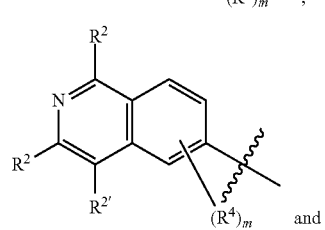 and

-continued

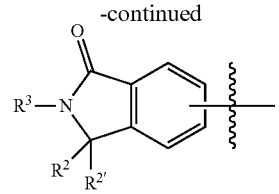;

Y is selected from the group consisting of O and NR;

R is selected from the group consisting of H, $C_{1-6}$ alkyl, $C_{2-6}$ alkenyl, $C_{2-6}$ alkynyl, saturated or partially unsaturated $C_{3-10}$ cyclic hydrocarbyl, saturated or partially unsaturated 3-10-membered heterocyclyl, $C_{6-10}$ aryl, 5-14-membered heteroaryl and $C_{6-12}$ aralkyl, and at most 2 ring members in the cyclic hydrocarbyl and heterocyclyl are C(=O);

ring A and ring B are each independently selected from the group consisting of saturated or partially unsaturated $C_{3-10}$ hydrocarbon ring, saturated or partially unsaturated 3-10-membered heterocycle, $C_{6-10}$ aromatic ring and 5-14-membered heteroaromatic ring, and at most 2 ring members in the hydrocarbon ring and heterocycle are C(=O);

ring C is

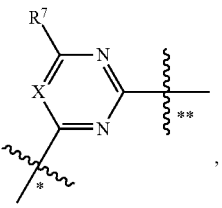, which is attached to Y at the position labeled *, and is attached to ring B at the position labeled **;

X is selected from the group consisting of $CR^8$ and N;

$R^1$ is selected from the group consisting of —C(=O)$R^{1a}$, —C(=O)O$R^{1a}$ and —C(=O)N$R^{1a}R^{1b}$;

$R^{1a}$ and $R^{1b}$ are each independently selected from the group consisting of H, halogen, amino, cyano, nitro, $C_{1-6}$ alkyl, $C_{2-6}$ alkenyl, $C_{2-6}$ alkynyl, $C_{3-10}$ cyclic hydrocarbyl, 3-10-membered heterocyclyl, $C_{6-10}$ aryl, 5-14-membered heteroaryl, $C_{6-12}$ aralkyl, —C(=O)$R^5$, —OC(=O)$R^5$, —C(=O)O$R^5$, —O$R^5$, —S$R^5$, —S(=O)$R^5$, —S(=O)$_2R^5$, —S(=O)$_2$N$R^5R^6$, —N$R^5R^6$, —C(=O)N$R^5R^6$, —N$R^5$—C(=O)$R^6$, —N$R^5$—C(=O)O$R^6$, —N$R^5$—S(=O)$_2$—$R^6$, —N$R^5$—C(=O)—N$R^5R^6$, —$C_{1-6}$ alkylene-N$R^5R^6$, —$C_{1-6}$ alkylene-O$R^5$ and —O—$C_{1-6}$ alkylene-N$R^5R^6$; alternatively, $R^{1a}$ and $R^{1b}$ together with the atom to which they are attached form a 3-12-membered heterocycle or heteroaromatic ring;

$R^2$, $R^{2'}$, $R^3$, $R^4$, $R^7$, $R^8$, $R^9$ and $R^{10}$, at each occurrence, are each independently selected from the group consisting of H, halogen, amino, cyano, nitro, $C_{1-6}$ alkyl, $C_{2-6}$ alkenyl, $C_{2-6}$ alkynyl, $C_{3-10}$ cyclic hydrocarbyl, 3-10-membered heterocyclyl, $C_{6-10}$ aryl, 5-14-membered heteroaryl, $C_{6-12}$ aralkyl, —C(=O)$R^5$, —OC(=O)$R^5$, —C(=O)O$R^5$, —O$R^5$, —S$R^5$, —S(=O)$R^5$, —S(=O)$_2 R^5$, —S(=O)$_2$N$R^5R^6$, —N$R^5R^6$, —C(=O)N$R^5R^6$, —N$R^5$—C(=O)$R^6$, —N$R^5$—C(=O)O$R^6$, —N$R^5$—S(=O)$_2$—$R^6$, —N$R^5$—C(=O)—N$R^5R^6$, —$C_{1-6}$ alkylene-N$R^5R^6$, —$C_{1-6}$ alkylene-O(P=O)(OH)$_2$ and —O—$C_{1-6}$ alkylene-$NR^5R^6$; alternatively, $R^7$ and $R^8$ together with the group to which they are attached form a $C_{6-10}$ aromatic ring or 5-14-membered heteroaromatic ring;

the alkyl, alkylene, alkenyl, alkenylene, alkynyl, cyclic hydrocarbyl, hydrocarbon ring, heterocyclyl, heterocycle, aryl, aromatic ring, heteroaryl, heteroaromatic ring and aralkyl, at each occurrence, are each optionally substituted with one or more substituents independently selected from the group consisting of: halogen, hydroxyl, oxo, amino, cyano, nitro, $C_{1-6}$ alkyl, $C_{2-6}$ alkenyl, $C_{2-6}$ alkynyl, $C_{3-6}$ cyclic hydrocarbyl, 3-10-membered heterocyclyl, $C_{6-10}$ aryl, 5-14-membered heteroaryl, $C_{6-12}$ aralkyl, =N—$OR^5$, —C(=NH)$NH_2$, —C(=O)$R^5$, —OC(=O)$R^5$, —C(=O)$OR^5$, —$OR^5$, —$SR^5$, —S(=O)$R^5$, —S(=O)$_2R^5$, —S(=O)$_2NR^5R^6$, —$NR^5R^6$, —C(=O)$NR^5R^6$, —$NR^5$—C(=O)$R^6$, —$NR^5$—C(=O)$OR^6$, —$NR^5$—S(=O)$_2$—$R^6$, —$NR^5$—C(=O)—$NR^5R^6$, —$C_{1-6}$ alkylene-$NR^5R^6$ and —O—$C_{1-6}$ alkylene-$NR^5R^6$, and the alkyl, alkylene, alkenyl, alkynyl, cyclic hydrocarbyl, heterocyclyl, aryl, heteroaryl and aralkyl are further optionally substituted with one or more substituents independently selected from the group consisting of: halogen, hydroxyl, oxo, amino, cyano, nitro, $C_{1-6}$ alkyl, $C_{3-6}$ cyclic hydrocarbyl, 3-10-membered heterocyclyl, $C_{6-10}$ aryl, 5-14-membered heteroaryl and $C_{6-12}$ aralkyl;

$R^5$ and $R^6$, at each occurrence, are each independently selected from the group consisting of H, $C_{1-6}$ alkyl, $C_{3-10}$ cyclic hydrocarbyl, 3-10-membered heterocyclyl, $C_{6-10}$ aryl, 5-14-membered heteroaryl and $C_{6-12}$ aralkyl; alternatively, when $R^5$ and $R^6$ are attached to a same nitrogen atom, $R^5$ and $R^6$ together with the atom to which they are attached optionally form a 3-12-membered heterocycle or heteroaromatic ring; and m, at each occurrence, is each independently an integer of 0, 1, 2 or 3.

2. The compound according to claim 1 or a pharmaceutically acceptable salt, ester, stereoisomer, polymorph, solvate, N-oxide, or isotopically labeled compound thereof, wherein Y is selected from the group consisting of O, NH and $NCH_3$.

3. The compound according to claim 1 or a pharmaceutically acceptable salt, ester, stereoisomer, polymorph, solvate, N-oxide, or isotopically labeled compound thereof, wherein

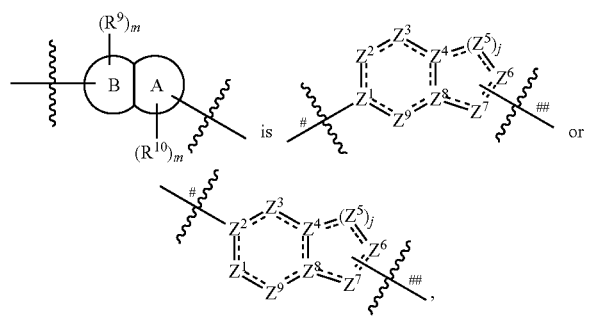

is the above group is attached to ring C at either of the two positions labeled # or ##, and is attached to $R^1$ at the other position, wherein --- represents either a single or a double bond, and the adjacent bonds are not double bonds simultaneously;

$Z^1, Z^2, Z^3, Z^4, Z^5, Z^6, Z^7, Z^8$ and $Z^9$, at each occurrence, are each independently selected from the group consisting of C, $CR^9$, $C(R^9)_2$, $CR^{10}$, $C(R^{10})_2$, C(=O), N, $NR^9$, $NR^{10}$, O and S;

j is 0, 1, 2, 3 or 4;

provided that at most two groups among $Z^1$-$Z^9$ are simultaneously C(=O);

$R^9$ and $R^{10}$, at each occurrence, are each independently selected from the group consisting of halogen, methyl, ethyl, propyl, vinyl, cyclopropyl, cyclobutyl, cyclopentyl, oxetanyl, monofluoromethyl, difluoromethyl, trifluoromethyl, —$CH_2CHF_2$, acetyl, —$OCH_3$, —$CH_2OH$, —$CH_2OCH_3$, —$CH_2CH_2OCH_3$, —$CH_2$—O(P=O)$(OH)_2$,

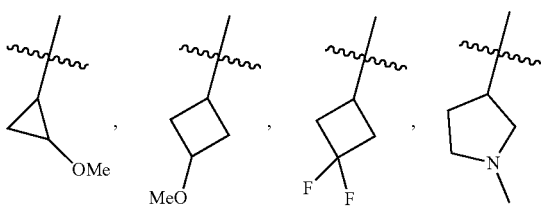

and —$CH_2CH_2$—N$(CH_3)_2$.

4. The compound according to claim 1 or a pharmaceutically acceptable salt, ester, stereoisomer, polymorph, solvate, N-oxide, or isotopically labeled compound thereof, wherein ring C is selected from the group consisting of

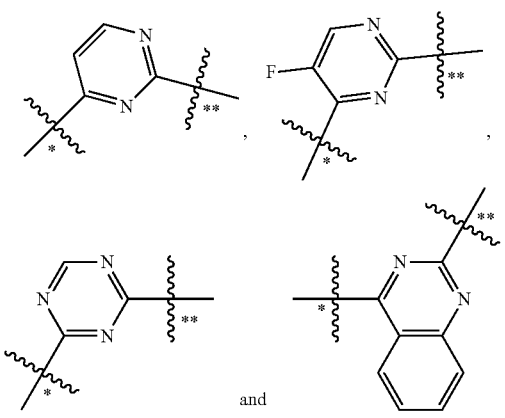

the above group is attached to Y at either of the two positions labeled * or **, and is attached to ring B at the other position.

5. The compound according to claim 1 or a pharmaceutically acceptable salt, ester, stereoisomer, polymorph, solvate, N-oxide, or isotopically labeled compound thereof, wherein

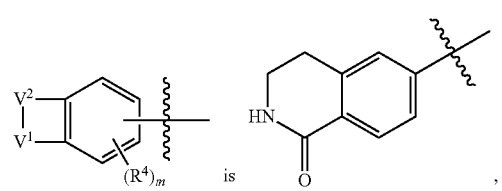

is

147
-continued

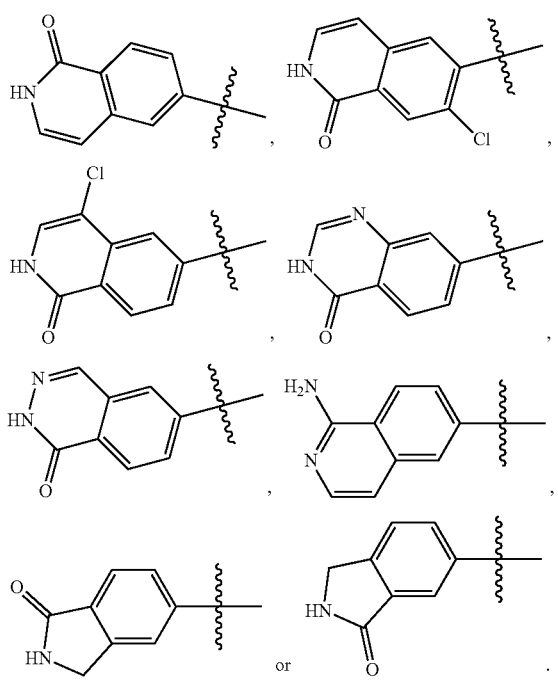

6. The compound according to claim 1 or a pharmaceutically acceptable salt, ester, stereoisomer, polymorph, solvate, N-oxide, or isotopically labeled compound thereof, wherein $R^1$ is selected from the group consisting of

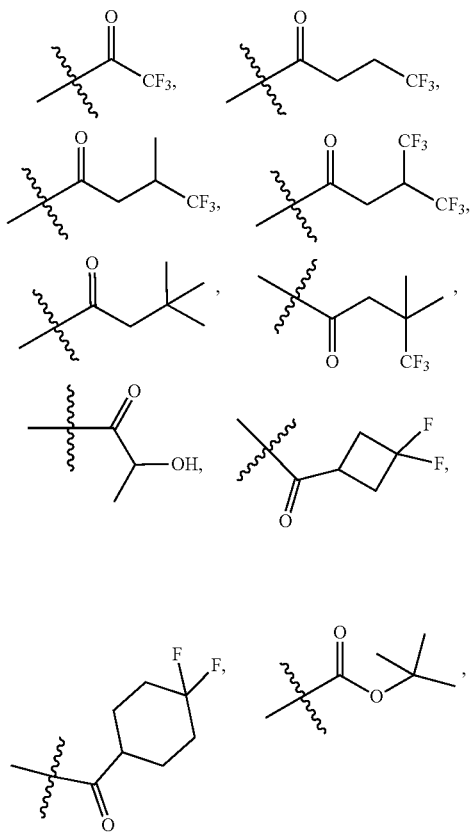

148
-continued

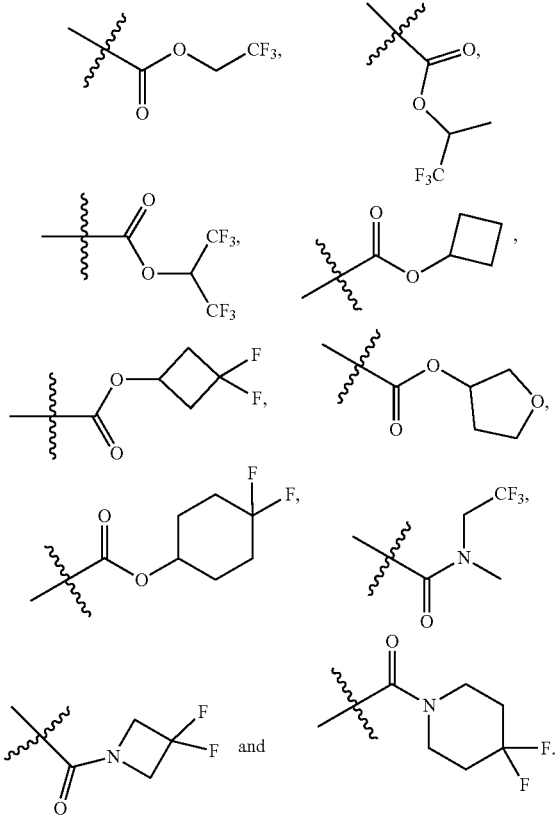

7. The compound according to claim 1 or a pharmaceutically acceptable salt, ester, stereoisomer, polymorph, solvate, N-oxide, or isotopically labeled compound thereof, wherein the compound has the structure of any of the following formulae:

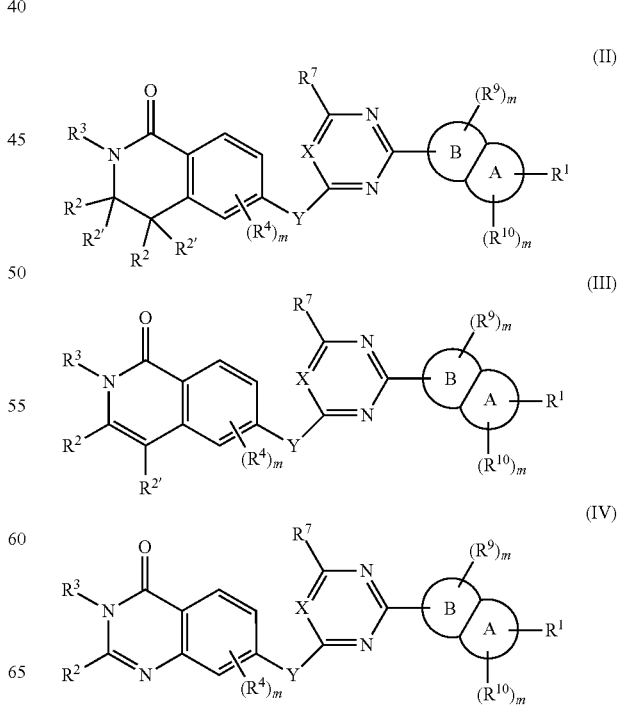

-continued
(V)
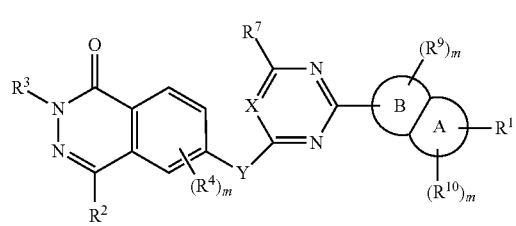
(VI)
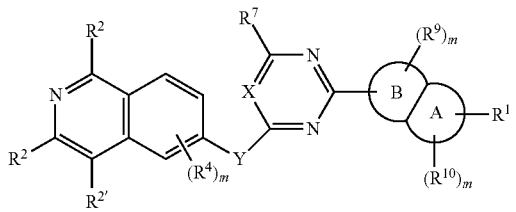
(VII)
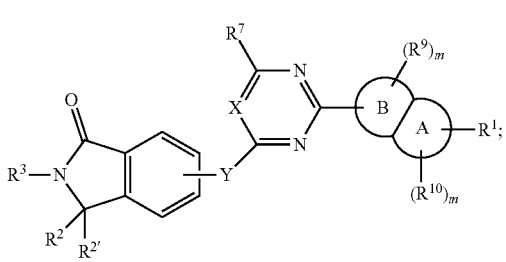
wherein Y is NR.
8. The compound according to claim 1 or a pharmaceutically acceptable salt, ester, stereoisomer, polymorph, solvate, N-oxide, or isotopically labeled compound thereof, wherein the compound has the following structure:
| No. | Structure |
|---|---|
| C1. | 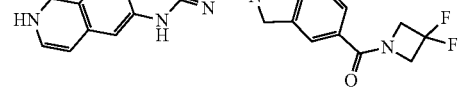 |
| C2. | 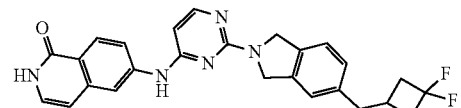 |
| C3. | 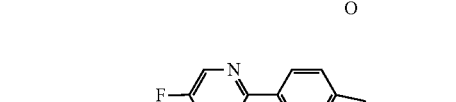 |
| C4. | 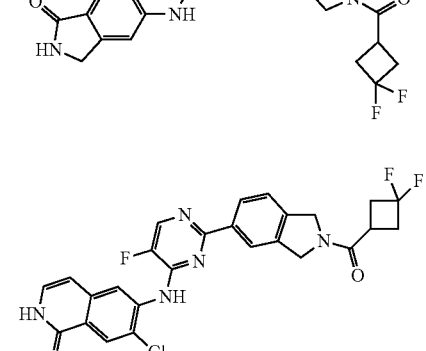 |
| C5. | 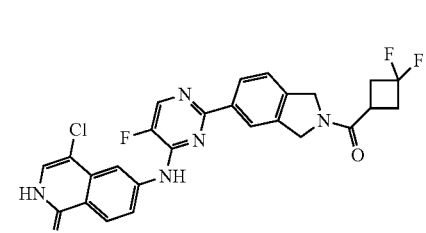 |

-continued

| No. | Structure |
|---|---|
| C6. | 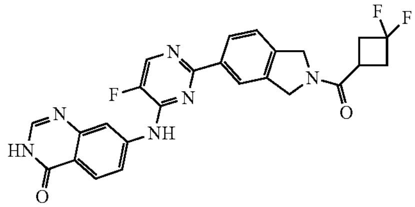 [SMILES: O=C(C1CC(F)(F)C1)N1Cc2ccc(-c3ncc(F)c(Nc4ccc5c(=O)[nH]cnc5c4)n3)cc2C1] |
| C7. | 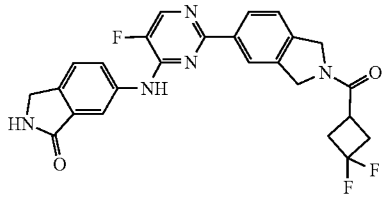 [SMILES: O=C1NCc2ccc(Nc3nc(-c4ccc5c(c4)CN(C(=O)C4CC(F)(F)C4)C5)ncc3F)cc21] |
| C8. | 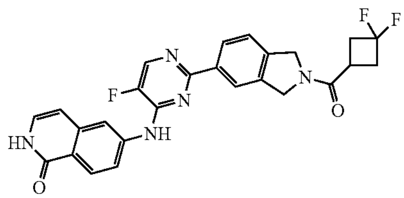 |
| C9. | 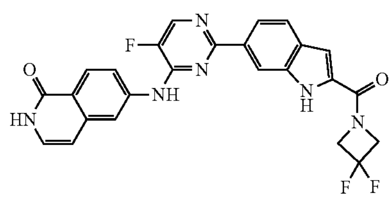 [SMILES: O=C(c1cc2ccc(-c3ncc(F)c(Nc4ccc5c(=O)[nH]ccc5c4)n3)cc2[nH]1)N1CC(F)(F)C1] |
| C10. | 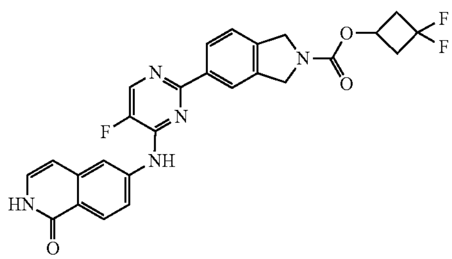 [SMILES: O=C(OC1CC(F)(F)C1)N1Cc2ccc(-c3ncc(F)c(Nc4ccc5c(=O)[nH]ccc5c4)n3)cc2C1] |
| C11. | 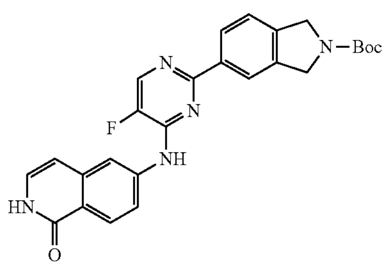 [SMILES: CC(C)(C)OC(=O)N1Cc2ccc(-c3ncc(F)c(Nc4ccc5c(=O)[nH]ccc5c4)n3)cc2C1] |
| C12. | 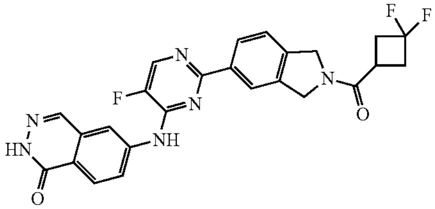 [SMILES: O=C(C1CC(F)(F)C1)N1Cc2ccc(-c3ncc(F)c(Nc4ccc5c(=O)[nH]ncc5c4)n3)cc2C1] |

-continued

| No. | Structure |
|---|---|
| C13. | 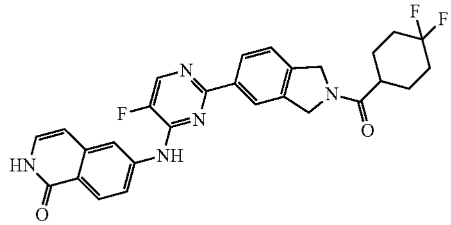 [SMILES: O=C(C1CCC(F)(F)CC1)N1Cc2ccc(-c3ncc(F)c(Nc4ccc5c(=O)[nH]ccc5c4)n3)cc2C1] |
| C14. | 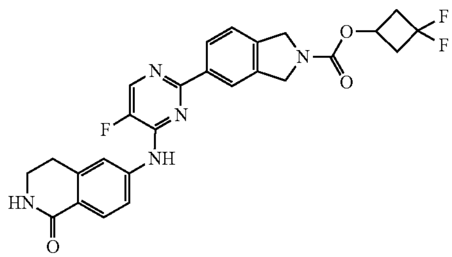 [SMILES: O=C1NCCc2cc(Nc3nc(-c4ccc5c(c4)CN(C(=O)OC4CC(F)(F)C4)C5)ncc3F)ccc21] |
| C15. | 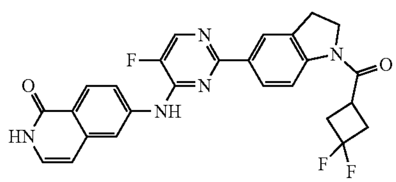 [SMILES: O=C(C1CC(F)(F)C1)N1CCc2cc(-c3ncc(F)c(Nc4ccc5c(=O)[nH]ccc5c4)n3)ccc21] |
| C16. | 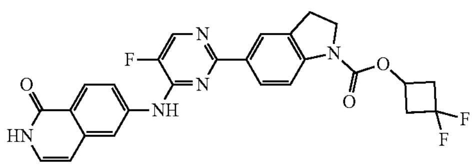 [SMILES: O=C(OC1CC(F)(F)C1)N1CCc2cc(-c3ncc(F)c(Nc4ccc5c(=O)[nH]ccc5c4)n3)ccc21] |
| C17. | 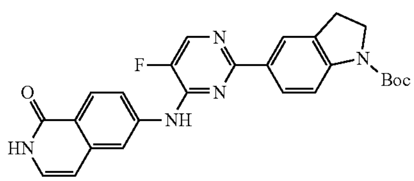 [SMILES: CC(C)(C)OC(=O)N1CCc2cc(-c3ncc(F)c(Nc4ccc5c(=O)[nH]ccc5c4)n3)ccc21] |
| C18. | 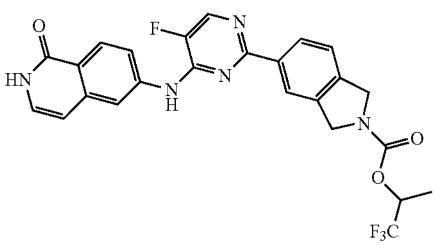 [SMILES: CC(OC(=O)N1Cc2ccc(-c3ncc(F)c(Nc4ccc5c(=O)[nH]ccc5c4)n3)cc2C1)C(F)(F)F] |
| C19. | 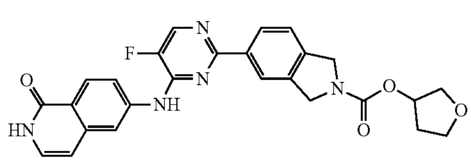 [SMILES: O=C(OC1CCOC1)N1Cc2ccc(-c3ncc(F)c(Nc4ccc5c(=O)[nH]ccc5c4)n3)cc2C1] |
| C20. | 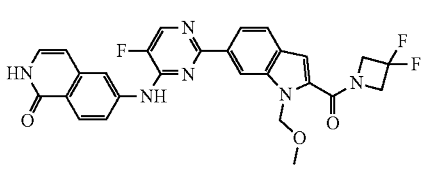 [SMILES: COCn1c(C(=O)N2CC(F)(F)C2)cc2ccc(-c3ncc(F)c(Nc4ccc5c(=O)[nH]ccc5c4)n3)cc21] |

-continued
| No. | Structure |
|---|---|
| C21. | 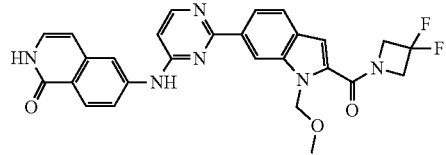 [SMILES: COCn1c(C(=O)N2CC(F)(F)C2)cc2ccc(-c3nccc(Nc4ccc5c(=O)[nH]ccc5c4)n3)cc21] |
| C22. | 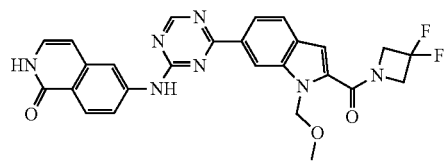 [SMILES: COCn1c(C(=O)N2CC(F)(F)C2)cc2ccc(-c3ncnc(Nc4ccc5c(=O)[nH]ccc5c4)n3)cc21] |
| C23. | 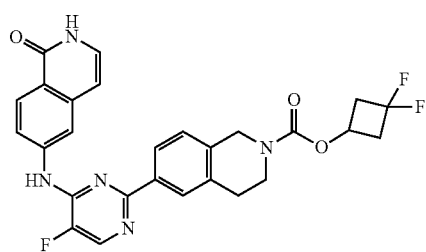 [SMILES: O=C(OC1CC(F)(F)C1)N1CCc2cc(-c3ncc(F)c(Nc4ccc5c(=O)[nH]ccc5c4)n3)ccc2C1] |
| C24. | 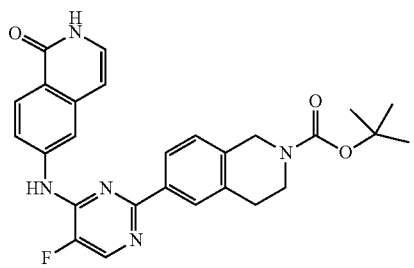 [SMILES: CC(C)(C)OC(=O)N1CCc2cc(-c3ncc(F)c(Nc4ccc5c(=O)[nH]ccc5c4)n3)ccc2C1] |
| C25. | 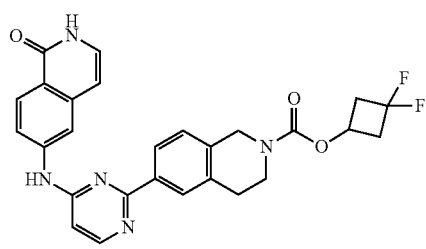 [SMILES: O=C(OC1CC(F)(F)C1)N1CCc2cc(-c3nccc(Nc4ccc5c(=O)[nH]ccc5c4)n3)ccc2C1] |
| C26. | 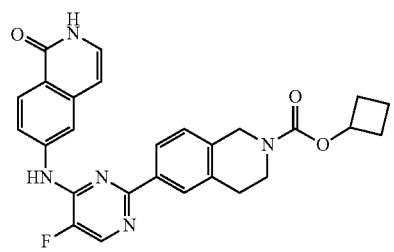 [SMILES: O=C(OC1CCC1)N1CCc2cc(-c3ncc(F)c(Nc4ccc5c(=O)[nH]ccc5c4)n3)ccc2C1] |

| No. | Structure |
|---|---|
| C27. | 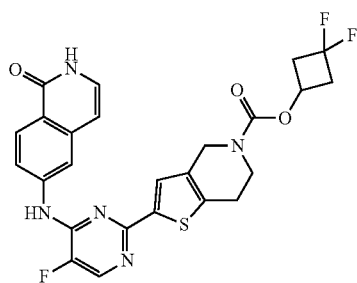 [SMILES: O=C(OC1CC(F)(F)C1)N1CCc2sc(-c3ncc(F)c(Nc4ccc5c(=O)[nH]ccc5c4)n3)cc2C1] |
| C28. | 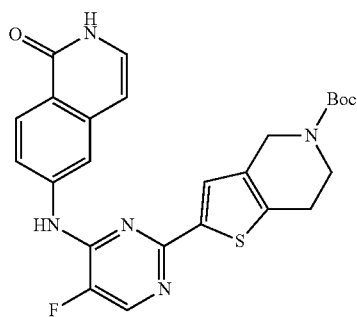 [SMILES: CC(C)(C)OC(=O)N1CCc2sc(-c3ncc(F)c(Nc4ccc5c(=O)[nH]ccc5c4)n3)cc2C1] |
| C29. | 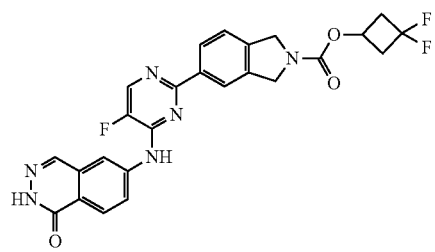 [SMILES: O=C(OC1CC(F)(F)C1)N1Cc2ccc(-c3ncc(F)c(Nc4ccc5c(=O)[nH]ncc5c4)n3)cc2C1] |
| C30. | 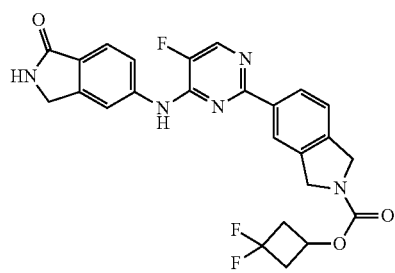 [SMILES: O=C1NCc2cc(Nc3nc(-c4ccc5c(c4)CN(C(=O)OC4CC(F)(F)C4)C5)ncc3F)ccc21] |
| C31. | 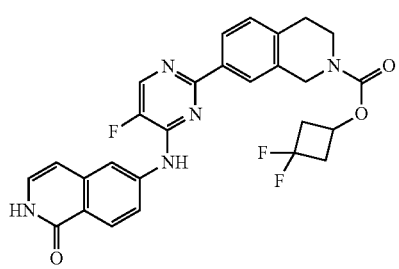 [SMILES: O=C(OC1CC(F)(F)C1)N1CCc2ccc(-c3ncc(F)c(Nc4ccc5c(=O)[nH]ccc5c4)n3)cc2C1] |

-continued
| No. | Structure |
|---|---|
| C32. | 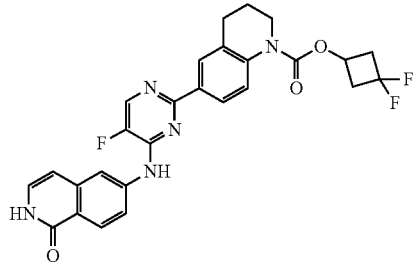 [SMILES: O=C(OC1CC(F)(F)C1)N1CCCc2cc(-c3ncc(F)c(Nc4ccc5c(=O)[nH]ccc5c4)n3)ccc21] |
| C33. | 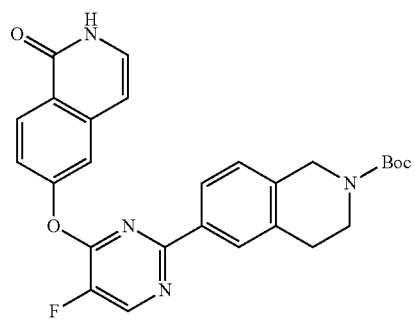 [SMILES: CC(C)(C)OC(=O)N1CCc2cc(-c3ncc(F)c(Oc4ccc5c(=O)[nH]ccc5c4)n3)ccc2C1] |
| C34. | 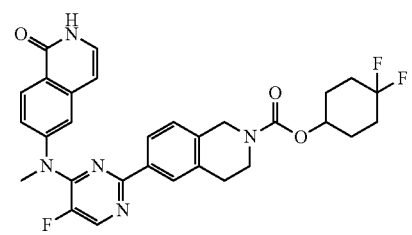 [SMILES: CN(c1ccc2c(=O)[nH]ccc2c1)c1nc(-c2ccc3c(c2)CCN(C(=O)OC2CCC(F)(F)CC2)C3)ncc1F] |
| C35. | 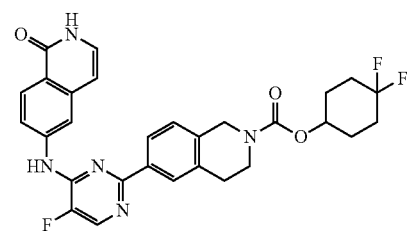 [SMILES: O=C(OC1CCC(F)(F)CC1)N1CCc2cc(-c3ncc(F)c(Nc4ccc5c(=O)[nH]ccc5c4)n3)ccc2C1] |
| C36. | 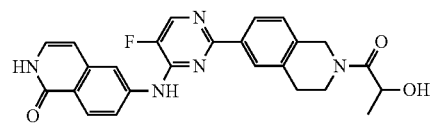 |
| C37. | 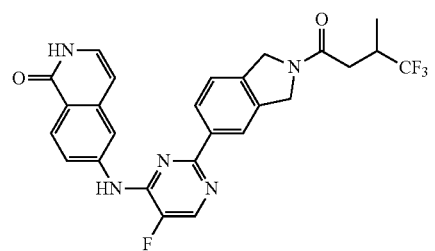 [SMILES: CC(CC(=O)N1Cc2ccc(-c3ncc(F)c(Nc4ccc5c(=O)[nH]ccc5c4)n3)cc2C1)C(F)(F)F] |

| No. | Structure |
|---|---|
| C38. | 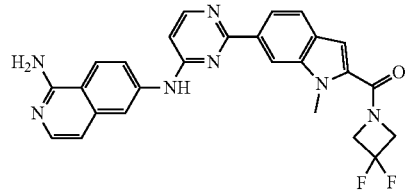 [SMILES: Cn1c(C(=O)N2CC(F)(F)C2)cc2ccc(-c3nccc(Nc4ccc5c(N)nccc5c4)n3)cc21] |
| C39. | 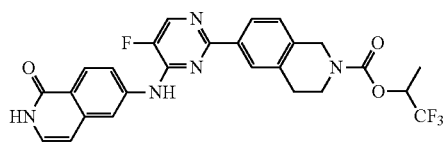 |
| C40. | 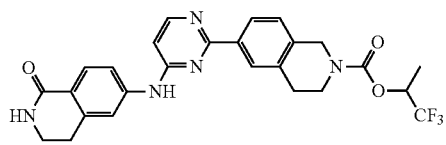 |
| C41. | 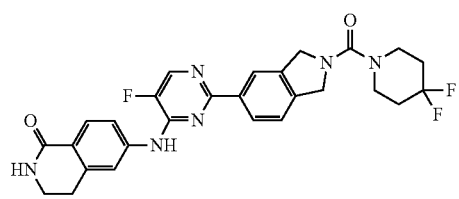 [SMILES: O=C1NCCc2cc(Nc3nc(-c4ccc5c(c4)CN(C(=O)N4CCC(F)(F)CC4)C5)ncc3F)ccc21] |
| C42. | 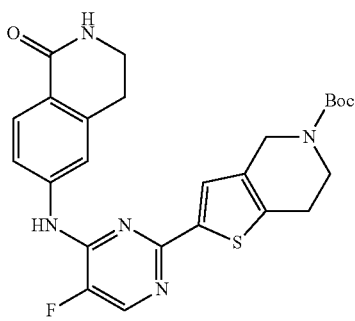 |
| C43. | 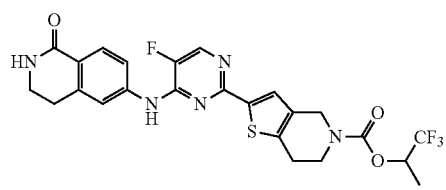 |
| C44. | 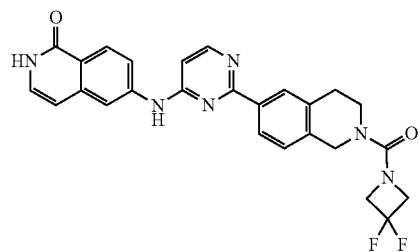 [SMILES: O=C(N1CCc2cc(-c3nccc(Nc4ccc5c(=O)[nH]ccc5c4)n3)ccc2C1)N1CC(F)(F)C1] |

-continued

| No. | Structure |
|---|---|
| C45. | 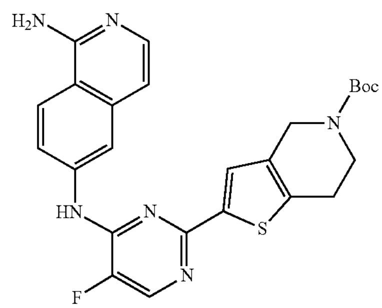 [SMILES: CC(C)(C)OC(=O)N1CCc2sc(-c3ncc(F)c(Nc4ccc5c(N)nccc5c4)n3)cc2C1] |
| C46. | 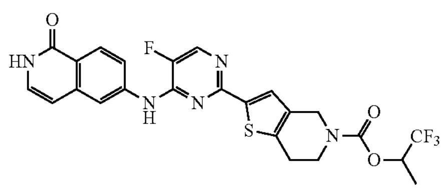 [SMILES: CC(OC(=O)N1CCc2sc(-c3ncc(F)c(Nc4ccc5c(=O)[nH]ccc5c4)n3)cc2C1)C(F)(F)F] |
| C47. | 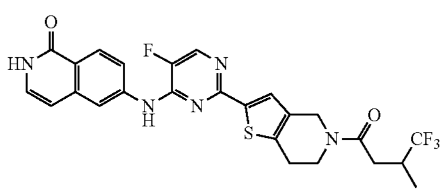 [SMILES: CC(CC(=O)N1CCc2sc(-c3ncc(F)c(Nc4ccc5c(=O)[nH]ccc5c4)n3)cc2C1)C(F)(F)F] |
| C48. | 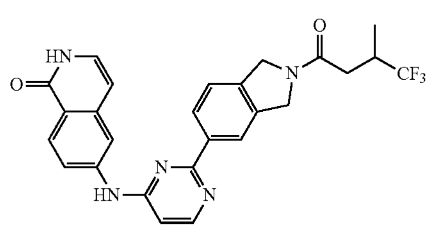 [SMILES: CC(CC(=O)N1Cc2ccc(-c3nccc(Nc4ccc5c(=O)[nH]ccc5c4)n3)cc2C1)C(F)(F)F] |
| C49. | 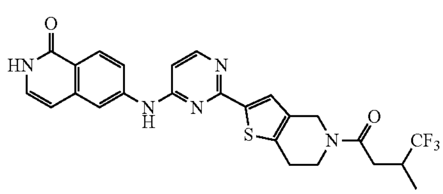 [SMILES: CC(CC(=O)N1CCc2sc(-c3nccc(Nc4ccc5c(=O)[nH]ccc5c4)n3)cc2C1)C(F)(F)F] |
| C50. | 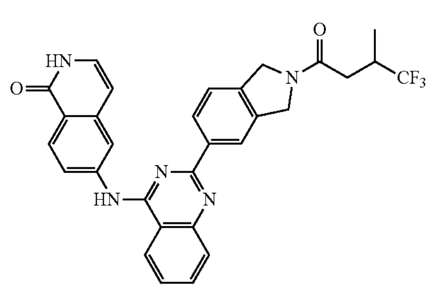 [SMILES: CC(CC(=O)N1Cc2ccc(-c3nc(Nc4ccc5c(=O)[nH]ccc5c4)c4ccccc4n3)cc2C1)C(F)(F)F] |

| No. | Structure |
|---|---|
| C51. | 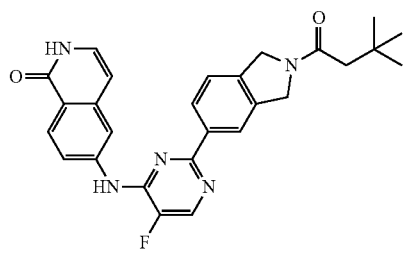 [SMILES: CC(C)(C)CC(=O)N1Cc2ccc(-c3ncc(F)c(Nc4ccc5c(=O)[nH]ccc5c4)n3)cc2C1] |
| C52. | 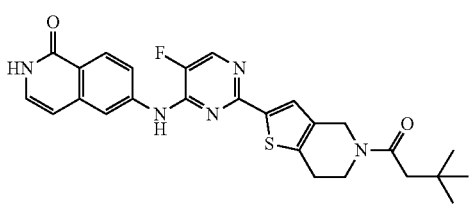 |
| C53. | 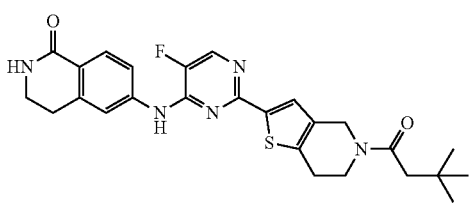 [SMILES: CC(C)(C)CC(=O)N1CCc2sc(-c3ncc(F)c(Nc4ccc5c(c4)CCNC5=O)n3)cc2C1] |
| C54. | 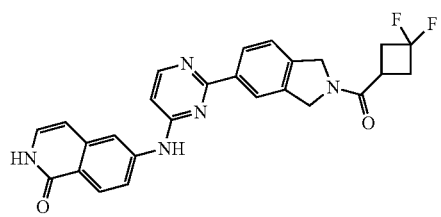 [SMILES: O=C(C1CC(F)(F)C1)N1Cc2ccc(-c3nccc(Nc4ccc5c(=O)[nH]ccc5c4)n3)cc2C1] |
| C55. | 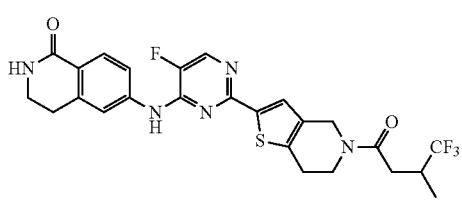 [SMILES: CC(CC(=O)N1CCc2sc(-c3ncc(F)c(Nc4ccc5c(c4)CCNC5=O)n3)cc2C1)C(F)(F)F] |
| C56. | 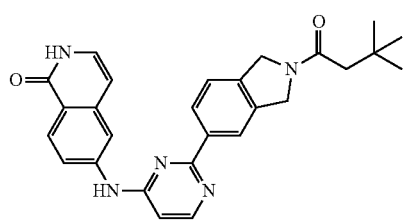 [SMILES: CC(C)(C)CC(=O)N1Cc2ccc(-c3nccc(Nc4ccc5c(=O)[nH]ccc5c4)n3)cc2C1] |
| C57. | 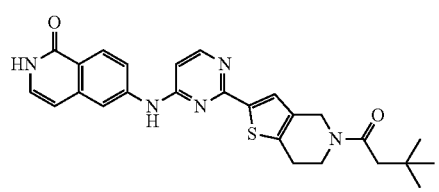 [SMILES: CC(C)(C)CC(=O)N1CCc2sc(-c3nccc(Nc4ccc5c(=O)[nH]ccc5c4)n3)cc2C1] |

-continued
| No. | Structure |
|---|---|
| C58. | 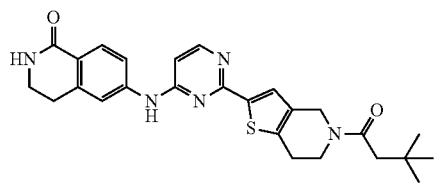 [SMILES: CC(C)(C)CC(=O)N1CCc2sc(-c3nccc(Nc4ccc5c(c4)CCNC5=O)n3)cc2C1] |
| C59. | 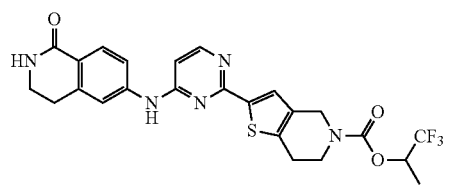 [SMILES: CC(OC(=O)N1CCc2sc(-c3nccc(Nc4ccc5c(c4)CCNC5=O)n3)cc2C1)C(F)(F)F] |
| C60. | 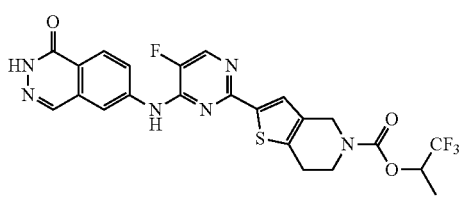 [SMILES: CC(OC(=O)N1CCc2sc(-c3ncc(F)c(Nc4ccc5c(=O)[nH]ncc5c4)n3)cc2C1)C(F)(F)F] |
| C61. | 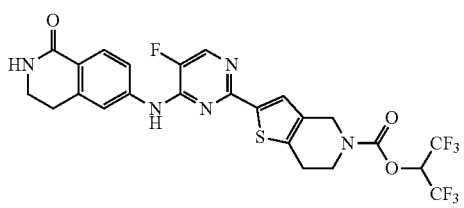 [SMILES: O=C1NCCc2cc(Nc3nc(-c4cc5c(s4)CCN(C(=O)OC(C(F)(F)F)C(F)(F)F)C5)ncc3F)ccc21] |
| C62. | 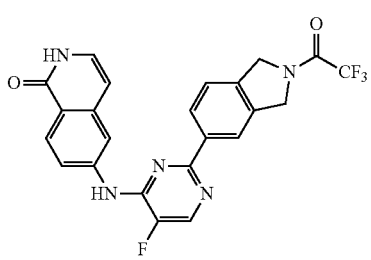 [SMILES: O=C(N1Cc2ccc(-c3ncc(F)c(Nc4ccc5c(=O)[nH]ccc5c4)n3)cc2C1)C(F)(F)F] |
| C63. | 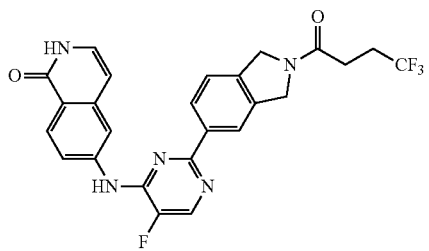 [SMILES: O=C(CCC(F)(F)F)N1Cc2ccc(-c3ncc(F)c(Nc4ccc5c(=O)[nH]ccc5c4)n3)cc2C1] |
| C64. | 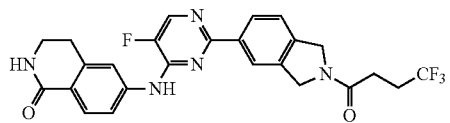 |

-continued
| No. | Structure |
|---|---|
| C65. | 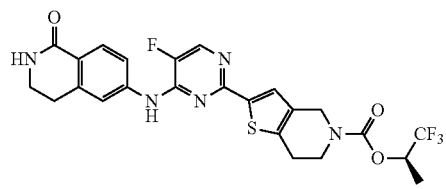 [SMILES: C[C@@H](OC(=O)N1CCc2sc(-c3ncc(F)c(Nc4ccc5c(c4)CCNC5=O)n3)cc2C1)C(F)(F)F] |
| C66. | 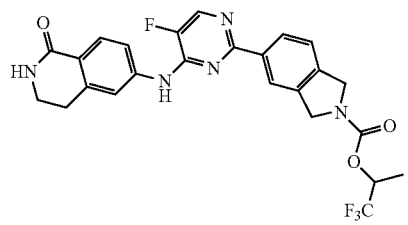 [SMILES: CC(CC(=O)N1Cc2ccc(-c3ncc(F)c(Nc4ccc5c(c4)CCNC5=O)n3)cc2C1)C(F)(F)F] |
| C67. | 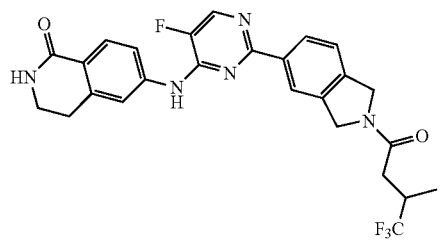 |
| C68. | 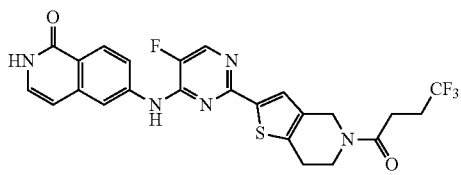 [SMILES: O=C(CCC(F)(F)F)N1CCc2sc(-c3ncc(F)c(Nc4ccc5c(=O)[nH]ccc5c4)n3)cc2C1] |
| C69. | 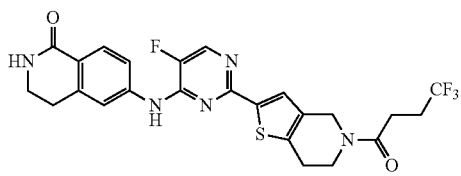 [SMILES: O=C1NCCc2cc(Nc3nc(-c4cc5c(s4)CCN(C(=O)CCC(F)(F)F)C5)ncc3F)ccc21] |
| C70. | 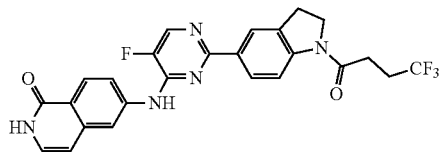 [SMILES: O=C(CCC(F)(F)F)N1CCc2cc(-c3ncc(F)c(Nc4ccc5c(=O)[nH]ccc5c4)n3)ccc21] |
| C71. | 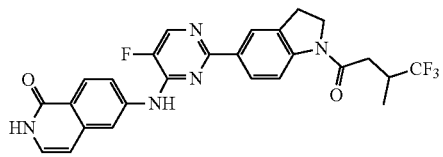 [SMILES: CC(CC(=O)N1CCc2cc(-c3ncc(F)c(Nc4ccc5c(=O)[nH]ccc5c4)n3)ccc21)C(F)(F)F] |

| No. | Structure |
|---|---|
| C72. | 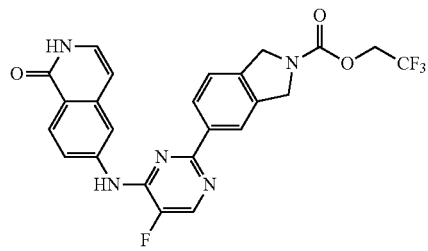 [SMILES: O=C(OCC(F)(F)F)N1Cc2ccc(-c3ncc(F)c(Nc4ccc5c(=O)[nH]ccc5c4)n3)cc2C1] |
| C73. | 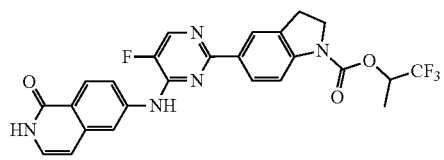 [SMILES: CC(OC(=O)N1CCc2cc(-c3ncc(F)c(Nc4ccc5c(=O)[nH]ccc5c4)n3)ccc21)C(F)(F)F] |
| C74. | 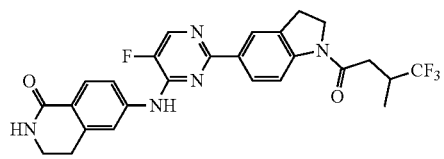 [SMILES: CC(CC(=O)N1CCc2cc(-c3ncc(F)c(Nc4ccc5c(c4)CCNC5=O)n3)ccc21)C(F)(F)F] |
| C75. | 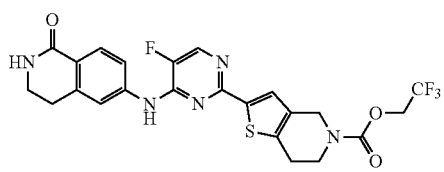 [SMILES: O=C1NCCc2cc(Nc3nc(-c4cc5c(s4)CCN(C(=O)OCC(F)(F)F)C5)ncc3F)ccc21] |
| C76. | 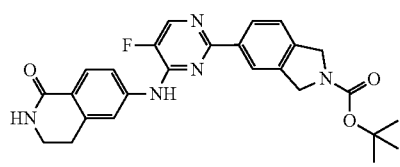 [SMILES: CC(C)(C)OC(=O)N1Cc2ccc(-c3ncc(F)c(Nc4ccc5c(c4)CCNC5=O)n3)cc2C1] |
| C77. | 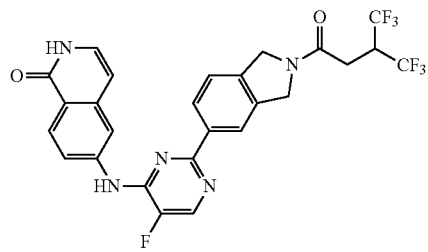 [SMILES: O=C(CC(C(F)(F)F)C(F)(F)F)N1Cc2ccc(-c3ncc(F)c(Nc4ccc5c(=O)[nH]ccc5c4)n3)cc2C1] |
| C78. | 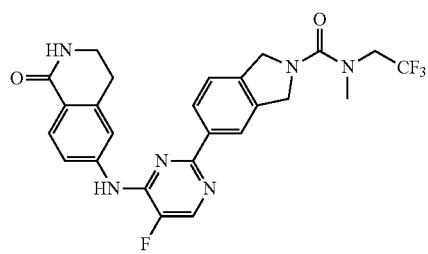 [SMILES: CN(CC(F)(F)F)C(=O)N1Cc2ccc(-c3ncc(F)c(Nc4ccc5c(c4)CCNC5=O)n3)cc2C1] |

| No. | Structure |
|---|---|
| C79. | 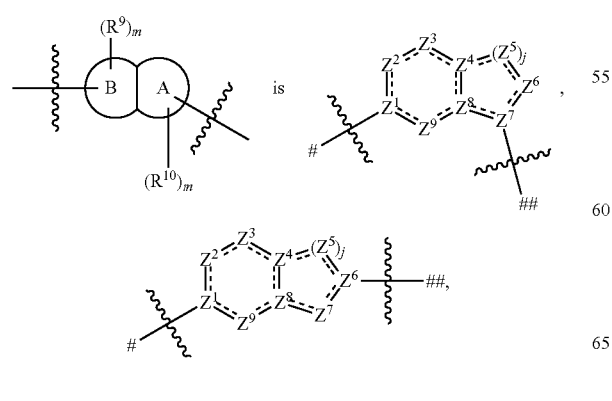 |
| C80. | 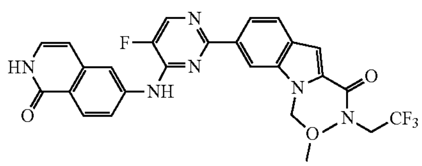 [SMILES: COCn1c(C(=O)N(C)CC(F)(F)F)cc2ccc(-c3ncc(F)c(Nc4ccc5c(=O)[nH]ccc5c4)n3)cc21] |
| C81. | 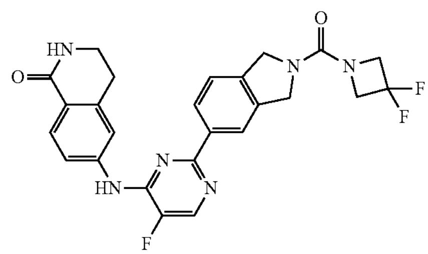 [SMILES: O=C1NCCc2cc(Nc3nc(-c4ccc5c(c4)CN(C(=O)N4CC(F)(F)C4)C5)ncc3F)ccc21] |
| C82. | 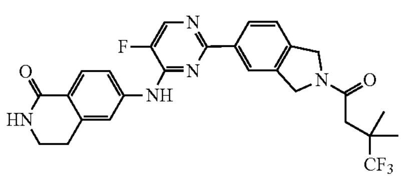 |

9. A pharmaceutical composition comprising a prophylactically or therapeutically effective amount of the compound according to claim 1 or a pharmaceutically acceptable salt, ester, stereoisomer, polymorph, solvate, N-oxide, or isotopically labeled compound thereof, and a pharmaceutically acceptable carrier.

10. The compound according to claim 3 or a pharmaceutically acceptable salt, ester, stereoisomer, polymorph, solvate, N-oxide, or isotopically labeled compound thereof, wherein

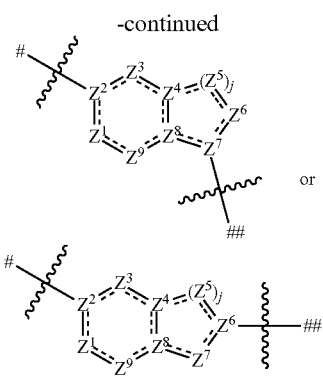

the above group is attached to ring C at either of the two positions labeled # or ##, and is attached to $R^1$ at the other position;

wherein $=$ represents either a single or a double bond, and the adjacent bonds are not double bonds simultaneously;

$Z^1$, $Z^2$, $Z^3$, $Z^4$, $Z^5$, $Z^6$, $Z^7$, $Z^8$ and $Z^9$, at each occurrence, are each independently selected from the group consisting of C, $CR^9$, $C(R^9)_2$, $CR^{10}$, $C(R^{10})_2$, $C(=O)$, N, $NR^9$, $NR^{10}$, O and S;

j is 0, 1, 2, 3 or 4;

provided that at most two groups among $Z^1$-$Z^9$ are simultaneously $C(=O)$.

11. The compound according to claim 3 or a pharmaceutically acceptable salt, ester, stereoisomer, polymorph, solvate, N-oxide, or isotopically labeled compound thereof, wherein $Z^1$, $Z^2$, $Z^3$, $Z^4$, $Z^5$, $Z^6$, $Z^7$, $Z^8$ and $Z^9$, at each occurrence, are each independently selected from the group consisting of C, CH, CF, CCl, CCH$_3$, CH$_2$, C(CH$_3$)$_2$, C—OCH$_3$, C(=O), N, NH, NCH$_3$, NCH$_2$CH$_3$, NCH(CH$_3$)$_2$, NCH=CH$_2$, NCH$_2$F, NCHF$_2$, NCH$_2$CHF$_2$, NC(=O) CH$_3$, NCH$_2$OH, NCH$_2$OMe, NCH$_2$CH$_2$OMe, NCH$_2$—O(P=O)(OH)$_2$,

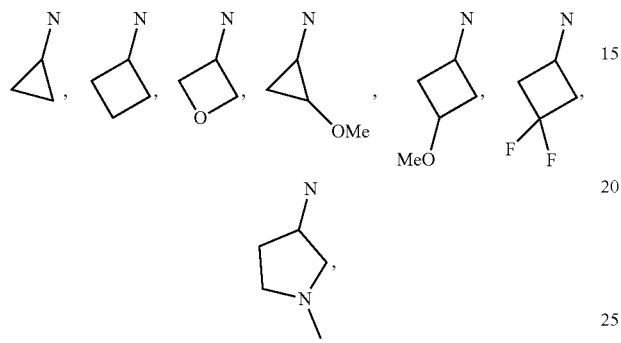

NCH$_2$CH$_2$—N(CH$_3$)$_2$, O and S.

12. The compound according to claim 3 or a pharmaceutically acceptable salt, ester, stereoisomer, polymorph, solvate, N-oxide, or isotopically labeled compound thereof, wherein

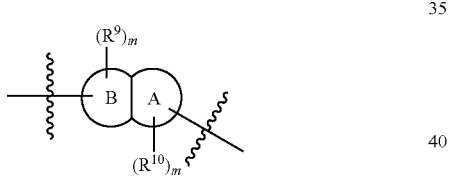

is selected from the group consisting of

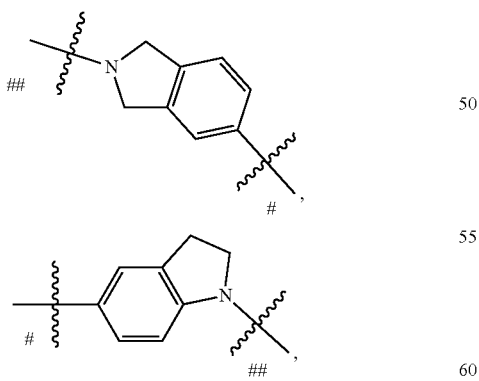

the above group is attached to ring C at either of the two positions labeled # or ##, and is attached to $R^1$ at the other position.

13. The pharmaceutical composition according to claim 9, wherein the pharmaceutical composition is in the form of a solid, semi-solid, liquid, or gas preparation.

* * * * *